US011458064B2

(12) United States Patent
Asbeck et al.

(10) Patent No.: US 11,458,064 B2
(45) Date of Patent: *Oct. 4, 2022

(54) SOFT EXOSUIT FOR ASSISTANCE WITH HUMAN MOTION

(71) Applicant: President and Fellows of Harvard College, Cambridge, MA (US)

(72) Inventors: Alan Thomas Asbeck, Waltham, MA (US); Ye Ding, Cambridge, MA (US); Ignacio Galiana Bujanda, Cambridge, MA (US); Sangjun Lee, Cambridge, MA (US); Diana Wagner, Charlotte, NC (US); Conor J. Walsh, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/538,746

(22) Filed: Aug. 12, 2019

(65) Prior Publication Data

US 2020/0100976 A1 Apr. 2, 2020

Related U.S. Application Data

(63) Continuation of application No. 15/511,894, filed as application No. PCT/US2015/051107 on Sep. 19, 2015, now Pat. No. 10,434,030.

(Continued)

(51) Int. Cl.
*A61H 3/00* (2006.01)
*A61F 5/01* (2006.01)
*A61H 1/02* (2006.01)

(52) U.S. Cl.
CPC .............. *A61H 3/00* (2013.01); *A61F 5/01* (2013.01); *A61H 1/0266* (2013.01);
(Continued)

(58) Field of Classification Search
CPC ...... A61H 3/00; A61H 1/0266; A61H 1/0262; A61F 5/01
See application file for complete search history.

(56) References Cited

U.S. PATENT DOCUMENTS

2010/0038983 A1 2/2010 Bhugra et al.
2011/0009793 A1 1/2011 Lucero et al.
(Continued)

FOREIGN PATENT DOCUMENTS

JP 2008-017981 A 1/2008
JP 2014-073222 A 4/2014
(Continued)

OTHER PUBLICATIONS

International Search Report and Written Opinion in International Application No. PCT/US2015/051107, dated Aug. 5, 2016.

*Primary Examiner* — Brian A Dukert
(74) *Attorney, Agent, or Firm* — Wolf, Greenfield & Sacks, P.C.

(57) ABSTRACT

Systems and methods for providing assistance with human motion, including hip and ankle motion, are disclosed. Sensor feedback is used to determine an appropriate profile for actuating a wearable robotic system to deliver desired joint motion assistance. Variations in user kinetics and kinematics, as well as construction, materials, and fit of the wearable robotic system, are considered in order to provide assistance tailored to the user and current activity.

32 Claims, 36 Drawing Sheets

Related U.S. Application Data

(60) Provisional application No. 62/193,793, filed on Jul. 17, 2015, provisional application No. 62/183,149, filed on Jun. 22, 2015, provisional application No. 62/173,887, filed on Jun. 10, 2015, provisional application No. 62/107,729, filed on Jan. 26, 2015, provisional application No. 62/052,562, filed on Sep. 19, 2014.

(52) U.S. Cl.
CPC ...... *A61H 1/0262* (2013.01); *A61H 2003/007* (2013.01); *A61H 2201/165* (2013.01); *A61H 2201/1659* (2013.01); *A61H 2201/1695* (2013.01); *A61H 2201/501* (2013.01); *A61H 2201/503* (2013.01); *A61H 2201/5038* (2013.01); *A61H 2201/5061* (2013.01); *A61H 2201/5069* (2013.01); *A61H 2201/5071* (2013.01); *A61H 2201/5079* (2013.01); *A61H 2201/5084* (2013.01); *A61H 2201/5097* (2013.01); *A61H 2205/106* (2013.01)

(56) References Cited

U.S. PATENT DOCUMENTS

| | | |
|---|---|---|
| 2011/0093089 A1 | 4/2011 | Martin |
| 2011/0201978 A1 | 8/2011 | Jeon et al. |
| 2012/0253234 A1 | 10/2012 | Yang et al. |
| 2013/0085317 A1 | 4/2013 | Feinstein |
| 2013/0310979 A1 | 11/2013 | Herr et al. |
| 2014/0194781 A1 | 7/2014 | Einarsson et al. |
| 2015/0173993 A1 | 6/2015 | Walsh et al. |

FOREIGN PATENT DOCUMENTS

| | | |
|---|---|---|
| JP | 2017-529161 A | 10/2017 |
| WO | WO 2013/049658 A1 | 4/2013 |
| WO | WO 2014/109799 A1 | 7/2014 |
| WO | WO 2014/194257 A1 | 12/2014 |

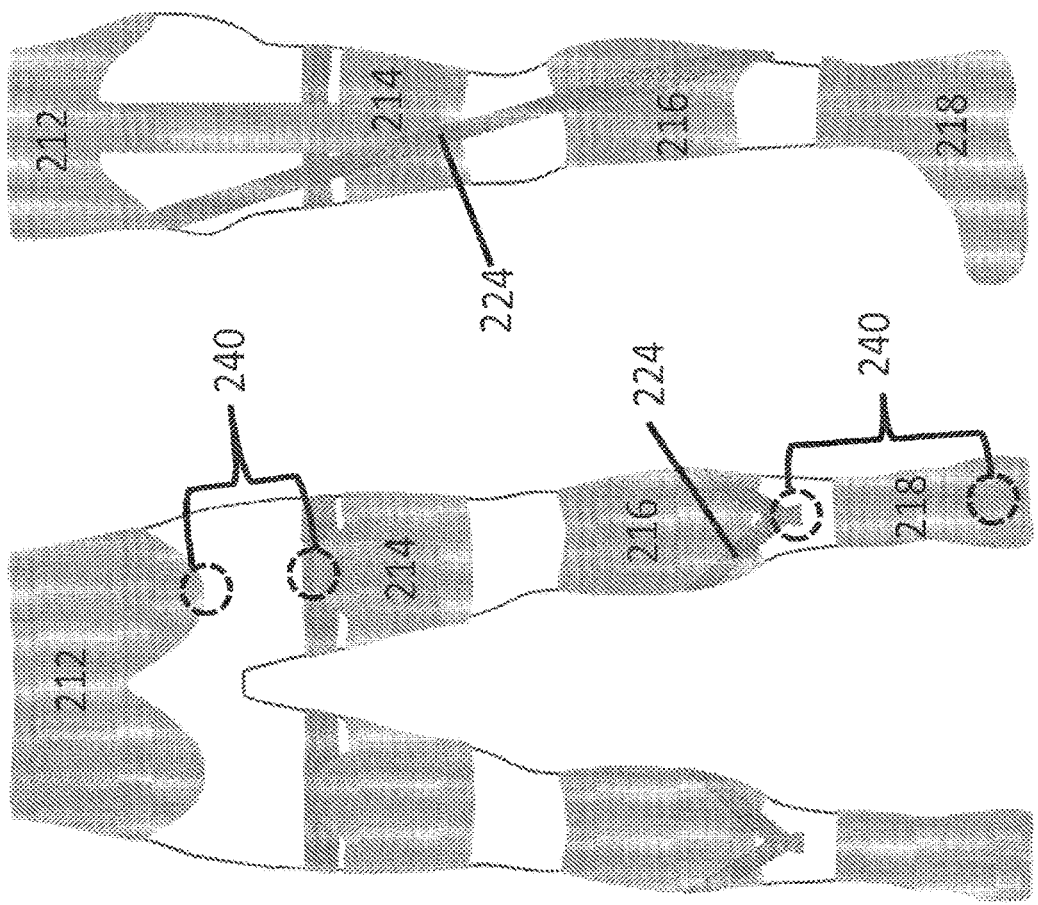
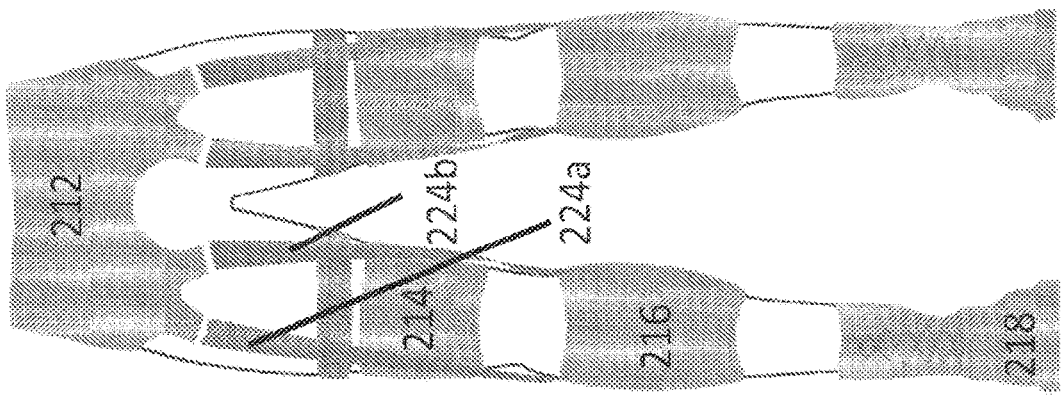
FIG. 3C
FIG. 3B
FIG. 3A

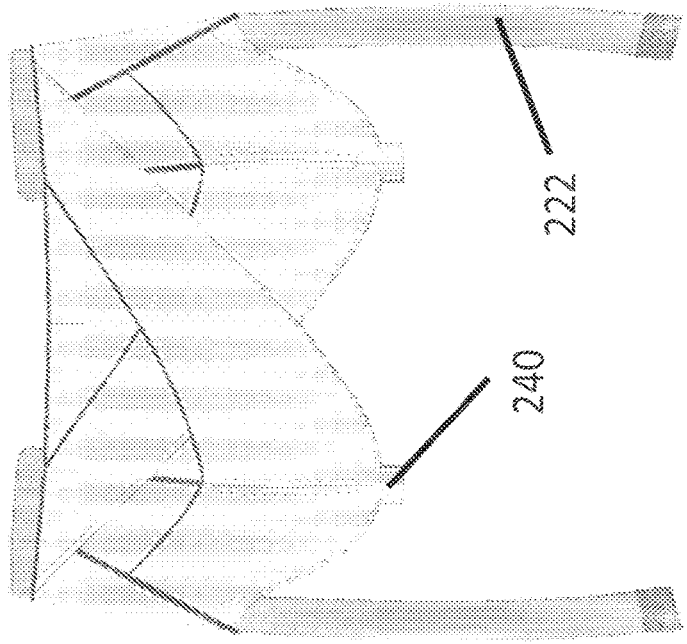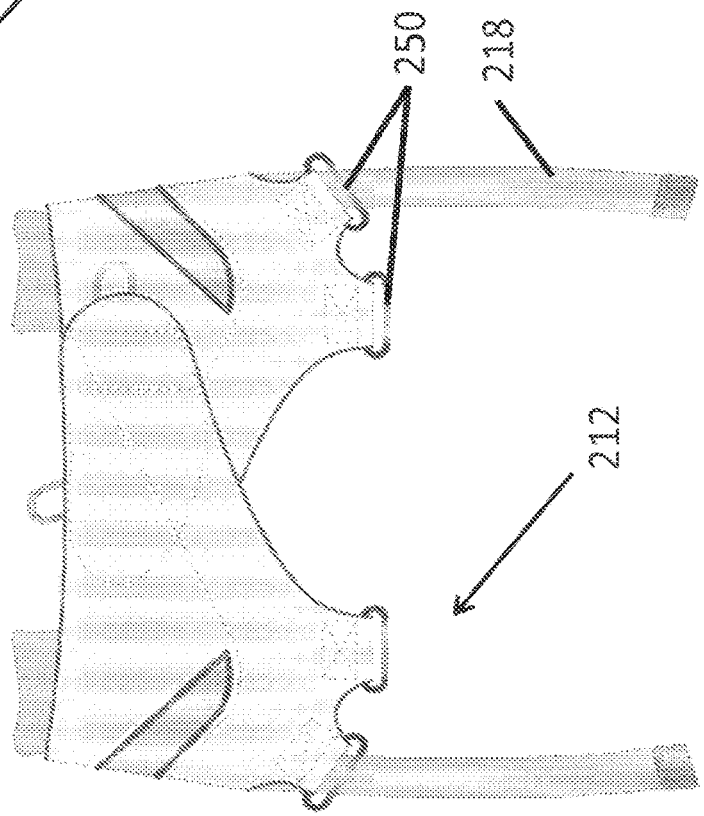

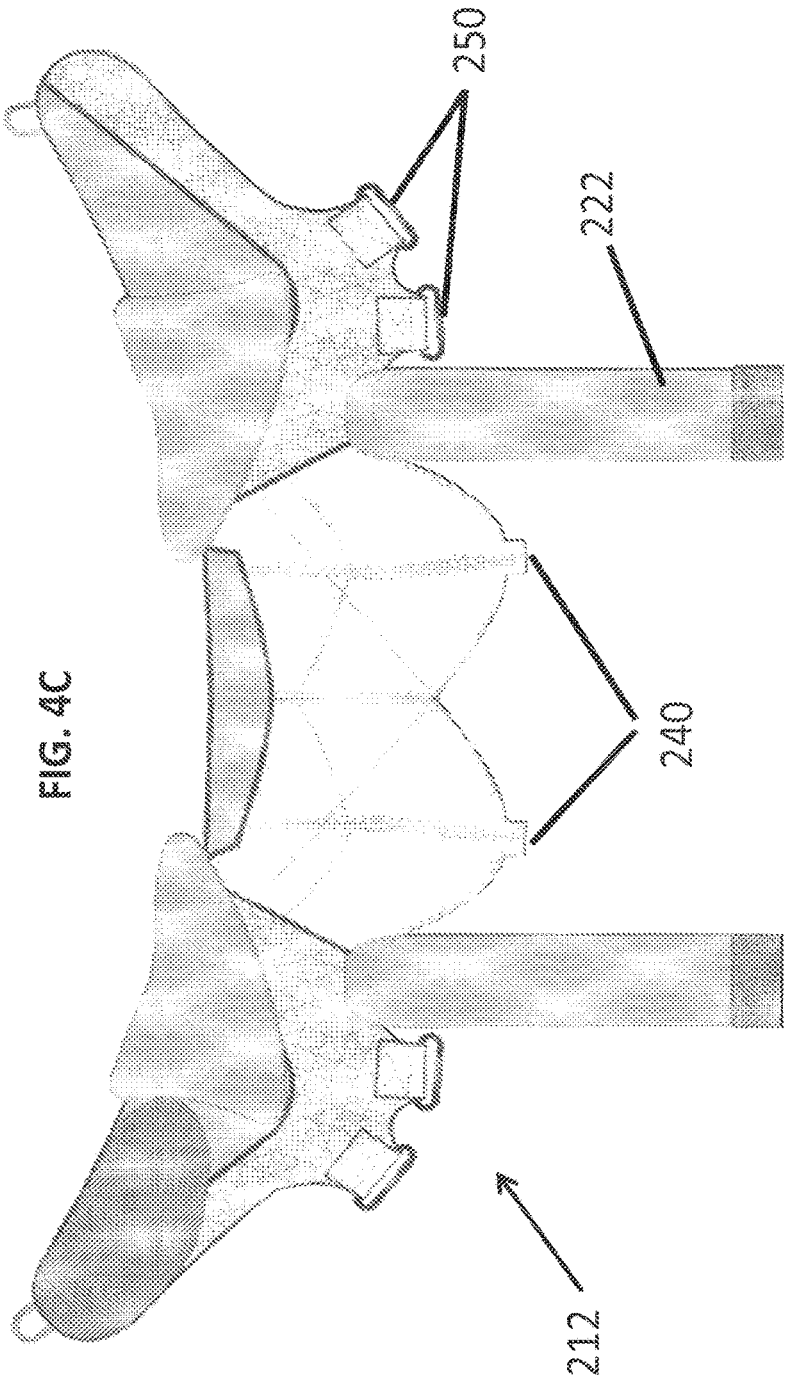

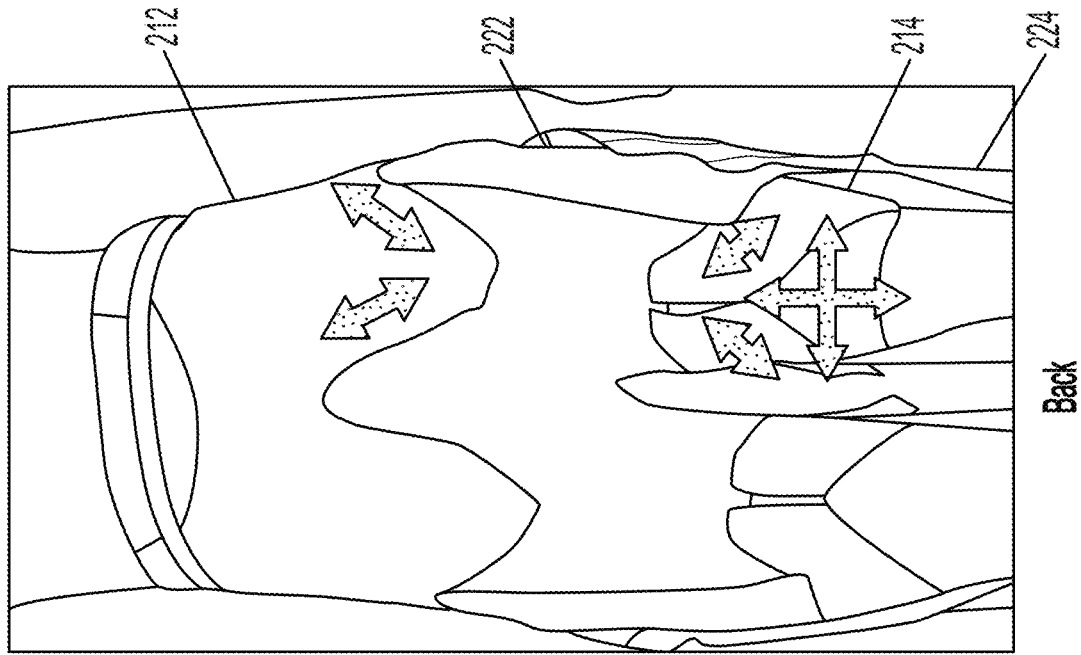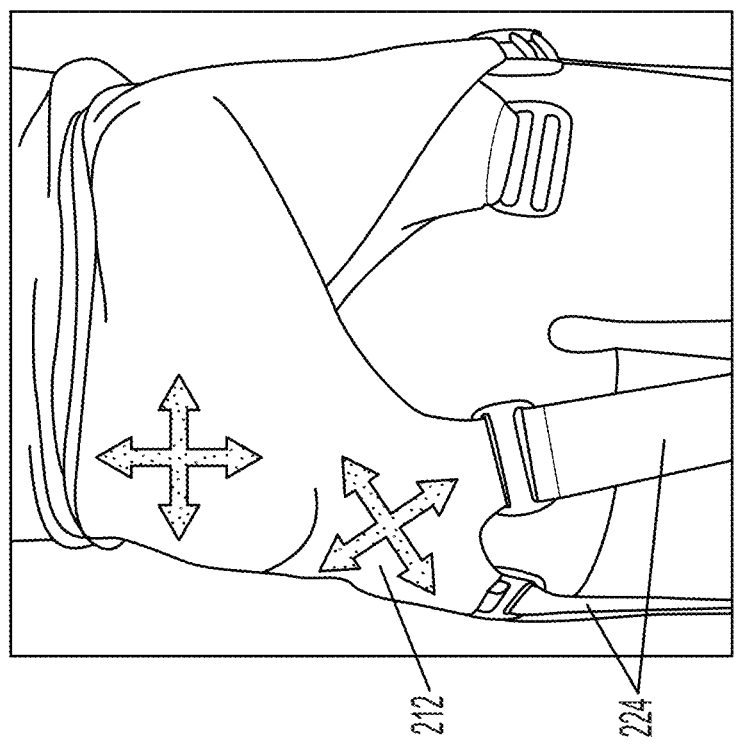

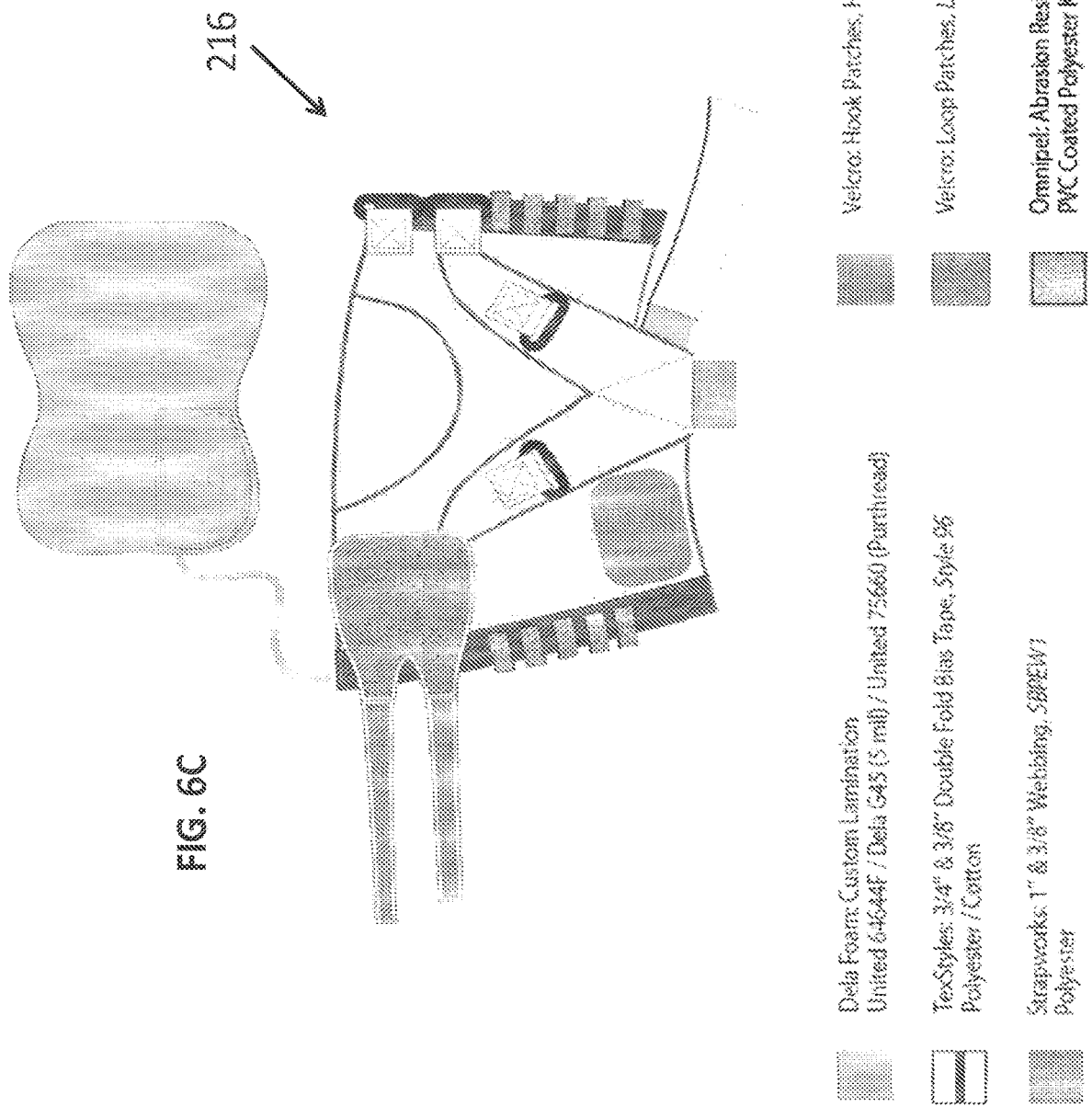

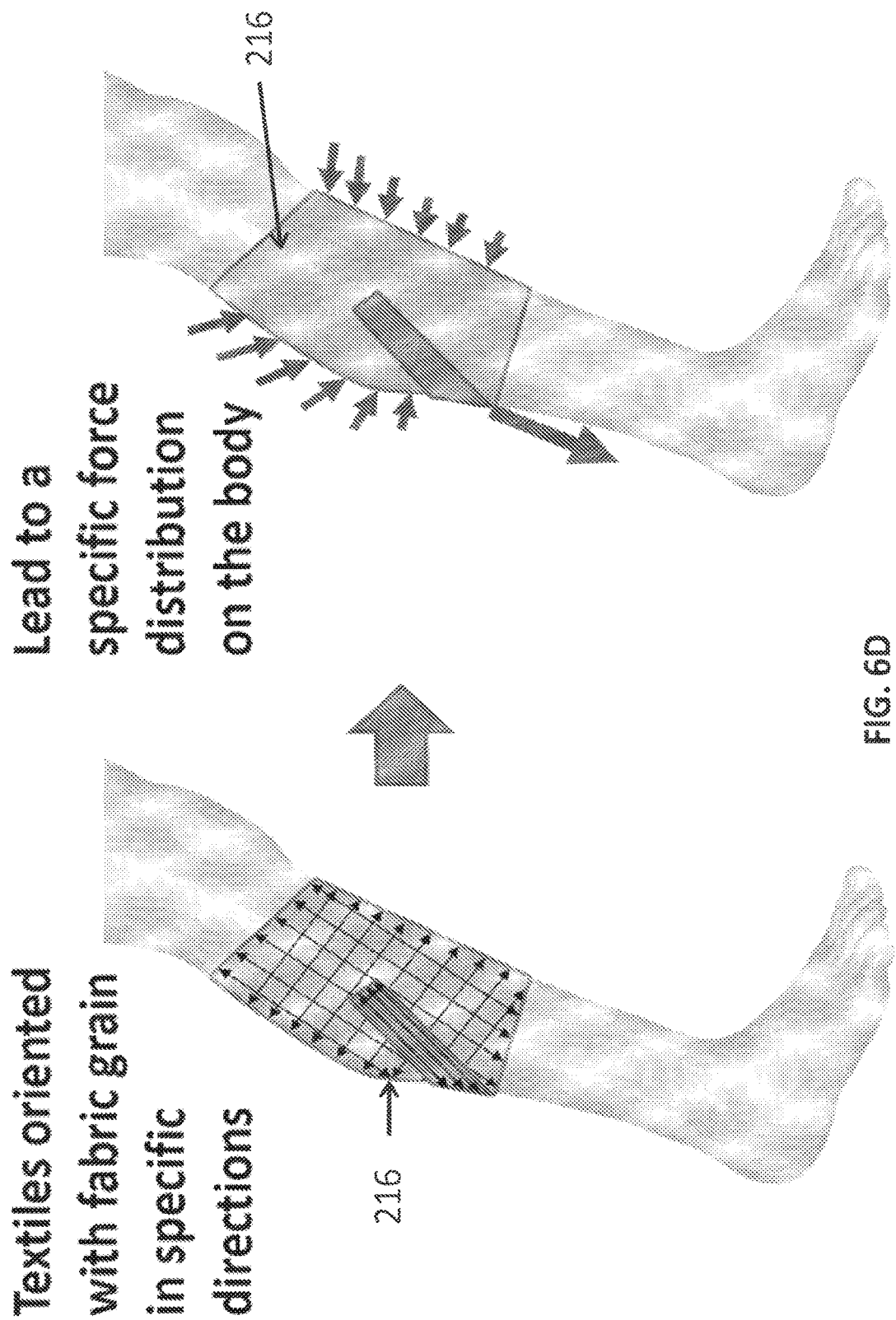

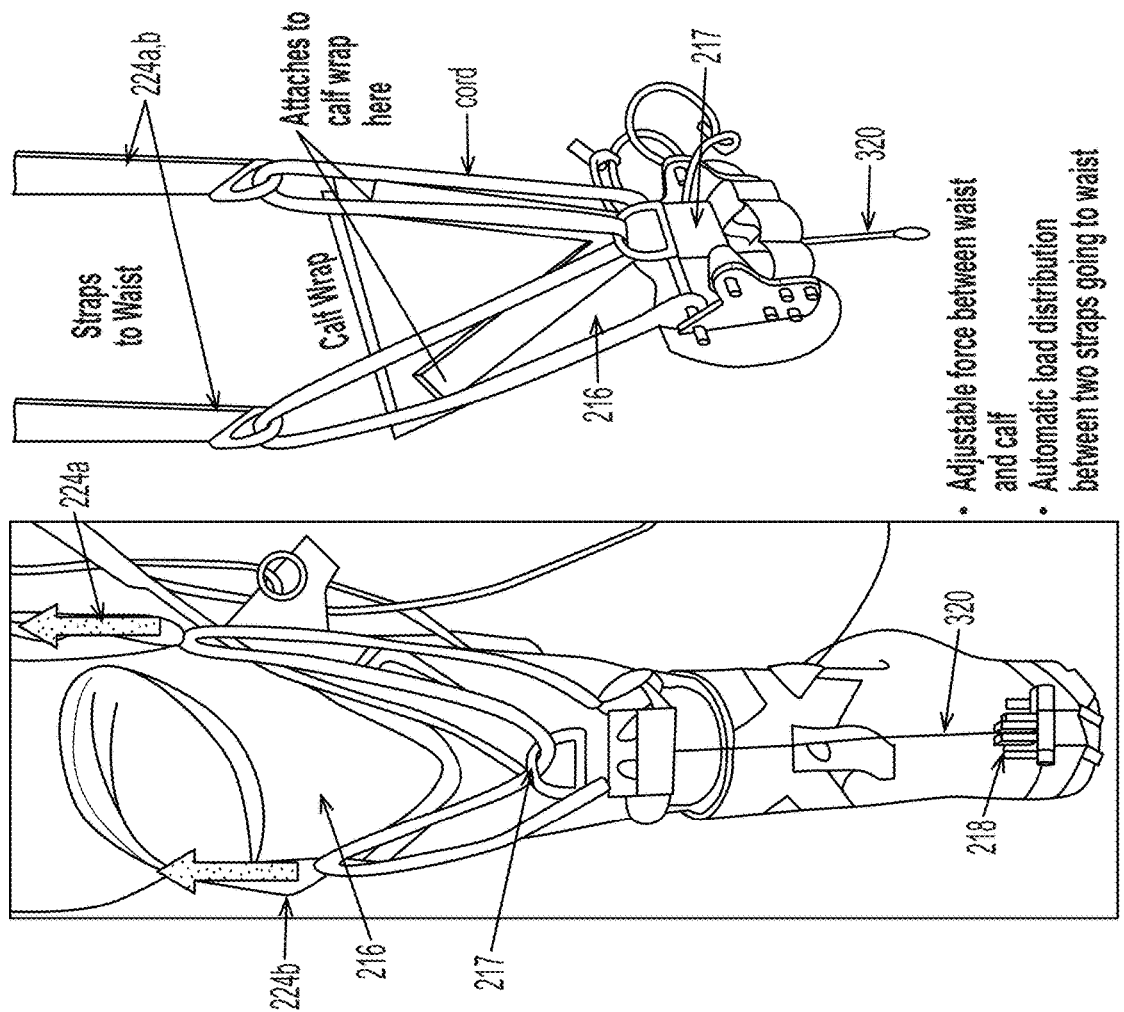

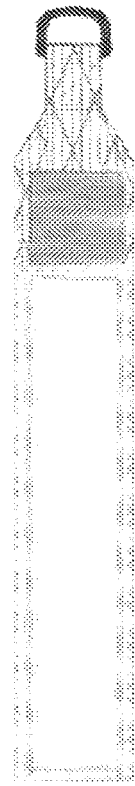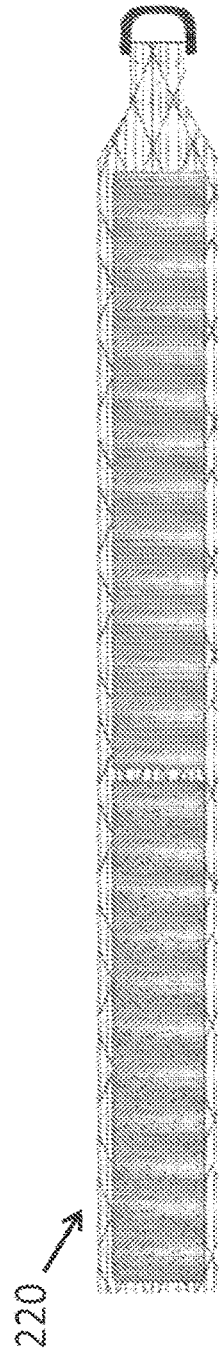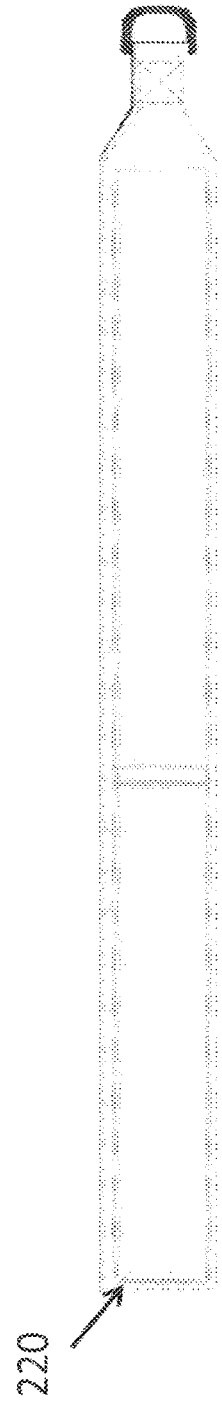

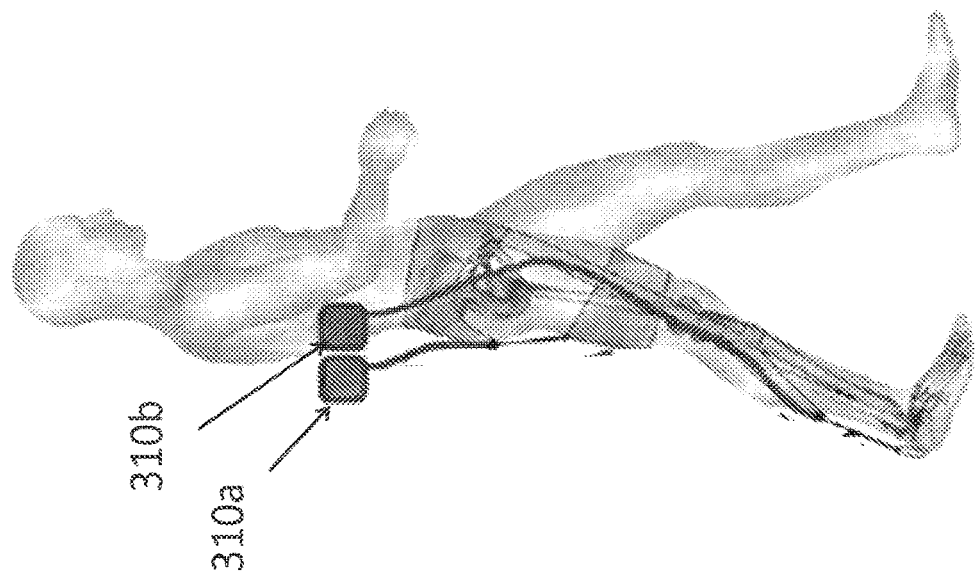
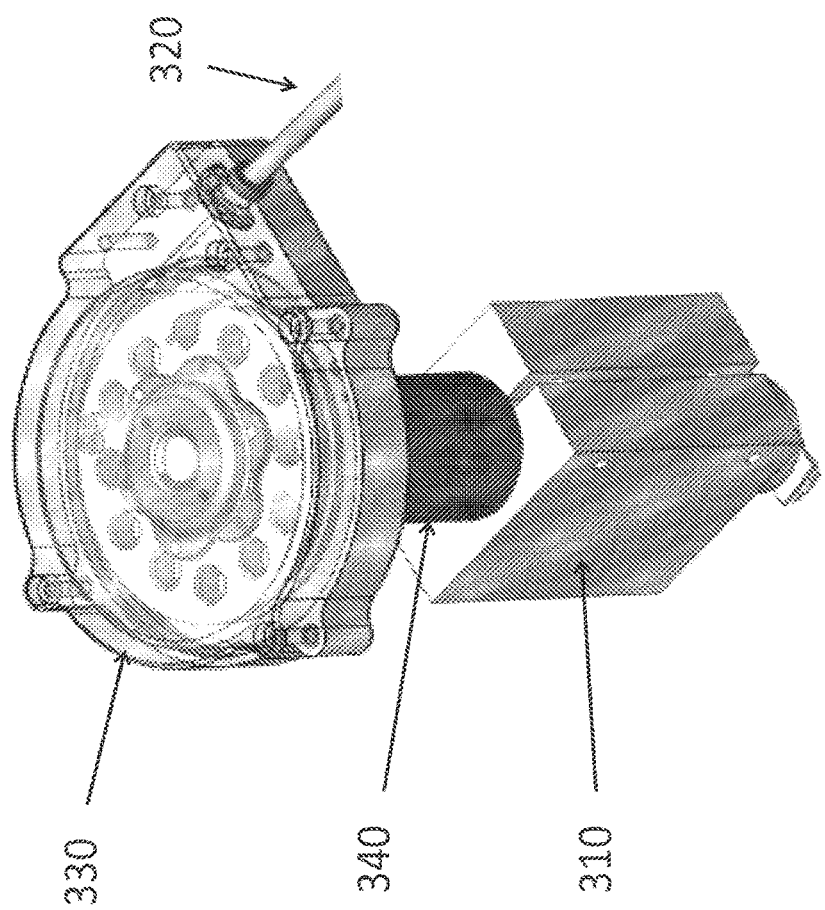
FIG. 10
FIG. 11

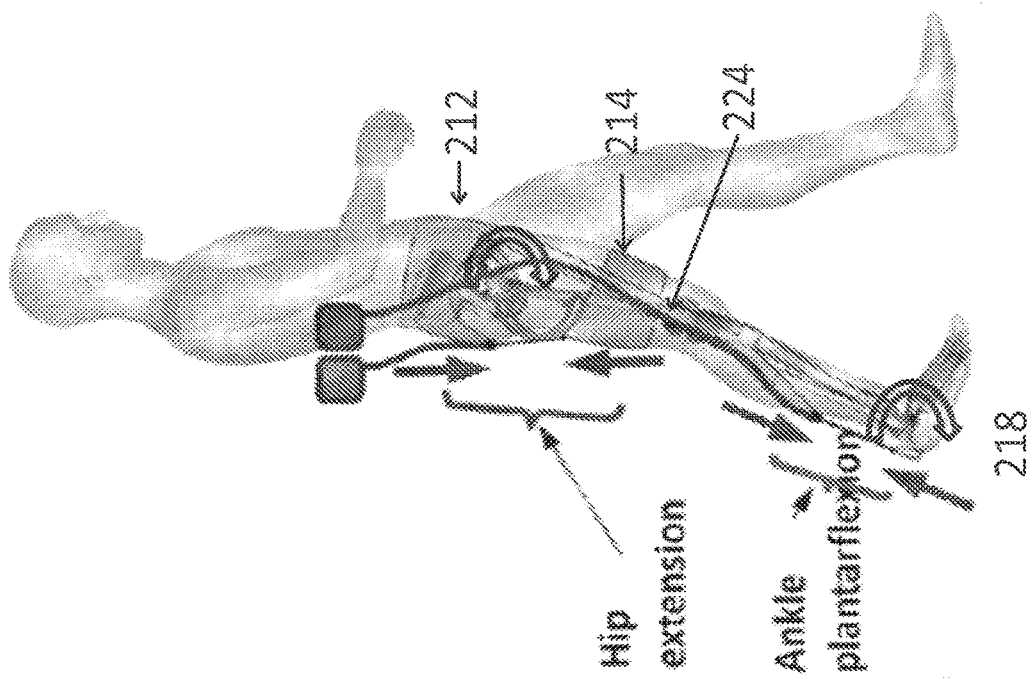
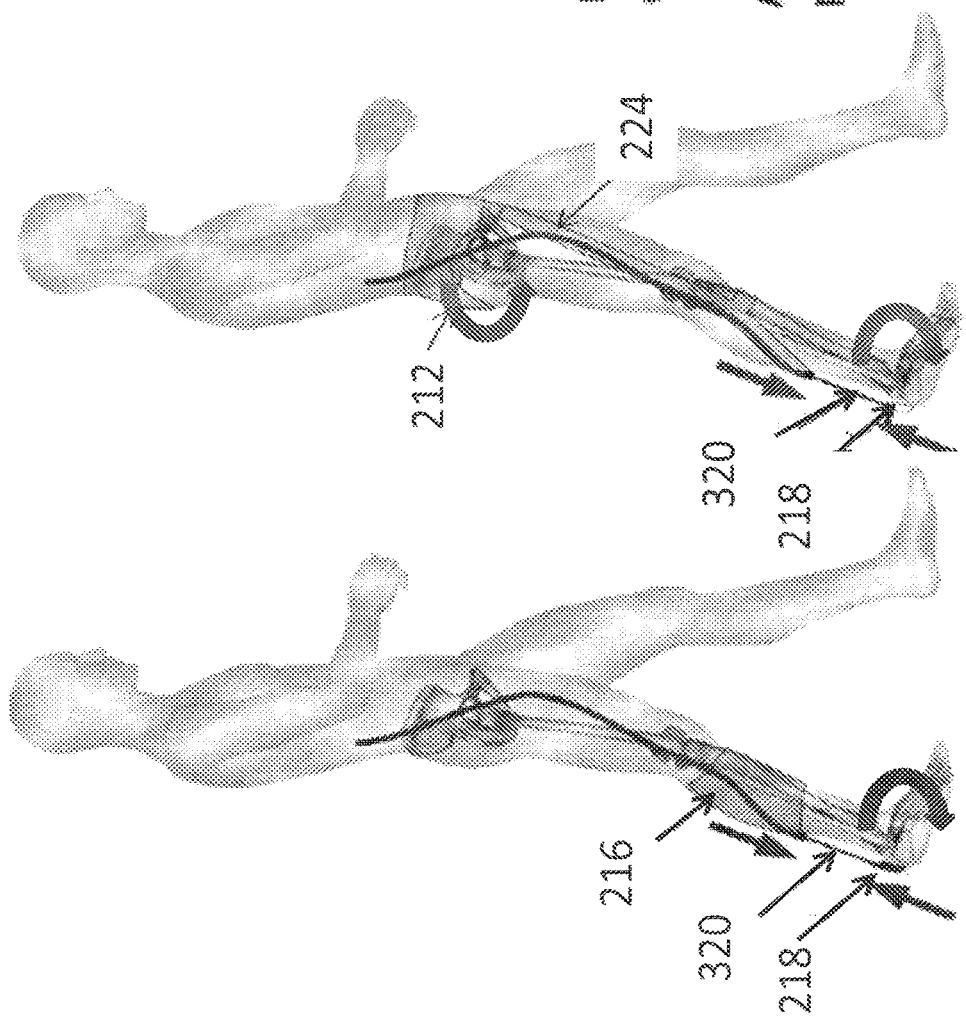
FIG. 12C  FIG. 12D  FIG. 12E

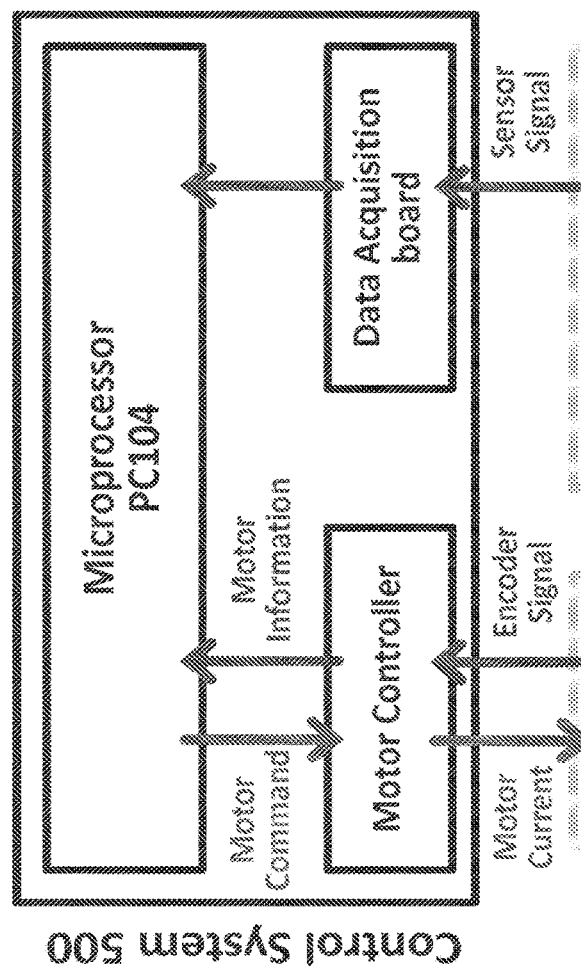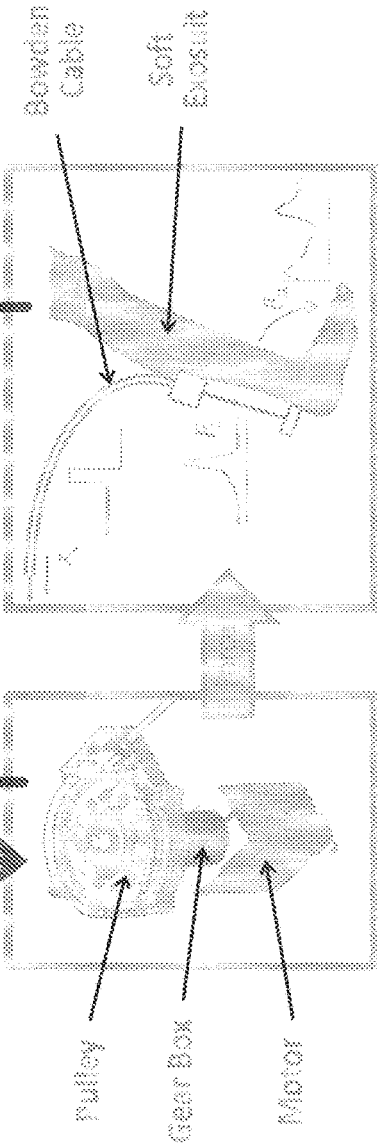
FIG. 15

Hip range of motion in sagittal plane

Validation of walking speed estimation

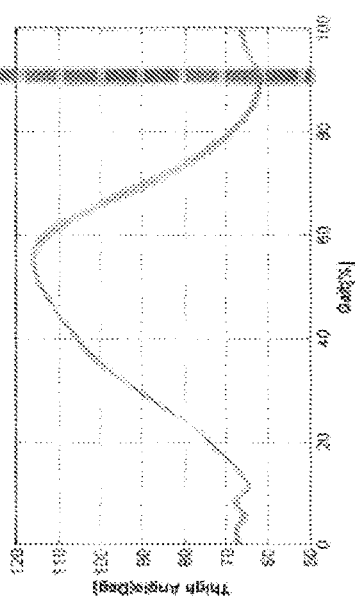
FIG. 22A
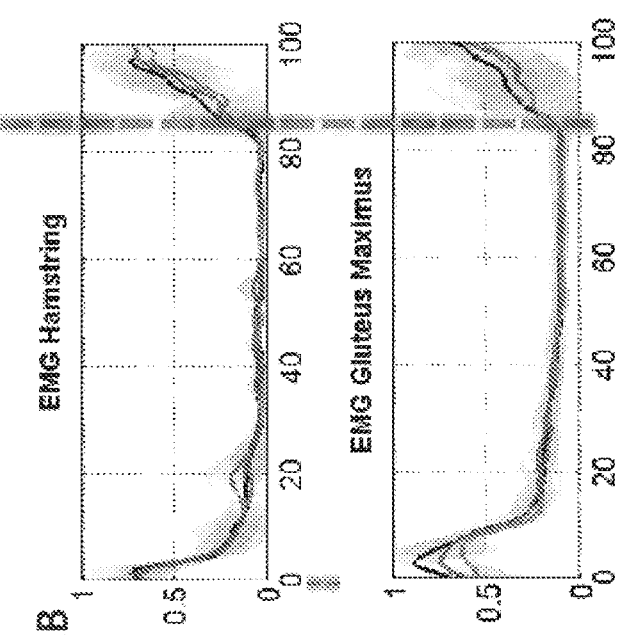
FIG. 22B
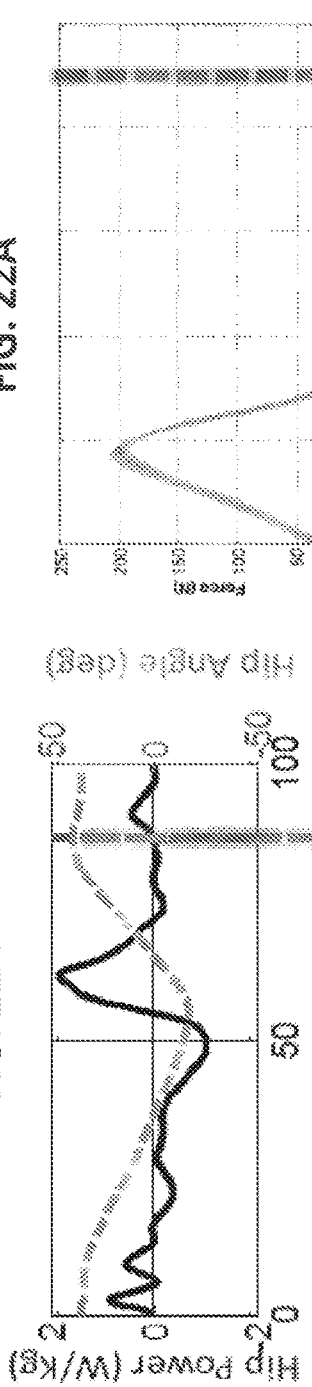
FIG. 21A
FIG. 21B
FIG. 21C

SOFT EXOSUIT FOR ASSISTANCE WITH HUMAN MOTION

CROSS-REFERENCE TO RELATED APPLICATIONS

The application is a continuation of U.S. application Ser. No. 15/511,894, filed Mar. 16, 2017, which is a U.S. National phase application of PCT International Patent Application No. PCT/2015/051107, filed on Sep. 19, 2015, which claims priority to U.S. Provisional Patent Application No. 62/052,562, filed Sep. 19, 2014; U.S. Provisional Patent Application No. 62/107,729, filed Jan. 26, 2015; U.S. Provisional Patent Application No. 62/173,887, filed Jun. 10, 2015; U.S. Provisional Patent Application No. 62/183,149, filed Jun. 22, 2015; and U.S. Provisional Patent Application No. 62/193,793, filed Jul. 17, 2015, and the entirely of all these applications are hereby incorporated by reference.

STATEMENT REGARDING FEDERALLY SPONSORED RESEARCH OR DEVELOPMENT

This invention was made with government support under W911NF-14-00051 and W911QX-12-C-0084 awarded by the U.S. Department of Defense. The government has certain rights in the invention.

FIELD

The presently disclosed embodiments relate to motion assistance devices, and more particularly to soft exosuit systems and methods for providing assistance with human motion, including hip motion and ankle motion.

BACKGROUND

Over the last decade, a number of lower-extremity exoskeletons have been developed to assist human gait in various conditions. Some devices have been designed to assist impaired or able-bodied people, while others have been designed to make load carriage easier.

Conventionally, these devices have consisted of rigid exoskeleton structures enabling high assistive torques to the wearer. However, rigid frames can restrict the natural movement of the wearer and may apply undesired forces when they are misaligned with the wearer's biological joints. Moreover, rigid devices may have large inertias particularly on distal areas, which can hinder the motion of the wearer and provide challenges from a control perspective.

Exosuits utilizing primarily soft, flexible or semi-flexible components (e.g., textiles) have been developed to address some of these issues characteristic of exoskeletons. The conformal, unobtrusive and compliant nature of many such exosuits has mitigated many of the above-identified issues associated with rigid exosuits, but in turn, raise new issues. Soft exosuits are typically not load-bearing like rigid exoskeletons, thus forces generated in the exosuit are ultimately transferred to and borne by the user's body. As such, comfort and safety considerations may limit the amount of force that can be generated to assist motion. Additionally, as soft exosuits may be worn directly against a user's skin or over clothing, comfort can be a key design consideration. Often, however, design considerations for comfort often conflict with those for maintaining efficient system stiffness for transferring loads therethrough. In particular, many comfortable textiles are prone to stretching when placed under tension. Such stretching can cause effectively bleed energy from the exosuit, making it necessary to provide larger motors and consume higher amounts of power to produce the same assistive force to the human body than if higher modulus materials were used. Additionally, stretching can cause elements of the exosuit to become misaligned and/or displaced from their intended positions on the body, potentially leading to discomfort, unnatural torqueing of joints, and increased power requirements. The inherently compliant and nonlinear mechanical structure of soft exosuits can also make it difficult to accurately and reliably deliver a desired amount of force to various portions of the user's body to assist with motion. Accordingly, there is a need for a lightweight, comfortable exosuit for assistive motion configured to maintain a desired position and alignment on the body, and provide efficient load paths and transfer characteristics therethrough.

Apart from the mechanical challenges of actuating a soft exosuit, another is in delivering effective assistance given considerable variability in joint kinematics and patterns of muscle activation. Existing approaches to controlling motion assistance estimate the onset of assistance using historical data or predetermined constants, and thus fail to account for normal or unpredictable variations in the wearer's current stride. In particular, many control systems utilize historical or predetermined data from previous strides to estimate the onset of the motion to be assisted during a current stride. Other systems may be configured to apply power at predetermined, constant time offsets set to correspond with certain portions of an average person's gait cycle. This may be problematic in situations where the user's gait varies, which is often the case in real-life activity. Accordingly, there is a need for a control system configured to adapt in real-time to a user's motion and thus provide assistive power with appropriate timing and magnitude.

Another challenge is delivering effective assistance given the considerable variability in wearer kinetics due to gender, age, height, body weight, and spatial-temporal factors such as locomotive speed. Existing control systems fail to account for these variations, instead providing a one-size-fits-all magnitude of assistance that is not tailored to the particular wearer of the exosuit. Accordingly, there is a need for a control system configured to adapt the magnitude of assistance to the particular wearer of the exosuit and/or characteristics of the activity being performed.

SUMMARY

Systems and methods for providing assistance with human motion using an exosuit system are disclosed. An exosuit, in various embodiments, may be actuated to apply assistive forces to the human body to augment forces generated by underlying musculature. Various sensors may be used to monitor forces generated in the exosuit, as well as the motion of the user's body, in order to determine a suitable profile for actuating the exosuit so as to deliver desired levels of assistance with appropriate timing.

Variations in user kinetics and kinematics, as well as construction, materials, and fit of the wearable robotic system, are considered in various embodiments in order to provide assistance tailored to the user and current activity. The exosuit, in various embodiments, may be actuated using an iterative approach that compares actual forces or integral powers produced in the exosuit to those desired, thus ensuring appropriate actuation magnitude regardless of variations in fit and body characteristics amongst users of the exosuit system. The magnitude of assistance provided, in various embodiments, may be influenced by factors that affect biological loads on the body, such as body weight and spatial-temporal factors like locomotive speed. Further, in various embodiments, real-time detection of body motion and gait events may utilized to tailor the timing of assistance to the actual motion of the user at any given time, thereby accounting for normal or unpredictable variations in a user's motion or gait.

Motion assistance, in various embodiments, may be provided to a user's hip joint to assist with locomotion. This may include, in various embodiments, determining a desired peak force or integral power to be generated by the exosuit system during a current gait cycle of the user, generating an actuation profile according to which the exosuit may be actuated to generate the desired peak force or integral power, monitoring real-time measurements of an angle of the hip joint to detect when the hip joint reaches a maximum flexion angle, and in response to detecting that the angle of the hip joint has reached the maximum flexion angle, actuating the wearable robotic system according to the actuation profile to assist with an extension motion of the hip joint of the user.

Motion assistance, in various embodiments, may be provided to a user's ankle joint to assist with locomotion. Assistance, in an embodiment, may be provided during one or a combination of stance dorsiflexion and stance plantarflexion motion of the ankle joint. Appropriate timing may be determined by monitoring in real-time sensor measurements to detect a heel strike and a subsequent change in ankle rotation direction indicative of the transition from stance dorsiflexion motion to stance plantarflexion motion. In response to detecting the first change in direction of the measured rotational velocity of the ankle joint, the exosuit may be actuated to assist with a plantarflexion motion of the ankle joint of the user. The exosuit system, in an embodiment, may be configured to independently control negative and positive powers delivered to the ankle joint during dorsiflexion and plantarflexion motions, respectively.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 3A depicts a front view of a representative embodiment of a soft exosuit;

FIG. 3B depicts a rear view of a representative embodiment of a soft exosuit;

FIG. 3C depicts a side view of a representative embodiment of a soft exosuit;

FIG. 4A illustrates a front view of a representative embodiment of a waist anchor member;

FIG. 4B illustrates a rear view of a representative embodiment of a waist anchor member;

FIG. 4C illustrates a front view of an alternative embodiment of a waist anchor member;

FIG. 4D illustrates an embodiment of a waist anchor where connection elements join the front of the waist anchor member;

FIG. 4E illustrates an embodiment of a waist anchor where connection elements join the side of the waist anchor member;

FIG. 6C illustrates an embodiment of a calf anchor;

FIG. 6D illustrates a calf anchor comprising textiles that may be oriented with the fabric grain in specific directions;

FIG. 6H depicts a representative mechanism for coupling and actuation and connection elements with a calf anchor.

FIG. 8A illustrate a perspective view of a representative embodiment of a connection element;

FIG. 8B illustrate a perspective view of a representative embodiment of a connection element;

FIG. 8C illustrate a perspective view of a representative embodiment of a connection element;

FIG. 10 depicts a representative actuation system for generating tensile forces in a soft exosuit;

FIG. 11 illustrates a motor located distally from a portion of a soft exosuit to which a cable is attached and extends therebetween;

FIG. 12C illustrates an embodiment of a soft exosuit comprising a calf anchor and a foot anchor;

FIG. 12D illustrates an embodiment of a soft exosuit comprising a waist anchor, a foot anchor, and connection elements extending therebetween;

FIG. 12E illustrates an embodiment of a soft exosuit including two modules with a first module and a second module;

FIG. 15 shows an exemplary embodiment of a control system;

FIG. 21A depicts a typical gait cycle;

FIG. 21B depicts a gait cycle of a hamstring;

FIG. 21C depicts a gait cycle of a gluteus maximus;

FIG. 22A depicts an exemplary application of a force to assist with hip motion;

FIG. 22B depicts an exemplary application of a force to assist with thigh motion;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for providing assistance with human motion using an exosuit system are disclosed. Embodiments of the present disclosure generally provide exosuit system 100 for assisting natural, muscle-driven motion via a soft exosuit in a manner suitable to reduce the effort required in performing the natural motion, to increase one's endurance or to enable motions that would be otherwise be impossible for one.

Exosuit System 100

Embodiments of exosuit system 100 may provide a novel soft exosuit design configured with efficient load paths for directing and distributing potentially high assistive forces to various portions an exosuit user's body, whilst maintaining comfort and minimizing obstruction of the user's natural movements. Exosuit system 100 may monitor the natural motion of the user to detect in real-time the onset of the motion to be assisted, as well as to detect or estimate how long the motion may last, so as to provide assistance that adapts to kinematic variations in the user's activity. Exosuit system 100 may further adapt to variations in the properties of the exosuit, how it fits the user, and other factors to reliably deliver a desired magnitude of assistance. Still further, exosuit system 100 may adapt the level of assistance to be provided to the user based on user body characteristic (e.g., build, weight), spatial-temporal factors (e.g., locomotive speed), and user comfort preferences, amongst others.

Figure 1:
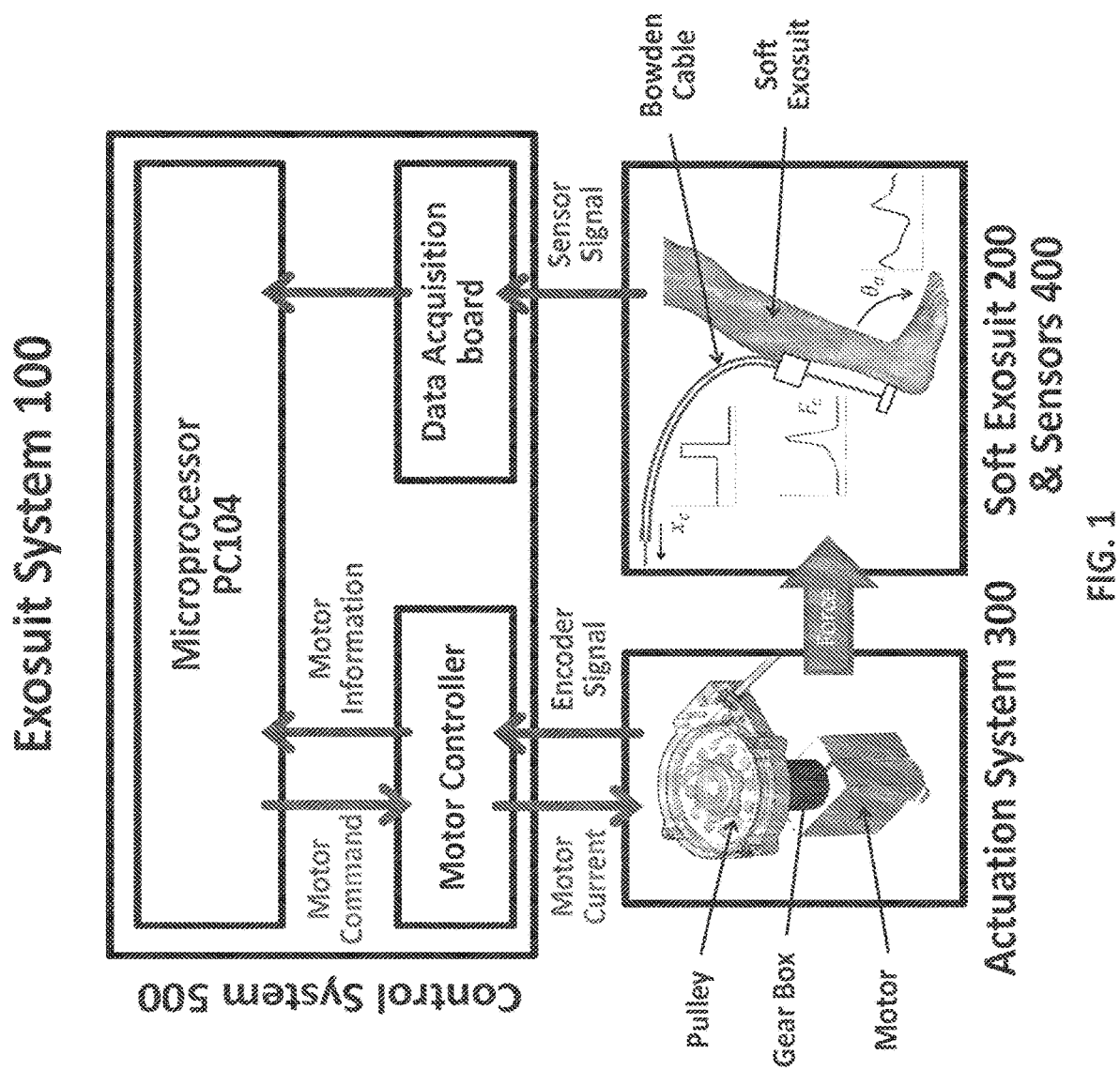
FIG. 1 depicts a representative embodiment of a soft exosuit.

FIG. 1 depicts a representative embodiment of exosuit system 100, which may generally include soft exosuit 200, actuation system 300, sensors 400, and control system 500. Soft exosuit 200 may be worn by a user, actuation system 300 may move components of soft exosuit 200 to generate tensile forces therein. Control system 500 may utilize measurements from sensors 400 to monitor the user's motion, as well as the forces being generated in soft exosuit 200, so as to control the timing and magnitude of assistance provided to the user.

Soft Exosuit 200

Figure 2:
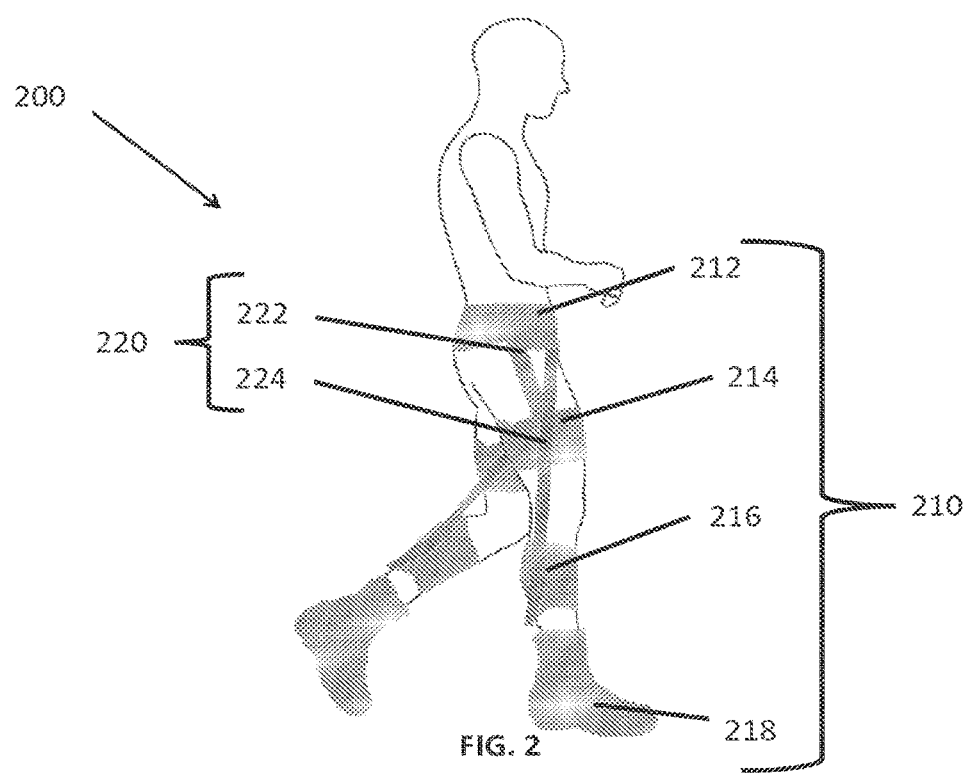
FIG. 2 depicts a representative embodiment of a soft exosuit.

FIG. 2 depicts a representative embodiment of soft exosuit 200. Soft exosuit 200 of exosuit system 100 may generally comprise one or more anchor members 210. Anchor member 210, in various embodiments, may comprise any wearable component capable of transferring loads generated in soft exosuit 200 to the body of the user. Exemplary embodiments of anchor member 210 may include, without limitation, a waist anchor 212, a thigh anchor 214, a calf anchor 216, and or a foot anchor 218. Waist anchor member 212, in an embodiment, may be any component configured to provide load support by securely strapping atop a user's hips, such as a waist belt. Thigh anchor member 214 and calf anchor member 216, in various embodiments, may be any components configured to provide load support by securely strapping about the exosuit user's thigh and calf, respectively, such as a thigh wrap or a calf wrap. Foot anchor member 218, in an embodiment, may be any footwear or other component suitable for being worn or otherwise coupled with the user's foot, such as a boot, that is configured to provide load support to an exosuit user's foot. Of course, soft exosuit 200 may include any number of suitable types of anchor members 210 and combinations thereof, and the present disclosure is not intended to be limited only to those exemplary embodiments described herein.

Still referring to FIG. 2, soft exosuit 200 may further comprise one or more connection elements 220. Connection elements 220, in various embodiments, may comprise one or a substantially continuous series of flexible, elongated components arranged to connect components of soft exosuit 200 to one another and to define a load path therebetween along which tensile forces may be transferred. One or more of connection elements 220, in an embodiment, may be substantially non-extensible so as to more efficiently transfer tensile forces throughout soft exosuit 200. In an embodiment, soft exosuit 200 may include a connection element 222 extending between and coupled to waist anchor 212 and thigh anchor 214, as shown. Additionally or alternatively, in another embodiment, soft exosuit 200 may include a connection element 224 extending between waist anchor 212 and a lower portion of the user's leg. In an embodiment, such a connection element 224 may be directly or indirectly coupled with calf anchor 216 and/or foot anchor 228. Of course, soft exosuit 200 may include any number of suitable types of connection elements 220 and combinations thereof, and the present disclosure is not intended to be limited only to those exemplary embodiments described herein.

FIG. 3A, FIG. 3B, and FIG. 3C depict additional perspectives (i.e., front view, rear view and side view, respectively) of soft exosuit 200 for the purpose of illustrating further characteristics of soft exosuit 200. Referring to FIG. 3A, soft exosuit 200 may include two connection elements 224a, 224b. First ends of connection elements 224a, 224b may be coupled with a front portion of waist belt 212 and intermediate portions of each connection element 224a, 224b may extend downwards along a front portion of the user's thigh. The intermediate portions may then split around the lateral sides of the knee so as to run alongside the center of rotation of the user's knee joint, as best shown in FIG. 3C. Referring to FIG. 3B and FIG. 3C, connection elements 224a, 224b may continue further downwards and wrap around the back of the user's lower leg, as shown. Referring to FIG. 3B, anchor members 210 may be provided with attachment points 240 to which one or more actuation elements 320 may attach, as later described in more detail.

Materials and Construction

One or more components of the soft exosuit system may be fabricated at least in part from materials with high elastic modulus. Utilizing material with high elastic modulus may minimize transmission losses along the load paths of the suit due to the materials stretching. Minimizing transmission losses and securing different components of the soft exosuit system may reduce power consumption, motor size, and battery size. Additionally, minimal stretching may further assist in securing components of the soft exosuit system (e.g., anchor member 210) in place, thereby helping to maintain proper alignment of soft exosuit 200 on the wearer's body.

Embodiments of the soft exosuit system may further include materials that provide comfort by alleviating the risk of abrasion due to the interaction of stiffer, high elastic modulus materials with the body. As further described in more detail below, the exosuit may also be constructed to be closer to a unitary article of clothing rather than a complicated series of components, such as harnesses and straps, which may extend the time to change in and out of the soft exosuit system.

The various anchor members 210, in various embodiments, may be made from woven and reinforcement materials. Woven and reinforcement materials may have different strain properties in different directions, which allows for such textiles to be used to help define and reinforce load paths in place of potentially uncomfortable webbing reinforcement. The woven and reinforcement materials may be constructed to be adjustable and conformal in shape and contour so as to enhance their ability to stay in place when loads are applied.

FIG. 4A, FIG. 4B, and FIG. 48C illustrate a representative embodiment of waist anchor member 212. Waist anchor 212 may encircle the user's waist and be configured to engage the iliac crest for support. In an embodiment, waist anchor 212 may connect or attach to other components of soft exosuit 200, such as thigh anchor 214 via connection elements 222, to insure minimal migration and drifting as the body is in motion. The patterned contour of the suit provides a conformal fit that properly aligns with attachment points on corresponding components of soft exosuit 200.

Waist anchor 212, in various embodiments, may be fabricated using a variety of textile materials. The waist anchor 212, in various embodiments, may include layered materials and intricately patterned panel pieces. The back of waist anchor 212, as shown in FIG. 4B, can be composed of two or more panels of layered plain weave woven material, such as Typhoon, and may further be reinforced with strong material such as sailcloth. The front panels of waist anchor 212 may be attached at an angled side seam, and the left and right front panels of the waist belt may overlap to encircle the waist and connect with Velcro. Comfort may be maintained by alleviating areas of woven and layered textile by cutting and integrating plush, padded materials. For example, foam padding can be sewn underneath a cutout that aligns with the wearers' iliac crest. This padding can alleviate pressure and improves comfort when the system provides asymmetric loads during the gait cycle.

Referring to FIG. 4D and FIG. 4E, materials of waist anchor 212 may be arranged to provide load paths through the waist anchor 212, and to reinforce areas where loads may be introduced to waist anchor 212 from other components of soft exosuit 200. In an embodiment, reinforcement and/or other materials may be positioned where connection elements 224 join the front of waist anchor member 212 at attachment points 250, and where connection elements 222 join the side of waist anchor member 212. The materials may be arranged in a manner suitable to direct loads entering or leaving waist anchor 212 along predetermined load paths, as shown by the arrows depicted in these figures. As shown, in an embodiment, the materials may be arranged to direct these loads more vertically near an upper portion of waist anchor 212 so as to provide a natural up-and-down load on the hips. The materials can also be are oriented such that, when strained, the most stable direction is in line with the load path at which force is delivered through the suit. Each panel may be constructed with multiple layers of Typhoon and reinforced sailcloth material oriented in opposing directions to support loads introduced to waist anchor 212, and to distribute asymmetric loads across both hips.

Figure 5:
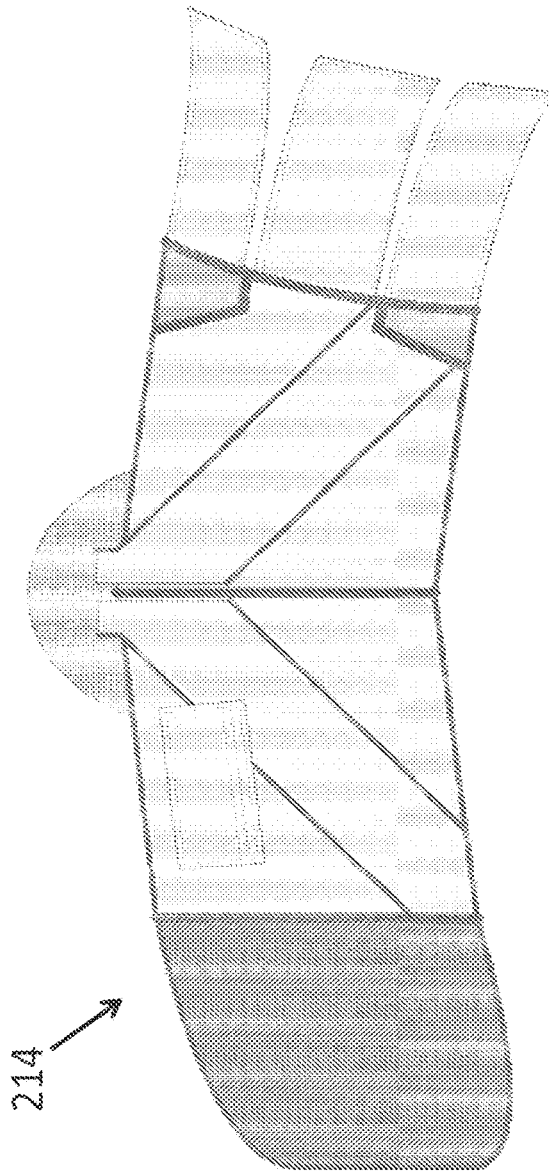
FIG. 5 illustrates a representative embodiment of a thigh anchor.

FIG. 5 illustrates a representative embodiment of thigh anchor 214. The thigh anchor 214 may include a multi-panel piece panel configured to wrap around the user's thigh. This band of material can overlap onto itself and can be secured using individual Velcro tabs, lacing, a reel and cord system or an adjustment mechanism. Thigh anchor 214 may further have a contoured design and multiple adjustable Velcro tabs, which provide for a comfortable fit that with minimal potential for slipping. Discrete elastic segment may be included along seams and or tabs and closures to improve comfort when tensioned and actuated as well as allowing a more conformal interface with the wearers' body. Several individual tabs allow for thigh anchor 214 to encircle the thigh and fasten with various amount of tension between each tab to evenly accommodate the contour of the thigh and quadriceps muscle activation. The addition of elastic alleviates pressure during actuation and as the muscle flexes and releases during movement. Thigh anchor member 214, in various embodiments, may be fabricated using a variety of additional textile materials including Typhoon, foam and reinforced sailcloth as previously described in the context of waist anchor 212. A representative placement of thigh anchor 214 may be approximately 12 centimeters above the patella over a distance of at least 15 centimeters, though one of ordinary skill in the art will recognize a number of suitable positions of thigh anchor 214 for a given application.

Referring back to FIG. 4E, thigh anchor member 214 may be constructed to distribute forces evenly to the thigh. The conformal contour of the thigh piece design stays secure on the thigh while maintaining comfort because of the flexible reinforcement material that can be patterned to interface along a load path extending between thigh anchor 214 and waist belt 212 via connection element 222. The woven and reinforcement materials may be further arranged to reinforce load paths where thigh anchor member 214 connects on the back to rear connection element 222 of the waist anchor member 212, as shown by the arrows. Materials, such as reinforcing sailcloth, may be further arranged to direct these loads more vertically near a central portion of thigh anchor member 214 so as to provide a natural up-and-down load on the thigh, as shown by the arrows depicted in this figure.

Figure 6A:
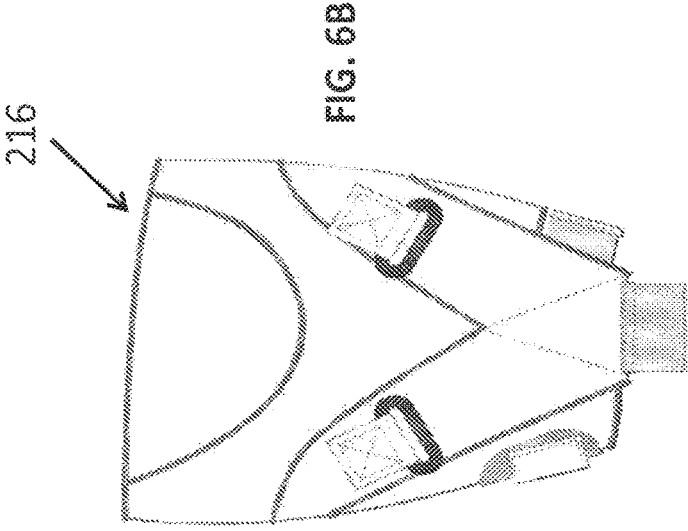
FIG. 6A illustrates a front view of a representative embodiment of calf anchor.
Figure 6B:
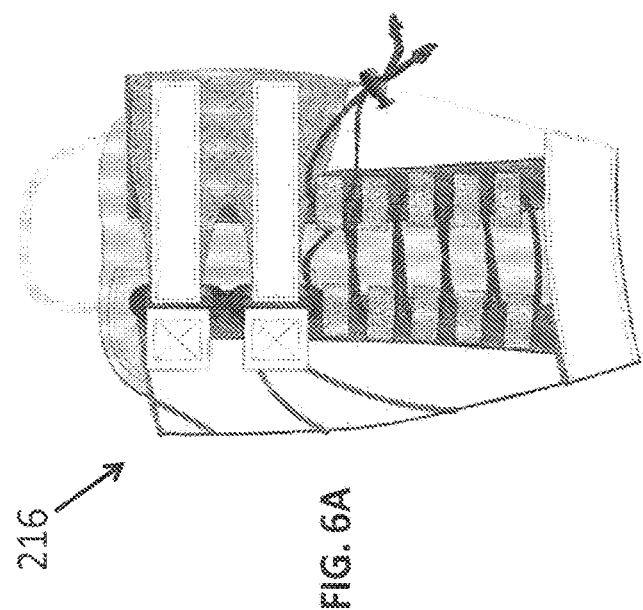
FIG. 6B illustrates a back view of a representative embodiment of calf anchor.
Figures 6E, 6F:
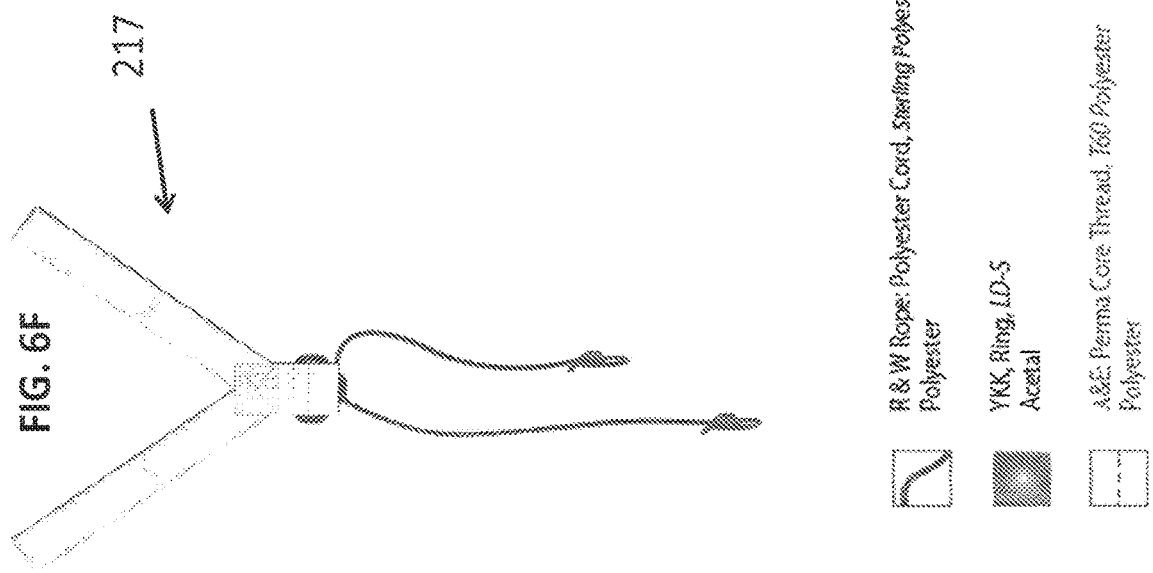
FIG. 6E depicts a front view of a representative coupling element for connecting a calf anchor with connection elements.
FIG. 6F depicts a rear view of a representative coupling element for connecting calf anchor with connection elements.

FIGS. 6A-6F illustrate a representative embodiment of calf anchor 216. Referring first to FIG. 6A, FIG. 6B, and FIG. 6C, calf anchor 216 may include a sleeve-like structure configured to securely couple with a lower portion of the user's leg, such as the calf area. A representative placement of calf anchor 216 may be approximately 7 centimeters below the center patella extending a distance of at least 18 centimeters, though one of ordinary skill in the art will recognize a number of suitable positions of calf anchor 216 for a given application.

Calf anchor 216 may be configured to moderately compress the calf muscle even without external force applied from actuation system 300. Calf anchor 216 can be reinforced with material along the load path, as previously described in the context of waist anchor 212 and thigh anchor 214, and can overlap onto itself. This sleeve may be secured using individual Velcro tabs, lacing, a reel and cord system or an adjustable mechanism. Use of these securing methods or a combination of these securing methods can accommodate the unique and varied contour of an individuals' calf while remaining stable on the wearer during actuation.

Calf anchor 216 can additionally employ foam padding to be placed under lacing that contains the bulk of the calf. This lacing can consist of inextensible laces, extensible elastic laces, a reel and cord system or an adjustment mechanism. Integrated or detachable padding can alleviate pressure caused as the system actuates from the back of the calf. Calf anchor 216 may fit comfortably and conformably due to its multi-piece patterned contoured design, double securing closure and elastic laced containment.

Referring to FIG. 6D, calf anchor member 216 may be constructed to distribute forces evenly to the user's calf region. For example, textiles may be oriented with the fabric grain in specific directions to provide a corresponding, desirable force distribution on the body. The wrap functions by the fabric "jamming" against the side of the shin and calf muscle as forces are applied downward in the back. The orientation of the reinforced material can be critical to the even distribution of inward force over the bulk of the calf muscles and tendons as the top of the shin receives mostly inward force. Calf anchor 216 may primarily consist of a woven textile oriented such that the most stable direction is in line with the load path at which force is delivered through the suit. This can be further reinforced with sailcloth material patterned on the back of the calf wrap in a "V"-shape to direct the force up and to the sides of the calf muscles and tendons. Creating an overlap on the reinforced "V"-shape can allow for an integrated point of attachment for the corresponding actuation element 220, as later described. This overlapping attachment can be further reinforced with an abrasion resistant material as the base of the attachment can rub against foot anchor 18, such as a boot, in operation.

FIG. 6E, FIG. 6F, FIG. 6G, and FIG. 6H depict a representative coupling element 217 for connecting calf anchor 216 with connection elements 224. Coupling element 217 may be referred to herein as a "Y-strap," but it should be recognized that the present disclosure is intended to include any mechanism suitable for this purpose. The Y-strap provides for some of the reaction force resulting from a tensile load applied to the foot anchor 18 to be transferred in part to the user's calf via calf anchor 216, and in part to the connection elements 224. This coupling may allow distribution of a high assistive force into two different anchor members 210 such as the calf anchor 216 and the waist anchor 212 through the connection elements 224. This coupling may also serve to reduce displacement of actuation element 320, thereby helping to minimize transmission loss within the exosuit system 100. Minimizing displacement and transmission loss in may minimize the amount of batter power required to generate a desired force via actuation system 300.

Figure 6G:
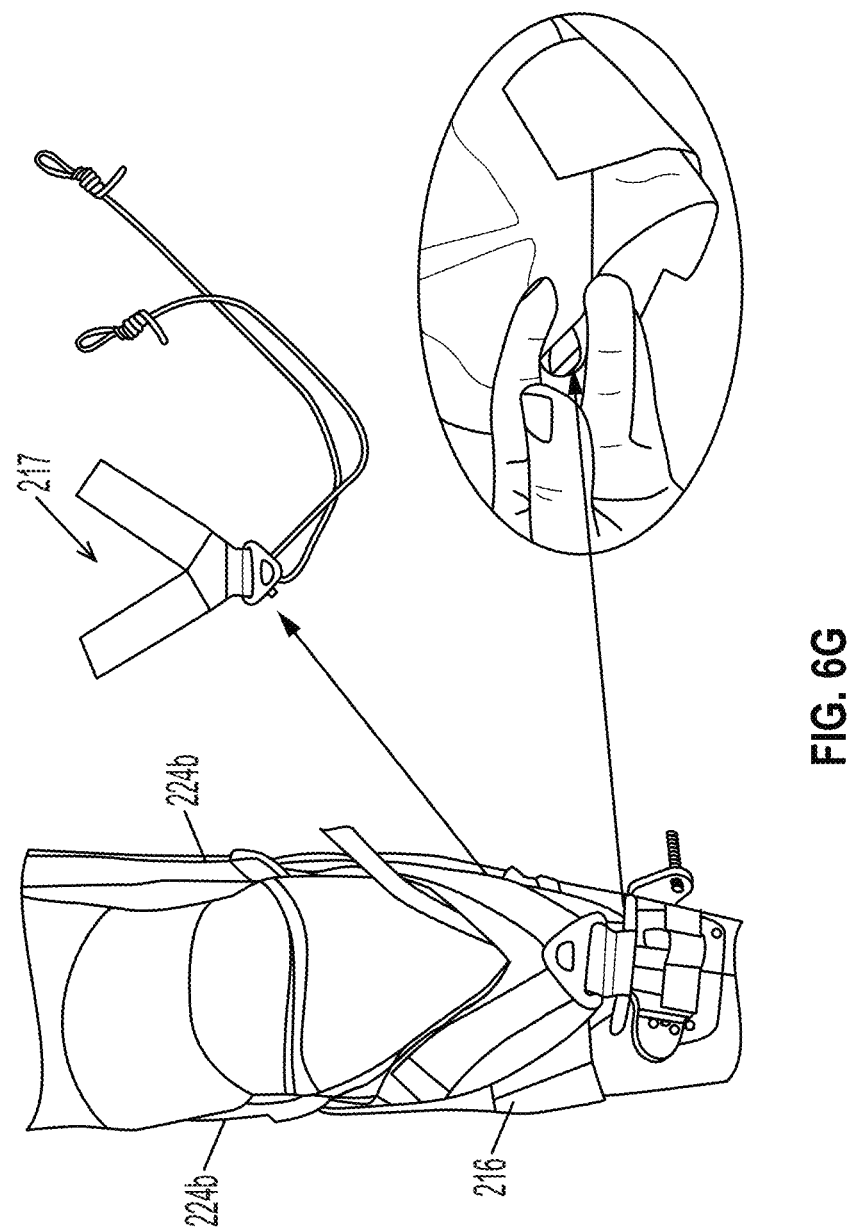
FIG. 6G depicts a representative coupling element with Y-strap and two pins inserted through the loops.

The Y-strap 217 is a custom made component that interfaces with calf anchor 216 and connection elements 224 so as to form load paths therebetween. The Y-strap 217 may be constructed of layered textile and reinforced sailcloth. The strap is composed of five individual connection points. Two of these connection points connect the Y-strap 217 to calf anchor 216. In particular, the two overlapping "V" legs of the strap can connect using Velcro to pass through two individual 2-bar slides that are affixed to the force path of the calf wrap. Because it allows two different components to sustain the total force generated by the exosuit cable, the Y-strap 217 allows to either decrease the stress on the tissues under the calf wrap and the waist belt, or to increase the maximum amount of assistive force that an exosuit can deliver without compromising the comfort of the wearer. The third connection point is used to couple the Y-strap 217 to the ends of connection elements 224a,b. In particular, there is a loop ring at the intersection of the two "V" legs of the strap, through which a cord with two loops is threaded. Each looped end of the cord may be coupled with the lower ends of connection elements 224*a,b*, which may, in an embodiment, be situated on opposing lateral sides of the user's knee joint. The fourth and fifth connection points may be loops situated near the convergence of the "V" legs of the Y-strap 217, and are used to couple the Y-strap 217 to mechanism for attaching an actuation element 320 for actuating soft exosuit 200. The mechanism, in an embodiment, may couple with Y-strap 217 via two pins inserted through the loops, as shown in FIG. 6G.

Referring to FIG. 6H, it should be noted that tensile loads may not be evenly distributed between outer and inner connection elements 224*a,b* because of asymmetries in a soft exosuit user's leg and walking mechanics. In particular, if the lower portions of connection elements 224 were coupled in a fixed position with Y-strap 219, loads may be greater in connection element 224*a* directed along the outside of the soft exosuit user's knee than in connection element 224*b* directed along the inside of the soft exosuit user's knee. This could cause uncomfortable lateral torqueing on the knee joint. As such, the cord may be allowed to slide laterally within the loop ring, thereby allowing connection elements 224*a*, 224*b* to move up and down with, as indicated by the arrows in FIG. 6H. In this way, asymmetric lateral loads exerted on connection elements 224*a*, 224*b* may be automatically balanced, thereby resulting in a self-balancing system. Of course, one of ordinary skill in the art will recognize that any number of mechanisms may be suitable for balancing uneven forces exerted by connection elements 224*a*, 224*b*, and that the present disclosure is not intended to be limited only to the exemplary embodiment described herein.

Figure 7A:
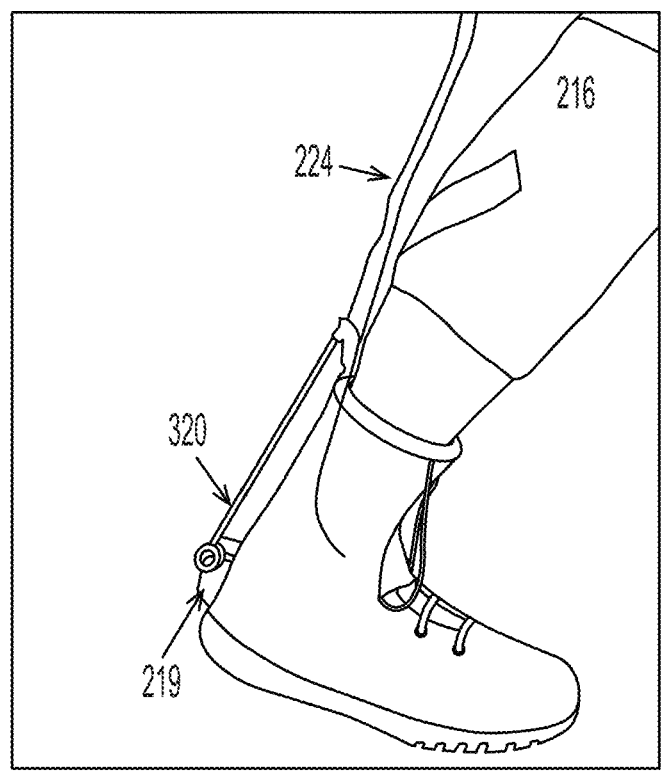
FIG. 7A illustrates an embodiment of a foot anchor member wherein the anchor member comprises a boot.
Figure 7B:
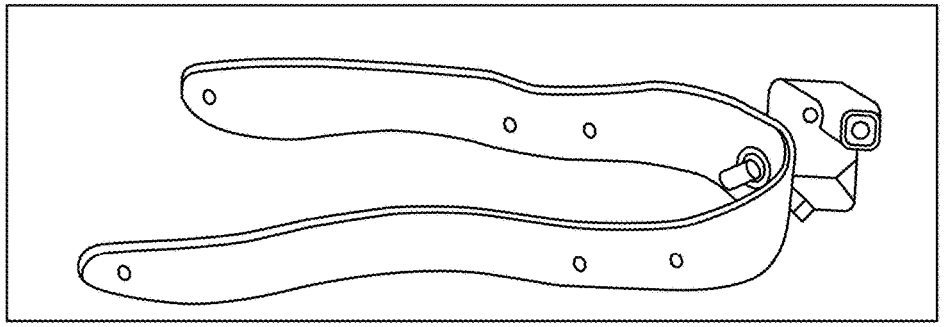
FIG. 7B depicts a representative stiffening component.
Figure 7C:
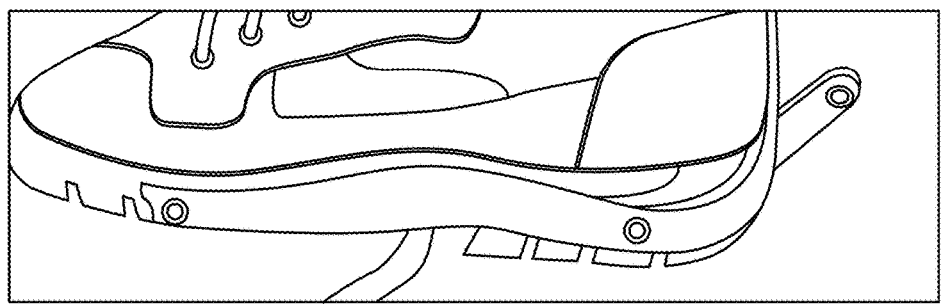
FIG. 7C shows a representative stiffening component installed on a boot.

FIG. 7A, FIG. 7B and FIG. 7C illustrate embodiments of foot anchor member 218. As shown in FIG. 7A, in an embodiment, foot anchor member may comprise footwear such as a boot. In such an embodiment, foot anchor member 218 may include an external heel coupler 219 for acting as an anchor point on the back of the boot heel. An actuation element 320 of actuation system 300 may attach to heel coupler 219 in various embodiments for delivering a tensile force to soft exosuit 200, as later described in more detail. In another embodiment (not shown), foot anchor 218 may include a footwear insert, in lieu of or in addition to an insole of standard footwear, and may serve in like manner as an anchor point on the back of the footwear heel.

In general, many forms of footwear are fairly deformable under loads. As such, when an upward pulling force acts on the anchor point at the heel of the footwear, the sole may bend upward and portions of the footwear may shift on the user's foot, potentially leading to blisters and other discomfort. Deformation may also bleed energy from forces being transmitted into or through soft exosuit 200, thereby requiring a greater amount of force to be generated by actuation system 300 to achieve a desired resulting load in soft exosuit 200.

To reduce deformation in response to loads introduced to footwear anchor 218, and thereby increase comfort and improve performance, foot anchor 218 may include a structural stiffening component. FIG. 7B depicts an example stiffening component and FIG. 7C shows the example stiffening component of FIG. 7B installed on a boot for illustrative purposes.

The stiffening component (also referred to herein as a footwear stiffener or boot stiffener) may interface with a heel section of foot anchor 218 via threaded inserts. A coarse screw may be used near the ball of the foot for its reduced cross-section and to provide additional comfort. Threaded screws daubed in flexible epoxy may also be used to provide additional stiffness. In an embodiment, the footwear stiffener may be constructed of a lightweight, strong material including, but not limited to, carbon fiber (CF). Although CF is mentioned for its relatively high stiffness to weight ratio, other materials may also be suitable for the footwear stiffener, be they metals, polymers or composites. One of ordinary skill in the art will recognize suitable materials and constructions for a given application.

The footwear stiffener, in an embodiment, may be contoured to fit around the side of the sole of the boot, with some additional space left in select areas to improve comfort, such as the arch of foot. The stiffener layer may be secured to the boot with a number of screws, nuts, bolts and/or other fasteners, or with an adhesive material, or via any other suitable method.

The footwear stiffener improves the stiffness of foot anchor 218 by increasing the effective stiffness of the sole. Because the CF is much stiffer than the sole of the footwear, the CF takes the majority of the load and deforms very little. This means that there is little or no deformation of foot anchor 218 at least between the ball of the foot and the heel, similar to rigid mountaineering boots. In this way, the footwear stiffener increases system efficiency by increasing the stiffness of foot anchor 218, which may result in needing a smaller magnitude if actuation (e.g., a lower cable stroke, as later described) to achieve the same force. For example, tests have shown that the amount of stroke required to generate 450N of force in soft exosuit 200 may be reduced by about 560% using the footwear stiffener. The reduced stroke means lower speeds, which leads to lower power consumption as the actuator 210 (e.g., motor) is required to move less to achieve the desired force. Power consumption is defined using equation (1):

$$P(W)=F(N)v(ms-1) \qquad (1)$$

where power consumption is represented by P(W), force is represented by F(N) and velocity is represented by v. Based on equation (1), when the force remains constant and the velocity decreases, the drive motor may generate less power.

Figure 7D:
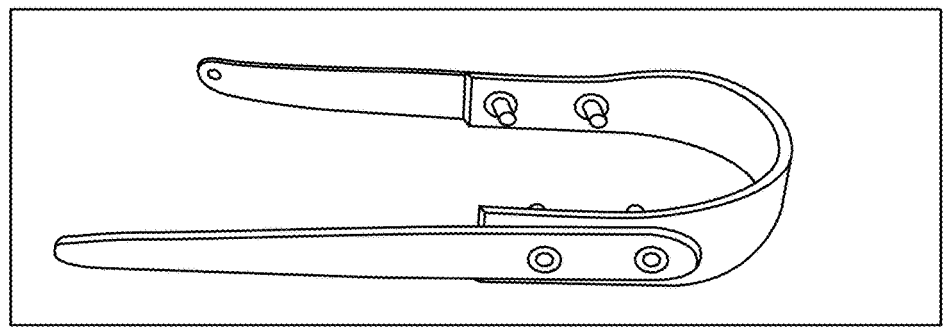
FIG. 7D depicts an embodiment of a footwear stiffener.

FIG. 7D depicts another embodiment of footwear stiffener comprising components may from a variety of materials. As shown, footwear stiffener of FIG. 7C includes aluminum spars that extend from the heel to the tarsal-metatarsal joint of the foot, and a carbon fiber cup that extends about the heel. In an embodiment, the carbon fiber cup component may have a thickness of about 2 mm to 4.5 mm. Use of a combination of aluminum and carbon fiber materials may improve the durability of the boot stiffener and provides for enhanced stiffness and comfort.

FIG. 8A, FIG. 8B, and FIG. 8C illustrate various perspectives of a representative embodiment of connection element 220. Connection elements 220, in various embodiments, may be fabricated using a variety of textile materials including layers of reinforced sailcloth material, which can be oriented and assembled such that their overlap can create the connection point, or integrated a loop for system attachment. The oriented in its most stable direction and is in line with the load path at which force is delivered through the suit eliminates the possibility of an interruption in stiffness transitioning from textile to another component. Padding can be added between the integrated attachment loop and the wearer's body so that movement during actuation causing the cable attachment component to press into the wearer's body cannot be felt.

The connection elements 220 can be made dimensionally stable using layered reinforcement sailcloth that feeds through 2-bar slide attachment points on the waist belt while the other end of the connection elements 220 include D-rings that allows the cord of the Y-strap, "cable guide" to pass through completing the load path between the waist belt and calf wrap.

Figure 9A:
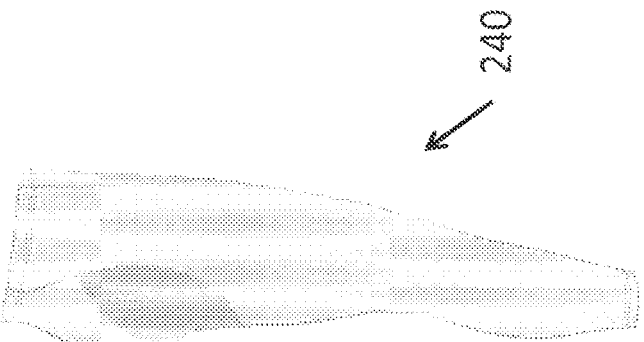
FIG. 9A illustrates a front view of an embodiment of a base layer.
Figure 9B:
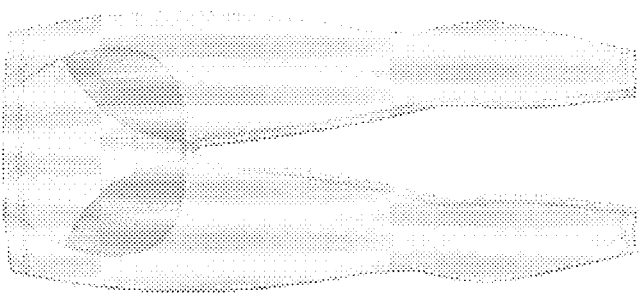
FIG. 9B illustrates a rear view of an embodiment of a base layer.
Figure 9C:
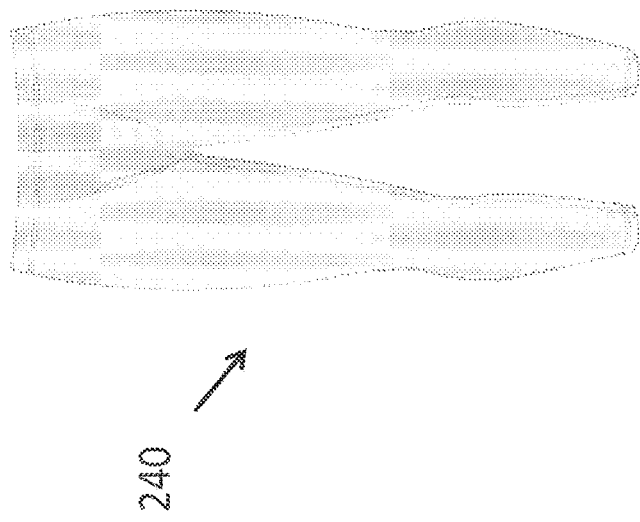
FIG. 9C illustrates a side view of an embodiment of a base layer.

FIG. 9A, FIG. 9B, and FIG. 9C illustrate embodiments of a base layer 230 (e.g., leggings) of soft exosuit 200. In various embodiments, base layer 230, as well as other components of soft exosuit 200, may include light weight, breathable and antimicrobial materials. Table 1 below provides a general description of various materials from which base layer 230 may be fabricated in various embodiments, and potential benefits associated with these materials.

TABLE 1

| Material Type | Benefits of the Material |
| --- | --- |
| Main Body Fabric, Woven: Typhoon Black 385 Manufacturer: Springfield Content: Polyester/Cotton | Finish: Durable Water Repellent Properties: Lightweight, Durable, Dimensional Stability, fire resistant coating can be applied |
| Reinforcement Material: Laminated Sailcloth, CZ90HP Manufacturer: Dimension Polyant Content: Woven/Film/Scrim/Film | Properties: Extremely light weight, Flexible, Dimensional Stability and stiffness |
| Main Body Knit: Triple Plated Jersey Stretch Knit, 64644F Manufacturer: United Knitting Content: Nylon/Lycra | Finish: Tuff Face (for abrasion resistance) and wicking Properties: Breathable, light weight, abrasion resistant |
| Mesh Inseam Knit: Circular Knit Mesh, 61491TF Manufacturer: United Knitting Content: Nylon/Lycra | Finish: Tuff Face (for abrasion resistance) and wicking Properties: Breathable, light weight, abrasion resistant |
| Under fly Antimicrobial Knit: Circular Knit Jersey, 75660 with Purthread Manufacturer: United Knitting Content: Polyester/Purthread lycra | Finish: Hydrophilic Properties: Light weight, antimicrobial, breathable |
| Custom Lamination Foam Padding: Dela Foam Content: Main Body Fabric, United 64644F/Dela Foam G45 (5 mil.)/Purthread | Properties: Light weight, conformal, antimicrobial |

As shown in Table 1, Typhoon is an example of woven material and laminated sailcloth is an example of reinforcement material applied to one or more components of the soft exosuit 200. Typhoon may be flexible, relatively breathable, light weight, and can be further reinforced with sailcloth along desirable directions. The woven and reinforcement materials may include adjustable Velcro closure tabs, laces, or other elements to provide a custom fit. The woven and reinforcement materials may further be provided with integrated attachment points for connecting with the various connection elements and may be reinforced with sailcloth lamination to increase dimensional stability.

A foam padding material may be added in strategic areas of individual components of the exosuit where rubbing and pressure can occur over bony protrusions of the wearers' body or between attached mechanical components and the wearers' body.

In certain areas of the soft exosuit system, the legging fabric may include a mesh liner when breathability of the fabric is of concern. The legging fabric may further include padding material at one or more areas where other components of exosuit system may contact the body (e.g., at the locations of one or more of anchor components 210 and/or along all or part of an area of the body along which connection and actuation elements 220 and 320, respectively, may run.

Actuation System 300

FIG. 10 depicts a representative actuation system 300 for generating tensile forces in soft exosuit 200 for delivery to user. Actuation system 300, in various embodiments, may comprise one or more actuators 310 and actuation elements 320.

Actuator 310, in an embodiment, may include any suitable mechanism known in the art for displacing actuating element 320 in a manner that generates force in soft exosuit 200 by virtue of said displacement, such as a motor. For ease of explanation alone, actuator 310 may be referred to herein as a motor; however, it should be recognized that the present disclosure is not intended to be limited to this particular embodiment of actuator 310.

Actuating element 320, in an embodiment, may include elements such as a cable, fabric straps, webbing straps, wiring, and the like. In various embodiments, a proximal end of actuating element 320 may be coupled with motor 310, perhaps via a pulley 330 and gearbox 340 as shown, and a distal end of actuating element 320 may be coupled with one or more components of soft exosuit 200. For ease of explanation alone, actuating element 320 may be referred to herein as a cable or Bowden cable; however, it should be recognized that the present disclosure is not intended to be limited to this particular embodiment of actuating element 320.

Referring to FIG. 11, in various embodiments, motor 310 may be located distally from a portion of soft exosuit 200 to which cable 320 is attached, and cable 320 may extend therebetween. In some such embodiments, motor 310 may be located somewhere on the torso or waist of the user, such as in a backpack or fanny pack, or on waist anchor 212. In other embodiments, motor 310 could instead be positioned proximate the portion of soft exosuit 200 to which cable 320 is attached. Providing drive power locally may reduce transmission losses along cable 320, and may require a smaller driver motor 310 to generate a desired force. However, positioning drive motor 310 locally could increase the inertia of the assisted appendage, which may require motor 310 to be relatively bigger in size in order to provide a correspondingly greater force to assist movement. Various embodiments of actuation system 300 may have a variety of suitable drive motor 310 placements and sizing depending on the various applications of the soft exosuit system 100.

Figure 12A:
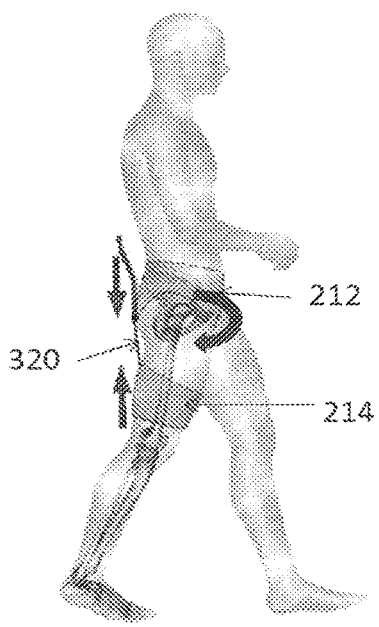
FIG. 12A illustrates an embodiment of a soft exosuit comprising a waist anchor and a thigh anchor along the rear of the thigh.
Figure 12B:
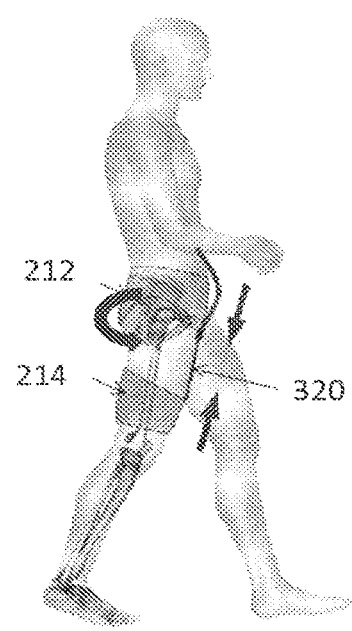
FIG. 12B illustrates an embodiment of a soft exosuit comprising a waist anchor and a thigh anchor along the front of the thigh.

Referring to FIGS. 12A-12E, cable 320 of actuation system 300 may be configured to couple with one or more components of soft exosuit 200 in a manner suitable to generate a tensile force therein. In various embodiments, cable 320 may be configured to connect to a portion(s) of soft exosuit 200 positioned on an upper portion of the user's leg. In some embodiments, the distal end of cable 320 may couple with thigh anchor 214 and an intermediate portion of cable 320 may couple with waist belt 212. For example, cable 320 may couple with rear portions of these components and extend along a rear portion of the users thigh, as shown in FIG. 12A and FIG. 12E. Additionally or alternatively, cable 320 may couple with front portions of these components and extend along a front portion of the users thigh, as shown in FIG. 12B).

In various other embodiments, cable 320 may be configured to connect to a portion(s) of soft exosuit 200 positioned on a lower part of the user's leg. In an embodiment, the distal end of cable 320 may couple with foot anchor 218 and an intermediate portion of cable 320 may couple with connection elements 224 and/or calf wrap 216, as shown in FIG. 12C, FIG. 12D, and FIG. 12E. For example, cable 320 may couple with a rear portion of foot anchor 218 and extend along a rear portion of the user's lower leg to Y-strap 219, thereby being indirectly coupled with calf wrap 216 and connection elements 224.

FIGS. 12A-12E also illustrate how actuation system 300 generates tensile forces in various embodiments of soft exosuit 200. As configured, displacement (e.g., shortening) of cable 320 by drive motor 310 may introduce a tensile force that pulls components of soft exosuit 200 towards one another, as further described below.

FIG. 12A illustrates an embodiment of soft exosuit 200 comprising waist anchor 212 and thigh anchor 214. Cable 320 of actuation system 300 has a distal end coupled with thigh anchor 214 and an intermediate portion coupled with waist anchor 212, and extends along the rear of the users thigh. Displacement of cable 320 generates a tensile force that pulls waist anchor 212 and thigh anchor 214 towards one another, as indicated by the arrows. This force, being offset from a center of rotation of the hip joint, may provide a torque about the user's hip joint in the extension direction (as indicated by the corresponding arrow), much like activation of the hamstring and gluteus maximus muscles may serve to pull the femur backwards about the waist joint.

FIG. 12B illustrates another embodiment of soft exosuit 200 comprising the same components; however, cable 320 instead extends along the front of the user's thigh. Displacement of cable 320 generates a tensile force that pulls waist anchor 212 and thigh anchor 214 towards one another, as indicated by the arrows. This force, being offset from a center of rotation of the hip joint, may provide a torque about the user's hip joint in the flexion direction (as indicated by the corresponding arrow), much like activation of the quadriceps muscles may serve to pull the femur forwards about the waist joint.

FIG. 12C illustrates an embodiment of soft exosuit 200 comprising calf anchor 216 and foot anchor 218. Cable 320 has a distal end coupled with foot anchor 218 and an intermediate portion coupled with calf anchor 216, and extends along the rear of the user's lower leg. Displacement of cable 320 generates a tensile force that pulls foot anchor 218 and calf anchor 216 towards one another, as indicated by the arrows. This force, being offset from a center of rotation of the ankle joint, may provide a torque about the user's ankle joint in the plantarflexion direction (as indicated by the corresponding arrow), much like activation of the calf muscles and Achilles tendon may serve to rotate the ankle downwards.

FIG. 12D illustrates an embodiment of soft exosuit 200 comprising waist anchor 212, foot anchor 218, and connection elements 224 extending therebetween in the manner (or in a similar manner) shown in FIG. 3A, FIG. 3B, and FIG. 3C. Cable 320 has a distal end coupled with foot anchor 218 and an intermediate portion coupled with connection elements 224, and extends along the rear of the user's lower leg. Displacement of cable 320 generates a tensile force that pulls foot anchor 218 and connection elements 224 towards one another, as indicated by the arrows. This force, being offset from a center of rotation of the ankle joint, may provide a torque about the user's ankle joint in the plantarflexion direction (as indicated by the corresponding arrow), much like activation of the calf muscles and Achilles tendon may serve to rotate the ankle downwards. Further, a portion of the tensile force is directed up connection elements 224 along the front of the user's thigh and towards waist anchor 212. This portion of the force, being offset from a center of rotation of the hip joint, may provide a torque about the user's hip joint in the flexion direction as indicated by the corresponding arrow.

FIG. 12E illustrates an embodiment of soft exosuit 200 including two modules—a first module including the configuration shown in FIG. 12A and a second module including the configuration shown in FIG. 12C. Displacement of cable 320a of the first module generates a tensile force that pulls waist anchor 212 and thigh anchor 214 towards one another, as indicated by the corresponding straight arrows, thereby delivering a resulting torque about the user's hip joint in the extension direction, as indicated by the corresponding curved arrow. Displacement of cable 320b of the second module generates a tensile force that pulls foot anchor 218 and connection elements 224 towards one another, as indicated by the corresponding straight arrows, thereby delivering a resulting torque about the user's ankle joint in the plantarflexion direction as indicated by the corresponding curved arrow. A portion of the tensile force is directed up connection elements 224 along the front of the user's thigh and towards waist anchor 212, thereby delivering a resulting torque about the user's hip in the flexion direction as indicated by the corresponding curved arrow. Motors 310a,b of actuation system 300, in various embodiments, may be actuated at different times to deliver assistance for corresponding joint motions.

Figure 13:
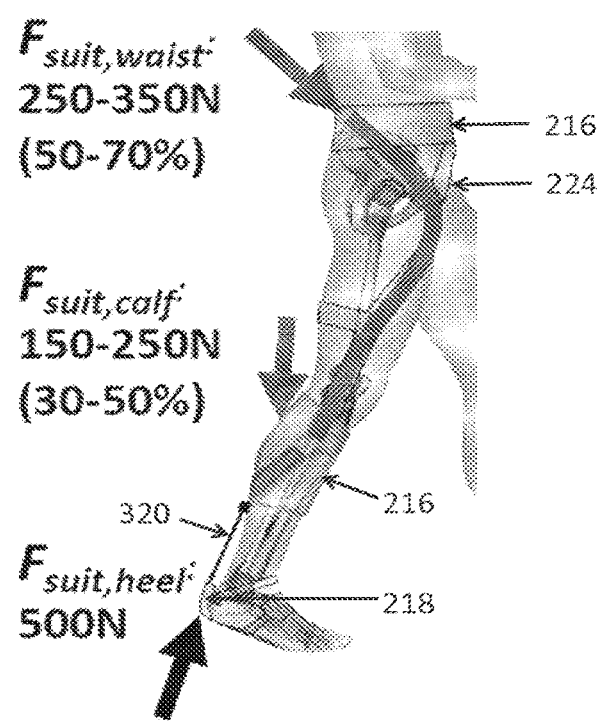
FIG. 13 depicts a soft exosuit configured to distribute portions of a force generated by an actuation system to various parts of a user's body.

Referring to FIG. 13, soft exosuit 200 may be configured to distribute portions of the force generated by actuation system 300 to various parts of the user's body. Distributing portions of the force to different parts of the user's body may serve to improve an exosuit user's comfort level and thereby allow for an increased amount of force to be generated for enhanced motion assistance, especially at the ankle. For example, say comfort limits the amount of force that could be borne by the user's waist to about 250N. Embodiments of soft exosuit 200 comprising only one anchor member 210 in addition to waist anchor 212 may be limited to about 500N of overall assistive force, if the loads are distributed evenly between the two anchors. Of course, variations in materials, construction, and fit of soft exosuit 200 may lead to an uneven distribution, but for the sake of the current example, assume a 50%/50% distribution. Embodiments of the soft exosuit 200 further includes calf anchor 216. If forces are distributed evenly amongst these three anchor elements, the result is about a 33%/33%/33% split of the overall force being delivered to the corresponding parts of the body. In the current example, that would be about 167N to each of the waist, calf, and heel of the user. As 167N falls below the hypothetical comfort threshold of 250N at the waist, the overall force that can generated in the suit may be increased by a comparable amount (i.e., to a total of about 750N). It should be recognized; however, that the particular construction of the soft suit 200, and how it interfaces with the body, may affect the distribution. For example, as shown in FIG. 13, rather than an even distribution, about 30%-50% of the force generated by actuation system 300 could be distributed to the user's calf, resulting in only about 50%-70% of the actuator force being borne by the user's waist. Even still, this may allow for additional force (e.g., about 150N-250N) to be delivered to soft exosuit 200 near the ankle (e.g., for a total of 500N) whilst maintaining the same loading on the user's waist (e.g., 250-350N), as before. This extra force may be useful in providing enhanced ankle motion assistance. Additionally, distributing the force amongst multiple parts of the user's body reduces the force on each element, thereby reducing pressure on the skin and underlying tissue and improving user comfort. Other embodiments of the soft exosuit system 800 may have forces of about 300 N to about 450 N applied to the soft exosuit user's calf. It should be understood that these are purely hypothetical examples, and the specific force magnitudes and distribution percentages set forth herein are for illustrative purposes only.

The force distribution, in various embodiments, may be controlled in part by adjusting various components of soft exosuit system 200. For example, the Y-strap 219, which couples cable 220 and connection elements 224 to calf anchor 216, may be tightened down to provide a stiffer interface, thereby offloading to the user's calf a larger portion of the overall suit force. Similarly, in another embodiment, Y-strap 219 may be loosened up to provide a looser interface, thereby offloading to the user's calf a smaller portion of the overall suit force. Splitting the load between connection elements 224a,b may also serve to increase user comfort.

Sensors 400

Figure 14B:
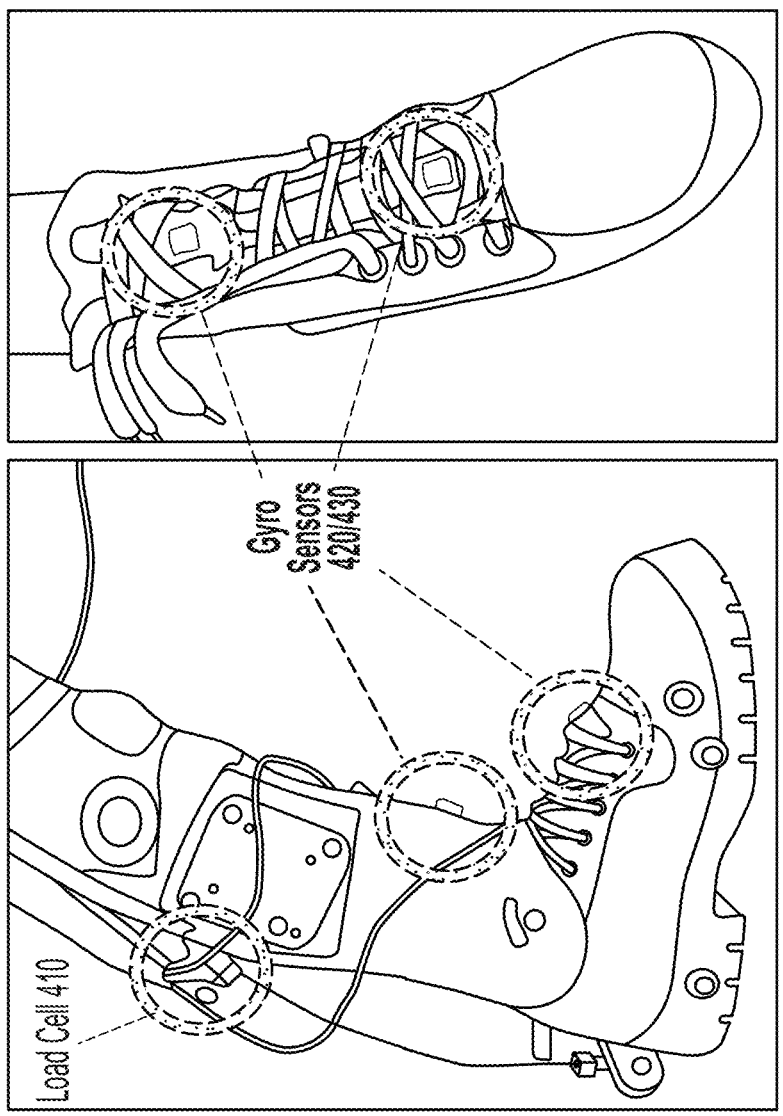
FIG. 14B depicts a force sensor positioned at an interface between connection elements and a cable.
Figure 14A:
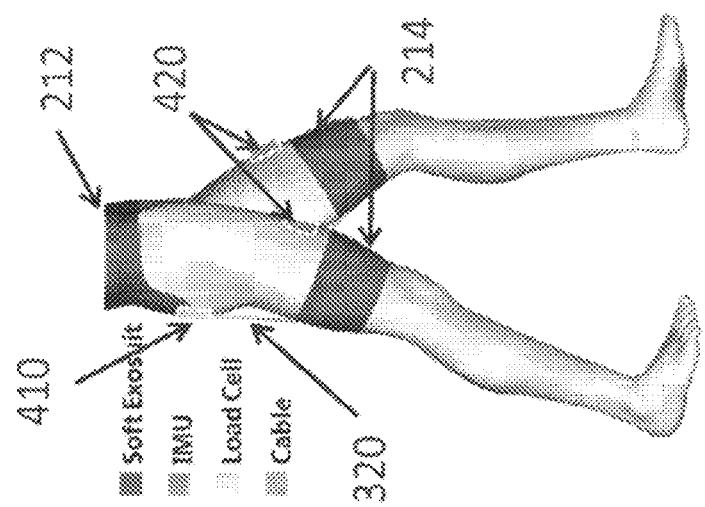
FIG. 14A depicts a force sensor positioned at an interface between a cable and a waist anchor.

Referring to FIG. 14A and FIG. 14B, exosuit system 100 may further comprise one or more sensors 400.

One or more of sensors 400, in various embodiments, may include any sensor or combination of sensors suitable for measuring tensile forces generated by actuation system 300 in soft exosuit 200 (referred to herein as a "force sensor(s) 410"). For example, in an embodiment, force sensor 410 may include a load cell. For ease of explanation alone, force sensor 410 may be referred to herein as a load cell; however, it should be recognized that the present disclosure is not intended to be limited to this particular embodiment of force sensor 410, and that any other suitable sensor/sensor arrangement capable of a similar purpose may be used instead. Force sensors 410 may be positioned in any location on or within soft exosuit 200 suitable for measuring the tensile force acting on a corresponding portion of soft exosuit 200. In an embodiment, force sensor 410 may be positioned between or proximate a junction between components of soft exosuit 200 so as to measure tensile forces exerted on one component by another. For example, referring to FIG. 14A, force sensor 410 may be positioned at an interface between cable 320 and waist anchor 212 so as to measure a tensile force exerted by cable 320 on these components of soft exosuit 200. As another example, referring to FIG. 14B, force sensor 410 may be positioned at an interface between connection elements 224 and cable 320 so as to measure a tensile force exerted by cable 320 on these components of soft exosuit 200. Of course, exosuit system may comprise any suitable number, type, and arrangement of force sensors 410 to measure tensile forces in soft exosuit 200 for any given application.

Still referring to FIG. 14A and FIG. 14B, one or more of sensors 400, in various embodiments, may include any sensor or combination of sensors suitable for measuring the motion of a body joint, such as joint orientation (i.e., angle), as well as whether the joint is rotating, in which direction, how fast (i.e., angle derivative or angular velocity), and/or whether it is accelerating. Such sensors are referred to herein as "motion sensors 420." Exemplary sensors may include inertial measurement units (IMUs), gyroscopes, and accelerometers, amongst others. Motion sensors 420 may be located on the body or on/within soft exosuit 200 in any suitable arrangement for taking such measurements. One of ordinary skill in the art will recognize that any suitable number, type, and arrangement of sensors may be utilized so long as they are capable of accurately measuring motion of the joint.

FIG. 14A is a schematic diagram illustrating an exemplary arrangement of motion sensors 420 for measuring the motion of the user's thigh. In this embodiment, IMUs 420 may be placed on the user's thighs, as shown. The IMUs 420 may be configured to measure (or calculate from other measurements taken by the IMU) one or a combination of thigh angle and thigh velocity. Thigh angle and thigh velocity may be used as approximations of hip angle and hip velocity, respectively, in circumstances where the movement of the torso is negligible in comparison with the movement of the thigh. Of course, in another embodiment, an IMU or equivalent sensor may be positioned on the user's torso, thereby providing measurements of torso motion against which to relate the aforementioned thigh motion measurements. The relative difference between the measured angles and velocities of the torso and the thigh may be used to determine the angle an velocities of the hip joint, respectively, under such circumstances.

FIG. 14B is a schematic diagram illustrating an exemplary arrangement of motion sensors 420 for measuring the motion of the user's ankle. In this embodiment, two or more gyroscopes may be used to determine the angle and velocity of the ankle joint. In particular, in an embodiment, a first gyroscope 420a may be positioned on the user's lower shin (e.g., on the shank of a boot worn by the user) and a second gyro 420b may be positioned on the user's foot (e.g., on the lower laces of a boot worn by the user). As the gyroscopes 420a,b measure the angular velocities of the foot and the shank, respectively, the rotational velocity of the ankle joint can be calculated by subtracting the measured angular velocities contained in the signals from the two gyroscopes 420a,b, similar to the way torso and thigh motion may be related to determine hip joint motion. Of course, one of ordinary skill in the art will recognize that any suitable number, type, and arrangement of motion sensors 420 may be utilized so long as they are capable of accurately measuring and/or determining the motion of the joint.

One or more of sensors 400, in various embodiments, may further include any sensor or combination of sensors suitable for detecting gait-related events such as, without limitation, a heel strike of the user, or a toe off of the user. Such sensors are referred to herein as "gait event sensors 430." In some embodiments, one or more of motion sensors 420 may be additionally configured for this role; in other embodiments, gait event sensors 430 may include a separate sensor such as foot switches, foot pressure sensors, potentiometers, and magnetometers, amongst others. Systems and methods for detecting heel strike using measurements from one or more gyroscopes and/or IMUs are explained in further detail in PCT/US2014/040340, filed May 30, 2014, which is hereby incorporated by reference herein. Gait event sensors 430 may be located on the body or on/within soft exosuit 200 in any suitable arrangement for taking such measurements. One of ordinary skill in the art will recognize that any suitable number, type, and arrangement of sensors may be utilized so long as they are capable of accurately detecting a particular gait event.

Control System 500

The present disclosure is further directed to one or more embodiments of a control system 500 configured to manage and control other components of exosuit system 100 to provide motion assistance to a user. In particular, the control system may monitor the natural, muscle-driven movement of the body in real-time and in turn, command the manner in which actuation system 300 generates tensile forces in soft exosuit 200 to deliver assistance to augment the forces generated by the muscles to move the joint and thereby reduce the metabolic cost of performing the motion. To that end, embodiments of the control system 500 may be configured to control the magnitude of assistance generated by soft exosuit 200, as well as the timing and duration for which the assistance is provided.

Referring to FIG. 15, an exemplary embodiment of control system 500 may comprise one or more data acquisition boards for receiving information from sensors 400, one or more motor controller for controlling actuation system 300, and one or more processors configured to process information received from the data acquisition board and the motor controller to manage the generation of assistance via soft exosuit 200.

Control system 500 may be configured to command the actuation of soft exosuit 200 in a manner configured to deliver power to one or more body joints of a user of exosuit system 100 to assist natural motion of those joints. In particular, control system 500 may command motor 310 to actuate cable 320 to a position suitable for generating a force in corresponding components of soft exosuit 200. The resulting torque may be applied by soft exosuit 200 as the exosuit user's body joint rotates, thereby generating additional power in the body joint to assist the natural joint motion. Stated otherwise, soft exosuit 200 may deliver assistive power according to the following equation, $P_{assist} = \tau_{exosuit} * \omega_{joint}$, where $P_{assist}$ represents the power delivered by soft exosuit 200 to the body joint, $\tau_{exosuit}$ represents the torque generated about the body joint by actuation of soft exosuit 200, and $\omega_{joint}$ represents the angular velocity of the joint during the motion being assisted.

Control system 500, in some embodiments, may be configured to actuate exosuit 200 to deliver a desired amount of power to the joint during one step or stride of the user. This may be accomplished, in an embodiment, by varying the force magnitude generated in suit exosuit 200 depending on the angular velocity of the joint motion. Such an approach may be referred to herein as "power-based force control" when the motor controller directly controls the force that the system applies to the joint to generate a desired amount of power during a step or stride depending on the rotational velocity of the joint, or as "power-based position control" when used in the context of controlling the position of the actuator to generate forces suitable for delivering the desired power to the joint during one step or stride depending on joint angular velocity. In other embodiments, control system 500 may be configured to actuate soft exosuit 200 to deliver a desired torque about the joint rather than a desired power profile. This may result in a varying amount of assistive power being delivered depending on the angular velocity of the joint during motion. Such an approach may be referred to herein as "force control" when controlling directly the force generated in soft exosuit 200, or as "force-based position control" when used in the context of controlling the position of the actuator to generate a desired force or resulting torque. While the present disclosure may describe various actuations of soft exosuit 200 in the context of only one of either power-based force/position control or force/force-based position control, it is not intended to be limited as such. One having ordinary skill in the art will recognize control system 500 may utilize any of these approaches whenever suitable.

When torque is applied in the same or similar direction as motion of the joint, a positive power may be generated. Conversely, when the resulting torque opposes the motion of the joint, a negative power is produced. Because the human body can use energy to generate both positive and negative power, both positive and negative powers generated by the exosuit may be considered assistive powers depending on the particular application. For example, positive power assistance may be desired to enhance the strength of and/or reduce fatigue associated with a particular motion of a particular joint and even the whole body. As described in more detail later in the disclosure, positive power assistance during stance plantarflexion motion of the ankle joint may help to propel the user's body forward during locomotion, such as walking, marching, running, etc. Similarly, positive power assistance during an extension motion of the hip may serve a similar purpose. As used herein, positive power, in various embodiments, may correspond to an active force applied by exosuit system to aid in said propulsion. As an additional example, negative power generated by the exosuit during the stance dorsiflexion motion of the ankle joint may be used to assist in the deceleration of the body and the body joint after heel strike prior to a propulsive motion. For example, as described in more detail later in the disclosure, this result in the system producing moments at the joints simultaneously with the underlying muscles and tendons, which extends from one heel strike to the next for a given leg. For example, in the case of ankle plantarflexion assistance, by applying force in the positive power region of the gait cycle the system assists the calf muscles and tendons to push the body up and forward. Whereas by providing assistance during the negative power phase the suit assists the calf absorb power by stretching as the body's center of mass falls downward and forward over the planted foot. In another embodiment such as hip extension the control system detects in real-time gait events to assist the hip extensor muscles from when the hip changes direction from flexion to extension which is where the positive power generation starts and when the underlying muscles start producing work in the joint to accelerate the hip joint and push the body forward as the center of mass falls downward and forward over the planted foot. The control methods described herein detect multiple gait events in real-time to detect when the underlying muscles and tendons require additional assistance to propel the body forward, this allow to adapt to the way different individuals walk and to different locomotion activities. The methods presented here may also be applied to assist joints in different directions or additional joints during locomotion and during other activities not explicitly described in present disclosure.

Control system 500 may be configured to govern the generation of assistance via commands to actuation system 300. In particular, control system 500, in various embodiments, may command motor 310 to move cable 320 to a position suitable to deliver a desired force or power to the body via exosuit 200. In an embodiment, control system 500 may command a cable position that causes cable 320 to remain slack prior to a period of passive or active assistance such that it generates little or no force in soft exosuit 200. In another embodiment, control system 500 may be configured command a cable position that causes components of soft exosuit 200 to generate a passive force in response to a particular motion. This passive force may serve to pretension cable 320 and the joint prior to a period of active assistance to enhance the effect of the active assistance. In yet another embodiment, control system 500 may command motor 310 to move cable 320 in a manner suitable to generate an active force by actively pulling components of soft exosuit 200 towards one another. Such commands are typically timed so as to move cable 320 at the onset of and/or during the motion to be assisted, so as to augment the natural forces generated by corresponding muscles. Generally speaking, the further control system shortens and increases the tension in cable 320, the higher the magnitude of the force generated within the exosuit 200 and the greater the resulting torque about the targeted body joint. Accordingly, control system 500 may be configured to control the magnitude of torque generated by exosuit system 100 by commanding drive motor 310 to move cable 320 to an position sufficient to deliver, be it passively or actively, a desired torque or power to the body joint.

Force and Actuation Profiles, Generally

Figures 16A, 16B:
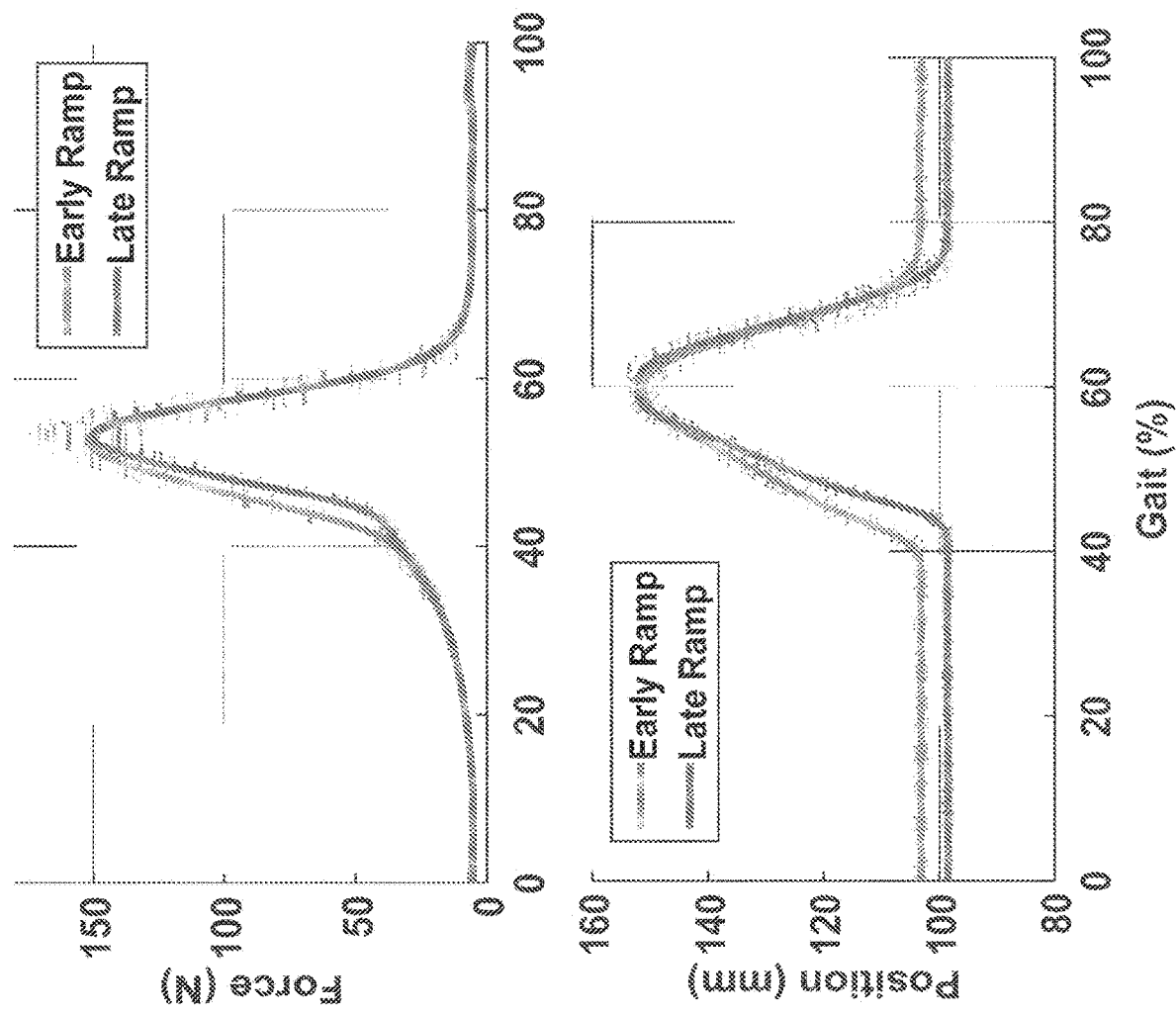
FIG. 16A illustrates a representative force profile to be delivered to a user's body via a soft exosuit.
FIG. 16B illustrates a representative actuation profile for generating a force profile.

FIG. 16A illustrates a representative force profile to be delivered to a user's body via soft exosuit 200 to assist joint motion. As used herein, a force profile is a way of conveying how much force is generated in soft exosuit 200 at various times throughout a motion assistance period. To that end, a force profile may convey the magnitude of the generated force, the timing at which it is initiated, and the duration for which force is applied. Embodiments utilizing force-based control may directly target a given force profile, while those utilizing power-based control may first utilize angular velocity measurements from motion sensors 420 to derive a corresponding force profile from a desired power profile.

The magnitude of the force in the representative force profile of FIG. 16A may increase at the start of assistance and rise sharply towards a peak magnitude. The force may then peak and subsequently fall off at a similar rate near the end of assistance. In an embodiment, the force profile may be generated such that that the force peaks when targeted muscle groups involved in generating the motion reach maximum activation levels, thereby providing a critical boost that enhances maximum power and reduces metabolic energy consumption. As described in additional detail later in this disclosure, the force profile depicted in FIG. 16A may be used to assist the lower leg muscles in assisting stance dorsiflexion and plantarflexion motion of the ankle joint to help propel the user forward during locomotion.

It should, of course, be recognized that control system 500 may be configured to command the actuation of soft exosuit 200 in any suitable manner to produce any number of suitable force profiles, and that the present disclosure is not intended to be limited to only the exemplary embodiment described above.

FIG. 16B illustrates a representative actuation profile for generating the force profile of FIG. 16A. As used herein, an actuation profile is a way of expressing how actuation system 300 may be actuated in order to generate a desired force or power profile with the appropriate timing and duration to assist the motion of the joint as it occurs.

As shown in FIG. 16B, an actuation profile may express a sequence of various cable positions throughout the period of assistance. In this example, cable 320 is maintained at a first position (i.e., 100 mm) for a portion of the user's gait cycle extending between about 80% of one gait cycle and about 40% of the successive gait cycle. During much of this period, the commanded cable position generates little or no force, as evidenced in the force profile of FIG. 16A, and cable 320 may be slack. However, during the period extending between about 20% and 40% of the gait cycle, force increases while cable position remains in the first position. This reflects a passive force being generated as the soft exosuit 200 acts to restrict the particular motion of the joint during this time. Between about 40% and 75% of the gait cycle, cable 320 is driven towards a second position (i.e., 150 mm) and back to the first position, creating the active force shown by the spike in FIG. 16A. It should be recognized that the preceding example was described for illustrative purposes only, and that control system 500 may be configured to generate any number of suitable actuation profiles in accordance with the teachings of the present disclosure.

Control system 500, in various embodiments, may be configured to utilize feedback from sensors 400 to determine appropriate cable positions, as well as the timing and duration for which they should maintained, so as to generate a desired force or power profile in soft exosuit 200, as described in more detail below.

Actuation Magnitude

The control system, in various embodiments, may be configured to determine a suitable cable position $Pos_{peak}$ for generating the desired peak force $F_{peak}$ in a soft exosuit system.

In one embodiment, control system may estimate the corresponding cable position $Pos_{peak}$ using empirical data from prior testing of soft exosuit system. For example, control system 500 may include a lookup table, library, equation, or other predetermined reference that associates various cable positions with associated forces to be produced in the soft exosuit system. While such an approach may work well with a wearable robotic system that is configured to fit various users in the same way every time they don the suit, components of soft exosuit system may shift, stretch, or otherwise behave in a manner that reduces the stiffness of the system, resulting in a reduction in the magnitude of peak force actually delivered to the user's body the soft exosuit system for a given motor position trajectory.

To account for this, control system 500, in various embodiments, may utilize a force-based position control approach, which utilizes feedback from force sensors 410 to iteratively change cable position $Pos_{peak}$ until the targeted peak force $F_{peak}$ is achieved. Control system 500, in an embodiment, may begin by comparing the desired peak force that was to be delivered during the preceding stride to load cell measurements of the actual peak force delivered during the preceding stride. The control system 500 may then utilize this information to adjust the magnitude of the actuation profile (i.e., to adjust the commanded cable position $Pos_{peak}$) to compensate, in the following stride, for any difference between the desired and actual force delivered during the preceding stride. The actuation magnitude would increase if the actual peak force of the preceding stride failed to reach the desired peak force for that stride, and would decrease if the actual peak force of the preceding stride exceeded the desired peak force for that stride. The control system may determine a corresponding cable position according to the equation (2):

$$\text{Cable } Pos_{CurrentStride} = \text{Cable } Pos_{PrevStride} \times \frac{\text{Peak } Force_{Desired,PrevStride}}{\text{Peak } Force_{Actual,PrevStride}} \quad (2)$$

In another embodiment, control system 500 may instead adjust the force in real-time by monitoring real-time force feedback from load cells 410 and adjusting cable position in a corresponding manner in real-time.

A similar force-based position control algorithm to automatically calibrate the system to a given user. In particular, control system 500, at the outset of operation, may ramp-up the forces to the desired levels, thereby ensuring proper assistance independent of factors that may vary amongst users, such as body shape, body build, how the suit fits, individual comfort preferences, etc. Load feedback, in various embodiments, may also be used by the controller to monitor the forces being applied to other joints and to account for any asymmetries that may need to be corrected.

Additionally or alternatively, in various embodiments, control system 500 may utilize a power-based position control approach to determine appropriate cable position for delivering a desired amount of power during a full gait cycle. In particular, control system 500 may first determine an actual integral power delivered by the suit during the preceding cycle. This may be accomplished, in an embodiment, by measuring the angular velocity of the joint and the force generated in exosuit system 200 throughout the preceding cycle, and integrating the product according to the equation (3):

$$\text{Integrated Power} = \frac{\int_{t_{step\_start}}^{t_{step\_end}} \tau_{suit} * \omega_{joint} dt}{\text{step duration}} \tau_{suit} * \omega_{joint} \quad (3)$$

It should be noted that the sign to the torque produced by the actuation of exosuit 200 is known due to the fact that tensile forces alone are generated therein. Control system 500 may then compare this measured integral power to the desired integral power to be delivered during the preceding cycle. This information, in turn, may be used to adjust the cable position for the current stride in the event the integrated power delivered during the preceding stride fell short of or exceeded the desired amount of power to be applied during the preceding stride. Such an adjustment, in an embodiment, may be made according to the equation (4):

$$\text{Cable } Pos_{CurrentStride} = \quad (4)$$
$$\text{Cable } Pos_{PrevStride} \times \frac{\text{Integral } Power_{Desired,PrevStride}}{\text{Integral } Power_{Actual,PrevStride}}$$

Of course, it should be recognized that adjustments to cable position need not follow the proportional relationship shown in equation (4), and one of ordinary skill in the art will recognize other suitable relationships for iteratively adjusting cable position to deliver a desired integral power.

The power-based position control approach explained above may be used in connection with embodiments of exosuit system configured to control only one of positive or negative power assistance. In order to independently control both positive and negative power assistance, embodiments of control system 500 may utilize another power-based position control approach in which cable position is determined based on separate integrations of positive and negative power portions of the motion.

In particular, the actual power delivered by exosuit system 100 may be calculated from the measured ankle speed and the force measured by the load cell, and integrated respectively within positive- and negative-power intervals and normalized by the stride time. This can be summarized in equation (5a) and equation (5b):

$$\text{Integrated Negative Power} = \frac{\int_{t_{int\_start}}^{t_{int\_end}} \tau_{suit} * \omega_{joint} dt}{\text{step duration}} \omega_{joint} < 0 \quad (5a)$$

$$\text{Integrated Positive Power} = \frac{\int_{t_{int\_start}}^{t_{int\_end}} \tau_{suit} * \omega_{joint} dt}{\text{step duration}} \omega_{joint} > 0 \quad (5b)$$

In equation (5a) and equation (5b) it should be noted that, to calculate the Integrated Negative Power, the initial time $t_{step\_start}$ corresponds to the detection of a heel strike, while the termination time $t_{step\_start}$ corresponds to the first time at which $\omega_{joint} \geq 0$. In equation (5b) it should be noted that, to calculate the Integrated Positive Power, the initial time $t_{int\_start}$ corresponds to the termination time $t_{int\_stop}$ for the calculation of negative power, while the termination time $t_{int\_stop}$ corresponds to the time when $\omega_{joint} < 0$.

Control system 500 may then adjust the commanded position amplitude level of the cable on a step-by-step basis using the two power integration values. To control the negative and the positive power respectively, control system 500 may be configured to start pulling cable 320 at the onset of the negative power interval of the motion. By doing so, the negative power for the next stride can be controlled by adjusting the level of pretension, while the positive power can be changed by controlling the level of active force. For example, if the negative power integration during the previous stride was less than the desired, the controller would increase the holding position of the cable to increase the pretension for the next stride; on the other hand, if the actual positive power for the previous stride was greater than the desired value, the controller would reduce the amplitude of the cable position to decrease the active force for the next stride. Such an adjustment, in an embodiment, may be made according to the equation (6a) and equation (6b):

$$ActiveCabPos_{CurStride} = \quad (6a)$$
$$ActiveCabPos_{PrevStride} \times \frac{\text{Integral } Pos \cdot Power_{Desired,PrevStride}}{\text{Integral } Pos \cdot Power_{Actual,PrevStride}}$$

$$PretenCabPos_{CurStride} = \quad (6b)$$
$$PretenCabPos_{PrevStride} \times \frac{\text{Integral } Neg \cdot Power_{Desired,PrevStride}}{\text{Integral } Neg \cdot Power_{Actual,PrevStride}}$$

Both force-based position and power-based position control approaches may further provide a useful way to compensate for different fits in the exosuit (e.g., due to variations in user build), for changes in the suit during operation (e.g., suit components drifting on the body, gait modifications), and for varying friction and dampening properties in the actuating element (e.g., cable) depending on how they are routed (e.g., losses due to bending and stretching).

In yet another embodiment, control system 500 may perform "power-based force control". The control method would act similarly to what described in the previous paragraphs, but would control the force level during the pretensioning and the active phases of the gait instead than the cable position.

The control method will track a desired power profile in real-time during locomotion for a given joint. Control system may calculate in real-time the required force at the current point in the gait cycle by dividing the target power value by the speed of the joint which will be the input target to the low-level force control. The low-level control will then track the force that the system delivers to the joint by using real-time feedback from the loadcell or any other force-sensing system or force-estimation method.

Desired Peak Force or Desired Integral Power

The level of assistance, in various embodiments, may be adjusted either by the user or by the control system 500 to tailor the level of assistance to the wearer, to the application or to a combination of both factors. Examples of situations or combinations of situations in which either the user or the controller 500 would regulate the level of assistance include: tailor assistance to different users based on body mass and height, generally speaking subjects with higher mass and height will require higher assistive levels to get the same benefits. The primary activity or task to be performed by the user may be a factor in determining an appropriate force magnitude to be delivered by the exosuit system 100. For example, a user or the control system 500 may decide to regulate the level of assistance either to save battery or to use more battery when the wearer needs it most. In another example, a user or the control system may decide to regulate the level of assistance either to save battery or to use more battery when the wearer needs it most. Different activities such as walking at a fast speed and walking up hill or carrying heavier loads may benefit more from higher assistance than other less strenuous activities, Moreover, level of assistance may be set to a lower value when using the device for the first time and progressively increase the magnitude as user becomes trained.

Desired peak force $F_{peak}$ may, in various embodiments, be a predetermined value set as a baseline in the control system. In an embodiment, the baseline peak force may be preset. In an embodiment, the user may be able to preselect, or select while in use, a baseline peak force. The selection process by user may be implemented such that a user directly enters a baseline peak force into control system that is preferred for a given activity or that feels comfortable to user or indirectly select a baseline peak force via selection of an operational mode (e.g., low, medium, high assistance), entry of one or more parameters (e.g., a exosuit user's weight, predefined individual settings) and/or other indirect selections.

Desired peak force $F_{peak}$ may, in various embodiments, may be influenced by biological moments acting on the joint to be assisted. For example, as body weight increases, biological moments acting on the body joints typically increase for a given activity. As such, it may be beneficial to adapt the amount of assistive peak force being applied to various joints to account for these variations in biological moments. Similarly, loads carried by the user, including that of the soft exosuit itself, may also affect biological moments and can be accounted for.

Figure 17A:
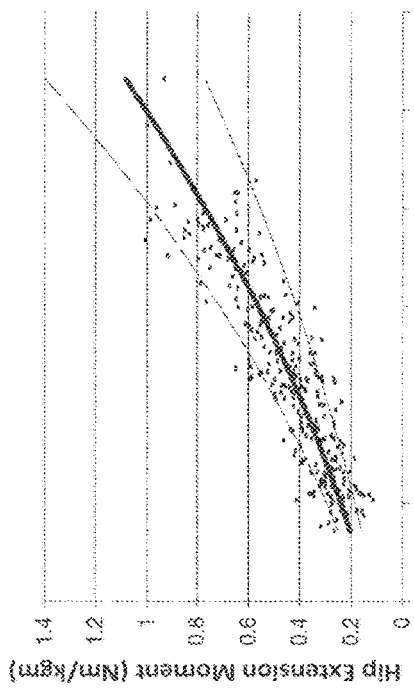
FIG. 17A is a graph comparing locomotive speed verses peak magnitude of physiological power exerted on a hip.
Figure 17B:
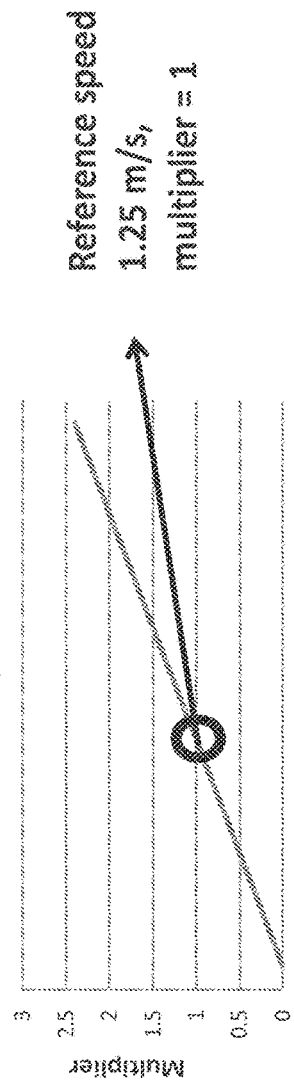
FIG. 17B illustrates that multipliers associated with hip assistance may increase substantially linearly with a walking speed.
Figure 17C:
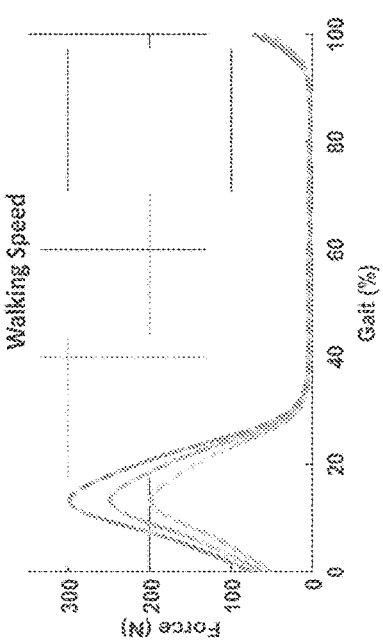
FIG. 17C illustrates some example adjusted peak forces that may be applied to a hip joint as adjusted by the multipliers of FIG. 17B.
Figures 18A, 18B, 18C:
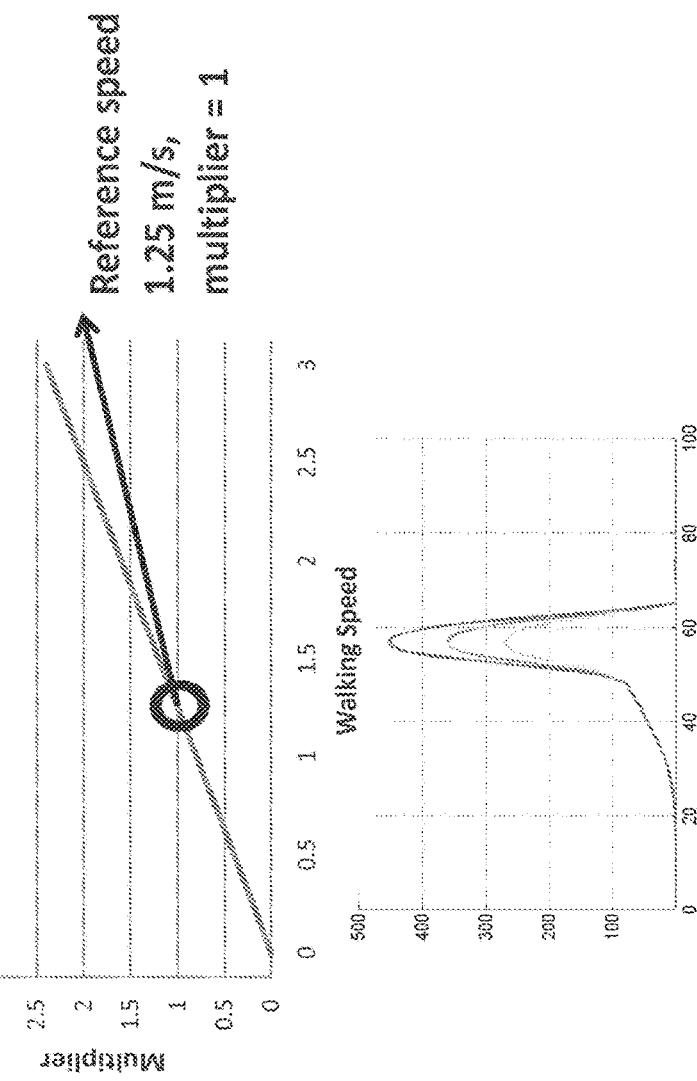
FIG. 18A is a graph comparing locomotive speed against peak magnitude of physiological power exerted on an ankle joint.
FIG. 18B illustrates that multipliers associated with ankle assistance may increase substantially linearly with a walking speed.
FIG. 18C illustrates some example adjusted peak forces that may be applied to an ankle joint as adjusted by the multipliers of FIG. 18B.

Referring to FIG. 17A, FIG. 17B, and FIG. 17C and FIG. 18A, FIG. 18B, and FIG. 18C, control system 500 may be configured to adapt the desired peak force to account for spatial-temporal factors, such as locomotive (e.g.) walking speed, that also affect biological moments acting on the joint. As shown in FIG. 17A and FIG. 18A, as locomotive speed increases, the peak magnitude of the physiological power exerted on the hip (in particular, that associated with hip extension) and the peak magnitude of the physiological power about the ankle (specifically at ankle plantarflexion) generally increase. The same is often true for spatial-temporal gait variables associated with other locomotive activities, such as running, pedaling, etc. For simplicity, the present disclosure will refer to walking speed as an exemplary spatial-temporal gait variable; however, it should be understood that the systems and methods disclosed herein for adapting assistance may be similarly applied based on other such spatial-temporal variables. For example, the systems and method disclosed herein may provide adaptive assistance for step length, stride length, walking cadence (also known as walking frequency) and other spatial-temporal variables.

Referring to FIG. 17B and FIG. 18B, adjustments can be applied, in various embodiments, in the form of a multiplier. In various embodiments, this factor may be tailored to adjust the peak assistive force or power delivered by the soft exosuit to a level proportional with the physiological moments and powers acting on the user's joint at that walking speed. As configured, exosuit system 100 may serve to substantially reduce the effect of, cancel out, and even overcome these natural forces, and thereby, reduce user fatigue, depending on the desired application. As shown in FIG. 17B and FIG. 18B, the multipliers associated with hip and ankle assistance may increase substantially linearly with walking speed, similar to the way physiological moments increase on these joints with walking speed as depicted in FIG. 17A and FIG. 18A.

Figure 19A:
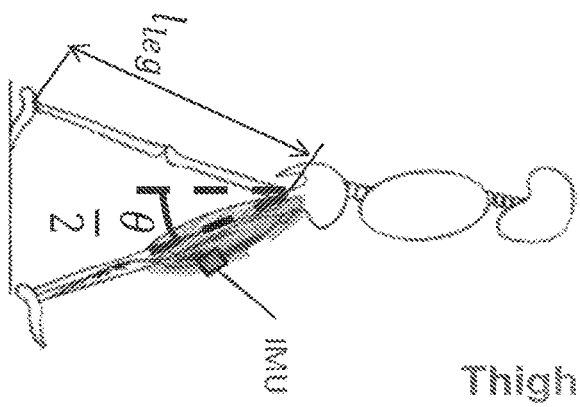
FIG. 19A depicts a hip range of motion in a sagittal plane.

The adjustment factor, in an embodiment, may be applied to the baseline peak force to be delivered by exosuit system 100 to a corresponding joint. FIG. 17C and FIG. 18C depict, for illustrative purposes only, some example adjusted peak forces that may be applied to the hip and ankle joints respectively, as adjusted by the multipliers of FIG. 17B and FIG. 18B. These graphs are based on the assumption that the control system is configured to provide a baseline peak force of about 200 N to the hip and about 350 N to the ankle, but one of ordinary skill in the art will recognize that these are just exemplary baseline forces, and that any suitable baseline force may be adjusted by any suitable spatial-temporal factor in accordance with the present disclosure. As can be seen in FIG. 17B, for example, a slower walking speed of about 0.5 m/s results in about a 0.4 hip multiplier, which reduces the baseline peak force of 200 N to an adjusted peak force of about 80 N at that walking speed as shown in FIG. 17C. Similarly, as can be seen in FIG. 18B, a slower walking speed of about 0.5 m/s results in about a 0.4 ankle multiplier, which reduces the baseline ankle peak force of about 350 N to an ankle peak force of about 140 N at that walking speed according to the ankle force profile as shown in FIG. 18C. On the other hand, at a faster walking speed of about 1.75 m/s, for example, the hip and ankle peak force modifiers may be about 1.4 as shown in FIG. 17B and FIG. 18B, which increases the respective baseline peak forces from about 200 N and about 350 N to adjusted peak forces of about 280 N and about 490 N, respectively, as shown in FIG. 17C and FIG. 18C. While the exemplary multipliers provided in FIG. 17B and FIG. 18B are depicted as increasing substantially linearly with locomotive speed, it should be recognized that multipliers need not follow a linear relationship and may be defined in any suitable manner Referring to FIG. 19A and FIG. 19B, control system 500 may be configured to estimate a locomotive speed (e.g., walking speed, running speed, etc.) of the user for use in correspondingly adjust the magnitude of the force or power profile as described above. Referring to FIG. 19A, walking speed, in an embodiment, may be estimated, in part, by using hip angle measurements determined from the IMUs. In particular, these measurements can be used to define a range of motion Θ of the user's hips in the sagittal plane, as shown in FIG. 19A. The length $l_{step}$ of the user's step can then be estimated as a function of leg length $l_{leg}$ and hip range of motion Θ in the sagittal plane, according to the following equation (7):

$$l_{step} = 2 * l_{leg} * \sin \theta/2 \qquad (7)$$

Leg length $l_{leg}$, in an embodiment, may be a constant variable that is either measured or estimated. For example, the control system 500 may assume a representative value based on the average leg length of a typical user, or may be configured such that a user may input his/her estimated or measured leg length before starting the system.

Still referring to FIG. 19A, walking speed $V_{walking}$ may then be estimated as a function of step length $l_{step}$ and step time $t_{step}$ (i.e., time passing between steps), according to the following equation (8):

$$V_{walking} = \frac{l_{step}}{t_{step}} \qquad (8)$$

Step time $t_{step}$, in an embodiment, may be measured as a time period between heel strikes or any other gait event. Referring to FIG. 19A, step time may be measured as a time period between the hip reaching a maximum flexion angle during two subsequent gait cycles. The IMUs, gyroscopes, or any other suitable sensor arrangement(s) may be configured to detect heel strike or other gait events as described above. Step time $t_{step}$ could then be calculated by subtracting the time of the previously detected heel strike or other gait event from the time of the most recently detected one. Of course, step time may be measured or estimated according to any other suitable manner known in the art.

Figure 19B:
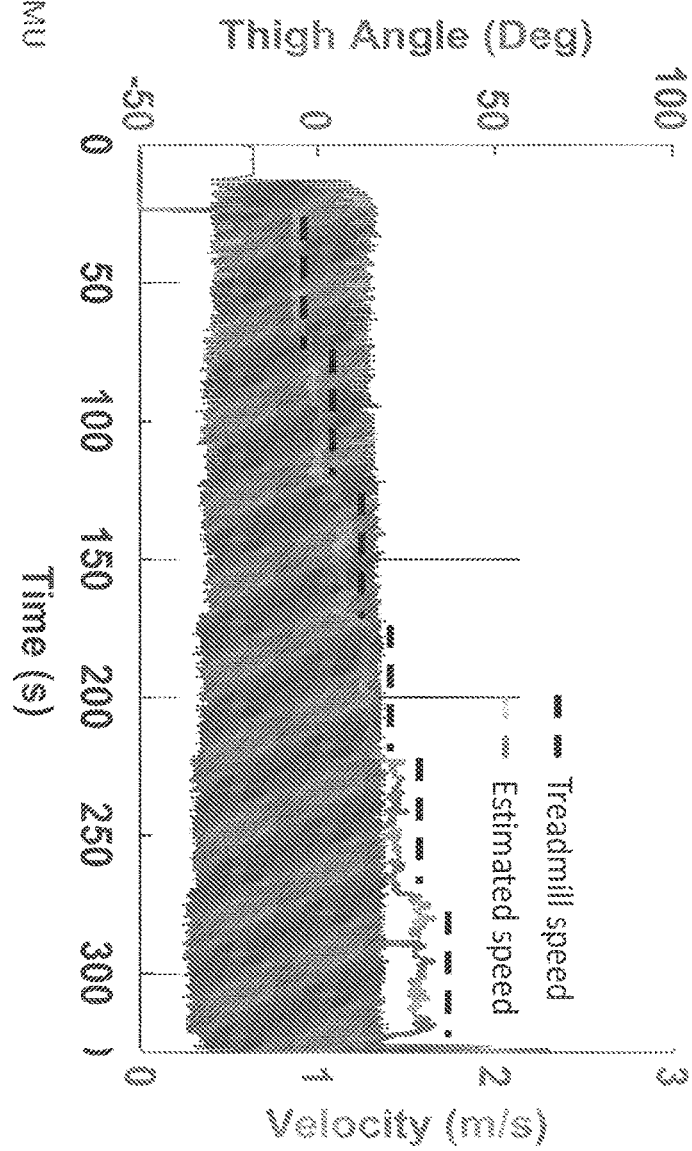
FIG. 19B illustrates a validation of a walking speed estimation.

Referring to FIG. 19B, testing was performed to validate this approach to estimating walking speed of a user. The solid line depicts the output of the speed estimation method, and the dashed line depicts walking speed as measured by an instrumented treadmill on which the user walked. As shown in FIG. 19B, the control algorithm may be able to process a number of confounding factors, such as trunk movements and changes in step length.

Of course, it should be recognized that an appropriate force magnitude to be generated in soft exosuit 200 for providing motion assistance to a user's joint(s) may be determined according to any number of factors suited to a given application, and that the present disclosure should not be limited to any one or combination of those examples listed above Assistance Timing In order to tailor assistance to the current motion of the joint and to provide a natural assistance that adapts to different locomotion activities and to the way different users walk, control system 500 may be configured to utilize inputs from various motion sensors 420 and/or gait event sensors 430 positioned on or near the body, as previously described, to determine how user moving and, in turn, determine the appropriate timing for the assistance. To that end, control system 500 may monitor in real-time measurements of joint motion and estimate the time in which the underlying muscles and tendons are performing work so as to start the assistance at the right time. Such measurements, or a combination thereof, may serve as triggers for the commencement of actuation ("initiation triggers").

Initiation triggers may vary depending on the given application or locomotive activity. In one embodiment, the detection of a particular joint movement event may serve as an initiation trigger. In particular, it may be the case that a motion to be assisted typically starts at a particular event such as when a joint angle reaches a maximum value or when the joint changes direction of movement, and thus control system 500 may be configured to interpret such a detection as an initiation trigger. In another embodiment, the detection of the joint having reached a particular angular velocity may serve as an initiation trigger. For example, in some applications, it may be desirable only to assist joint motion when the joint is moving above or below a threshold speed, as indicated by the magnitude of the measured angular velocity). In other applications, it may be desirable to provide assistance when the joint is rotating in a particular direction, as indicated by the sign of the measured angular velocity. It should be recognized that measurements of joint angle may be used in a similar manner (e.g., by calculating angle derivative and the like to yield velocity-like and/or acceleration-like measurements). In yet another embodiment, the detection of a combination of joint angle(s) and angular velocity(s) may serve as an initiation trigger. For example, in some applications, it may be desirable to provide assistance part-way through an extension motion— here the initiation trigger may be the detection of a combination of a particular angle representative of the start of the portion of the extension motion to be assisted and an angular velocity having a sign (i.e., + or −) associated with extension motion (as opposed to the opposite sign, which may be indicative of an opposite flexion motion, for example).

In some applications, it may be desired to provide assistance to the joint only when the joint motion coincides with a particular motion or combination of motions of other parts of the body, and/or with another event associated with motion of the body. For example, in various embodiments, control system 500 may be configured to increase leg joint assistance at times when the foot is in contact with the ground. In this way, assistance may be tailored to those motions serving to propel the user forward, thereby improving efficiency. In such cases, an initiation trigger may comprise, in addition to the detection of associated indications of joint motion, the detection of some indication that the foot is in contact with the ground. In an embodiment, one such detection may be that of a heel strike. Control system 500 may be configured to detect such an event from the measurements gathered from one or more of sensors 430, as later described in more detail in the context of embodiments of the control system directed to ankle assistance. Of course, if assistance is to be provided based on the motion of other joints, control system may be configured to monitor the motion of those other joints and, in turn, detect one or more triggers necessary to initiate assistance of the joint at issue.

Assistance Duration

Control system 500 may further utilize joint motion measurements to determine when to cease providing active assistance to the joint.

In various embodiments, control system may be configured to terminate assistance when the joint reaches a predetermined angle or rotational velocity. To that end, in an embodiment, control system may monitor real-time angle measurements and terminate actuation when the desired angle is reached. Similar processes may be utilized to estimate assistance duration in some embodiments featuring different triggers for terminating assistance, such as when it may be desired to terminate assistance when the joint motion ceases or changes direction. In an embodiment, control system may indirectly determine assistance duration in similar fashion by monitoring real-time rotational velocity measurements and terminating actuation when the measured angular velocity reaches zero.

The control system, in various embodiments may monitor real-time measurements of joint angle, velocity, and/or other motion-related measurements to detect gait related events and decide assistive profile as well as when motion assistance should be initiated, maintained or terminated. Control system may use this information to estimate when the underlying muscles and tendons are creating torques at the joint and to initiate the assistance at the right time.

The controller may then drive motor to a first actuated position suitable to generate the corresponding force magnitude. Control system may continue to monitor the real-time measurements of the joint motion and estimate, based on measured rotational velocity or angle derivative when the biological muscle and tendons stop providing forces to the joint in the direction where the system cable can provide actuation so that the system will become transparent (terminate actuation) and not hinder the muscles acting in the opposite direction.

Alternatively control system 500 may determine when to terminate assistance by monitoring the assistive force generated exosuit 200 to detect a change in force of a predefined value or a predefined percentage. Such a change, in various embodiments, may indicate that the joint has progressed through the motion to be assisted. For example, in an embodiment where the cable is maintained at a constant position during active force generation, forces build and/or fall off as the joint continues to move. Control system 500 may be configured to detect the change in force and terminate actuation once the force has reached a predetermined threshold so as to not interfere with subsequent motion. Such may be the case, as later described in more detail, during the stance dorsiflexion phase of ankle motion (i.e., detect a rise in pretension force applied during stance dorsiflexion and move the cable in an appropriate manner to assist the subsequent stance plantarflexion motion); the exact same effect is applicable to hip extension assistance (i.e., detect a drop off in force as the leg approaches vertical) and may be applicable to other joints.

As such, control system may identify from the desired force profile a corresponding force magnitude to be produced at each point in the joint motion, and either move the cable to a corresponding position or command a desired force. Such a control system will control when the actuation starts and ends in real-time therefore adapting to the way different individuals walk or to different activities so that assistance is provided when it will benefit the wearer and the assistance is terminated so that system doesn't generate any force in any other situation.

As further described in more detail below, control system 500 may instead be configured to estimate or otherwise predict the duration of the joint motion. The estimated duration of the joint motion to be assisted ("joint motion duration") may then, in turn, be used to determine an appropriate duration for which exosuit system 500 may be actuated to assist the joint ("assistance duration"). Such an approach may allow for control system 500 to generate, prior to commencing actuation, a suitable actuation profile according to which soft exosuit may be actuated without further need to monitor real-time measurements of joint motion to detect a termination trigger indicative of the end of the motion.

Control system 500, in other such embodiments, may be configured to utilize joint motion measurements from a preceding motion cycle to estimate the duration of an upcoming, corresponding motion in the current motion cycle. Such an approach may be particularly useful for assisting repetitive motions, such as the locomotive motions of leg joints as a user walks, runs, etc. In various embodiments, such an approximation may closely predict the duration of the current motion given the cyclical nature of the activity, and result in an actuation profile (later described) suitable closely match the desired assistance.

Consider, as an illustrative example, a walking assistance application in which control system 500 is configured to actuate exosuit 200 to help pull the leg back from a flexed position after the forward swing phase, a motion that typically spans about 30% of an average gait cycle. Control system 500, in an embodiment, may first calculate a duration of the preceding gait cycle (also referred to herein as stride time) from joint motion or other measurements taken during that preceding cycle, and then estimate the upcoming joint motion duration during the current cycle as 30% of stride time of the preceding stride time. In another embodiment, control system 500 may estimate upcoming joint motion duration in like manner; however, rather than assuming that the motion spans about 30% of an average gait cycle, control system 500 may instead determine the actual percentage over which the motion spans during a plurality of preceding gait cycles to provide a first approximation that the controller can later on correct by using real-time measurements from integrated sensors. In particular, control system 500 may be configured to utilize joint motion measurements taken during preceding gait cycles to identify when the joint motion started and ended, and then relate them to the respective stride times of those cycles to determine joint motion duration percentages for each preceding cycle. These percentages may, in an embodiment, be averaged to provide a more customized basis for estimating the duration of the joint motion to be assisted during the current gait cycle.

Stride time, in various embodiments, may be determined in any suitable manner utilizing one or more of sensors 400. In an embodiment, stride time may be calculated as the time passing between consecutive detections of characteristic events that occur each cycle. For example, control system 500 may measure, and define as stride time, the time passing between consecutive heel strikes for a given leg. As another example, control system 500 may measure, and define as stride time, the time passing between consecutive detections of maximum hip flexion or extension. Methods for detecting heel strikes and maximum flexion/extension angles are provided in more detail later in this disclosure, as well as methods for determining a time interval passing between consecutive such detections.

It should be recognized that assistance duration may be determined from such sensor measurements in any number of suitable ways for a given application, and that the present disclosure is not intended to be limited to only those illustrative embodiments set forth above.

Generating an Actuation Profile

As previously described, control system 500 may be configured to determine a desired peak force to be generated by exosuit system 100, as well as to identify when the joint motion to be assisted begins and to estimate the duration of the joint motion. In various embodiments, control system 500 may utilize this information to generate an actuation profile according to which exosuit system 100 may be actuated to deliver the desired motion assistance to the joint.

Control system 500, in various embodiments, may be configured to generate an actuation profile in advance of the start of the motion. In one such embodiment, control system 500 may estimate joint motion duration (and thus assistance duration) based on the duration of a similar motion during a previous cycle alone. On one hand, such an approach may not take into account any variation in when the joint motions started/will start within their respective cycles—that is, should the current cycle joint motion start later in the current cycle than when the previous cycle joint motion started in the previous cycle, then the estimated duration may be somewhat longer than the actual duration of the current cycle joint motion, and vice versa. On the other hand; however, such an approach may be less complex than others and potentially afford control system 500 some time to make preparations for the upcoming actuation. It should be recognized that control system 500, in another embodiment, could be further adapted to account for the aforementioned potential variations by modifying the duration reflected in the actuation profile at or slightly after the time the initiation trigger is detected.

In various other embodiments, control system 500 may be configured to generate an actuation profile at or slightly after the detection of an initiation trigger, based on an estimation of joint motion duration that takes into account the actual start time of the motion. In one such embodiment, control system 500 may estimate joint motion duration (and thus assistance duration) at this time utilizing one of the aforementioned methods, or any other suitable method.

Example Control System for Assisting Cyclical Hip Joint Motion

Figure 20:
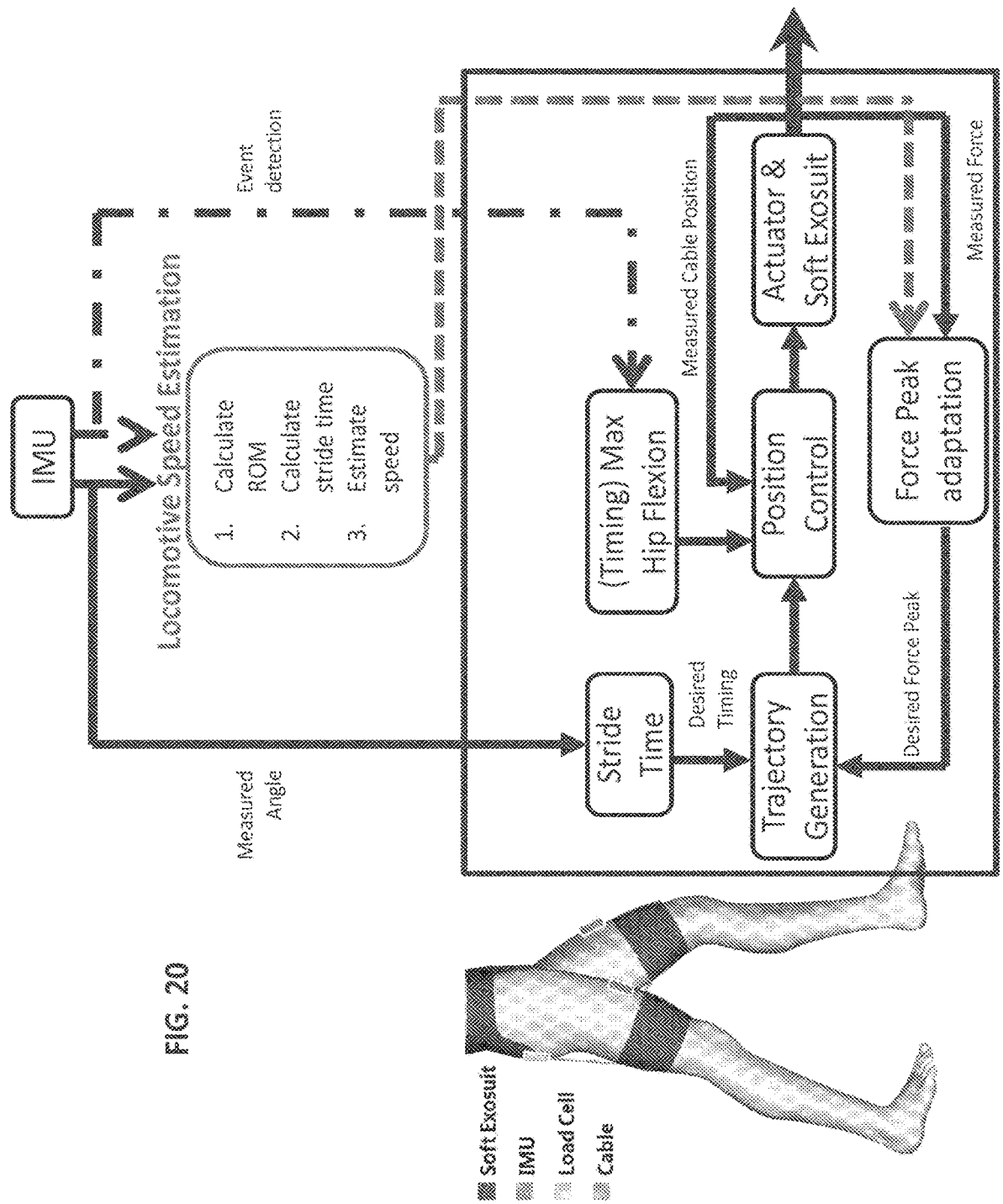
FIG. 20 is a schematic diagram of an embodiment of a hip control architecture.

FIG. 20 is a schematic diagram of an embodiment of a hip control architecture that initiates assistive torque to the hip while maintaining a robust force performance. The hip control system 600 may be configured to provide assistance to the hip joint to assist with cyclical extension motions during locomotive activities such as walking, running, and jumping. To that end, various embodiments of hip control system 600 may be used in connection with the exosuit of FIG. 12A or the first module the exosuit 200 of FIG. 12E, and with any other configuration suitable for delivering a torque to assist an extension motion of a user's hip. The hip control architecture may comprise at least portions of a soft exosuit 200, one or more inertia measurement units (IMU) or other suitable sensor 420 arrangements for measuring hip flexion and rotational velocity, one or more load cells 430, and control system 600. Pulling the cable 320 between waist anchor 212 and thigh anchor 214 of the soft exosuit 200 may generate the assistive force that creates torque about the hip joint.

In one or more embodiments, the IMU may be attached to the user's thigh (or any other suitable location for taking the prescribed measurements) and configured to measure human body motions, in particular, the thigh angle, and to estimate the hip flexion angle. Although FIG. 20 depicts the use of only an IMU, embodiments of the hip control system 600 may use other types of kinetic and/or kinematic sensors, such as potentiometers and accelerometers, and/or include additional sensors. The load cells may be force sensors 410, such as transducers, that are configured to measure tensile forces generated in exosuit 200. Embodiments of the hip control system 600 may use other types of force sensors 410 as an alternative or in addition to the load cells.

One advantage of the hip control system 600 is the ability to apply beneficial motion assistance independent of the biomechanics task at hand. Many activities, such as walking, running, jumping, and climbing stairs, share similar sequences of joint motions, and muscle groups associated with these motions may be active during similar periods. As such, many such motions share similar initiation triggers, regardless of the locomotive activity being performed.

The starting point of the biological hip extension torque can vary widely between different subjects and activities. This large variability introduced the need to determine the onset of the applied assistance to be concurrent with the onset timing of hip positive power rather than estimated based on the timing of heel strike. From a biomechanical point of view, during locomotion, hip extensor muscles start to activate slightly before the hip reaching its maximum flexion angle. From a close examination of kinetic and kinematic data of human subject data, we found that the hip joint moment reaches its maximum flexion roughly in sync with the starting point of the positive hip power. Following this rationale, we decided to use maximum hip flexion as a suitable gait event to determine the onset timing of the hip extension assistance.

Assistance, in various embodiments, may be provided when the muscles associated with a motion are most active. For example, hip extensor muscles, such as the hamstring and gluteus maximus, are typically activated in most locomotive activities to assist with an extension motion. In particular, these muscles may be most active following a preceding flexion motion, to assist with gait by pulling the user's hip over its forwardly-extended leg. As shown in FIG. 21A, in a typical gait cycle, a maximum hip flexion occurs at about 85% of the gait cycle (e.g., terminal swing of the gait cycle). The electromyography (EMG) hamstring and EMG gluteus maximus graphs in FIG. 21B and FIG. 21C illustrate the hamstrings and gluteus maximus are active after reaching the maximum hip flexion (e.g., about 91% of the gait cycle for loaded walking) and become inactive at about 30% of the gait cycle.

As such, it may be beneficial to provide assistance to the hip extensor muscles upon the detection of the hip joint having reached a maximum flexion angle, and to continue assistance until about the time in the user's gait when the hip joint has been restored to a substantially vertical angle (i.e., leg perpendicular to the ground). FIG. 22A depicts an exemplary application of force during a user's gait to assist with this motion, and FIG. 22B shows a corresponding thigh angle (relatable to hip angle, as previously described) of the user to demonstrate timing in terms of biomechanics of the leg.

To that end, in various embodiments, hip control system 600 may be configured to monitor real-time joint motion measurements to detect the start of the aforementioned hip extension motion—that is, when the hip joint reaches a maximum flexion angle. Hip control system 600 may be configured to accomplish this utilizing any of the exemplary methods previously described, or any other suitable method. For example, hip control system 600, in an embodiment, may monitor real-time measurements of hip angular velocity to detect a sign change associated with the end of a hip flexion motion and the beginning of a subsequent hip extension motion. In another embodiment, hip control system 600 may in like manner monitor real-time measurements of hip angle to detect when hip angle ceases an increase in magnitude associated with a flexion motion and begins to decrease in magnitude at the start of the subsequent extension motion. As previously noted, this may be about 85% of the gait cycle.

Hip control system 600 may be further configured to estimate a duration of the joint motion, and thus a duration for which assistance should be provided. Hip control system 600 may be configured to accomplish this utilizing any of the exemplary methods previously described, or any other suitable method. To that end, hip control system 600, in an embodiment, may be configured to estimate the current stride time of the user to estimate how long it will take for the hip joint to reach the end of the motion to be assisted, as previously described. As previously noted, the end of the hip extension motion to be assisted—that is, when the hip angle is substantially vertical to the ground—may be about 30% of the gait cycle for loaded walking overground. Stride time may be estimated, in various embodiments, utilizing stride time(s) from a preceding cycle(s). In one such embodiment, hip control system 600 may be configured to determine stride time as the time elapsed between consecutive detections of the estimated maximum hip flexion angle.

Hip control system 600, in various embodiments, may be configured to determine the desired peak force, and associated cable position for generating it, utilizing any of the exemplary methods previously described, or any other suitable method. For example, hip control system 600 may be programmed to deliver a baseline peak force of about 300N in the exosuit to assist the hip motion. This baseline force, of course, could be adjusted to account for any number of factors such as spatial-temporal factors (e.g., locomotive speed) as previously described in the context of FIG. 17A, FIG. 17B, and FIG. 17C, or user weight/loads, amongst others. Hip control system 600 may then utilize the force-based position control algorithm previously described, or any other suitable method, to determine appropriate cable position(s) for delivering the desired peak force. For example, hip control system 600, in an embodiment, may first determine the actual peak power generated in the suit during the preceding cycle, and then determine the cable position for the current cycle by multiplying the previous cycle cable position by the ratio of the currently desired peak force and the measured peak force from the preceding cycle, as per equation (2).

Additionally or alternatively, in various embodiments, hip control system 600 may then utilize a power-based position control algorithm to determine an appropriate cable position for delivering a desired integral power to the hip joint, as previously described. For example, hip control system 600, in an embodiment, may first determine an actual integral power delivered by exosuit system 100 to the hip joint during the preceding cycle as a function of the forces generated and angular velocities of the hip joint throughout the assistance provided during the preceding cycle. Then, hip control system 600 may then determine the cable position for the current cycle by multiplying the previous cycle cable position by the ratio of the currently desired integral power and the integral power measured during the preceding cycle, as per equation (4).

Figure 23A:
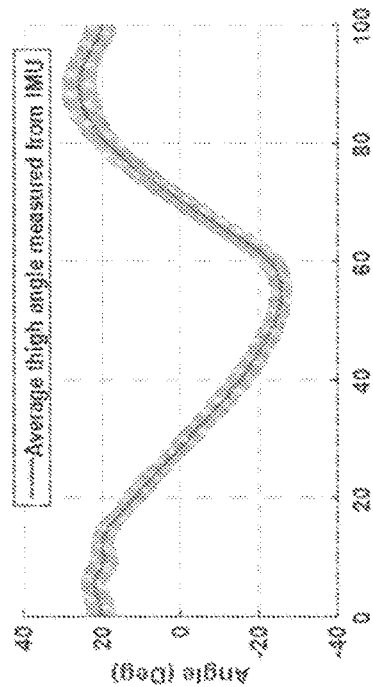
FIG. 23A depicts a corresponding representative hip angle measurement.
Figure 23B:
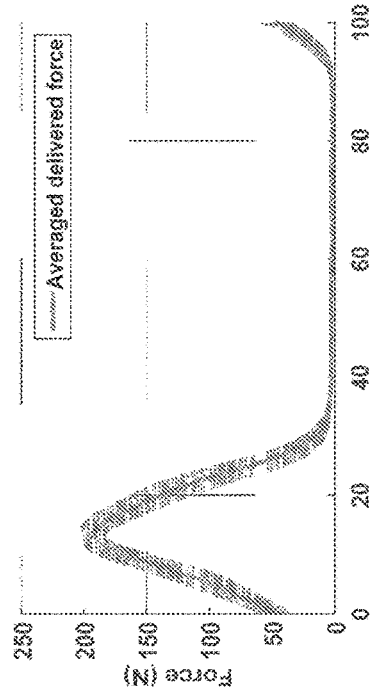
FIG. 23B depicts a representative force profiles for assisting hip joint extension motion.
Figure 23C:
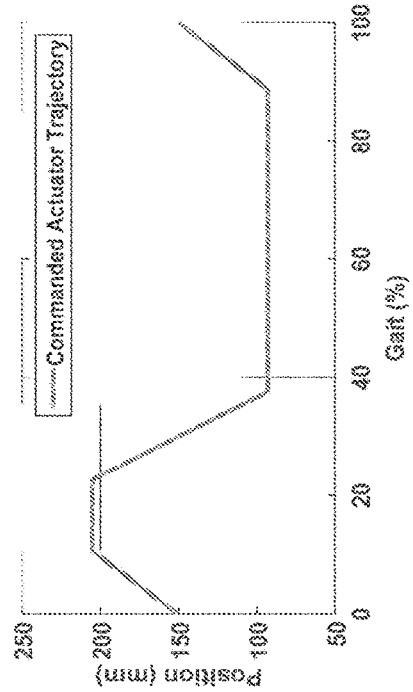
FIG. 23C depicts a representative actuation profile for assisting hip joint extension motion.

FIG. 23B depicts representative force for assisting the hip joint extension motion. FIG. 23C depicts actuation profiles for assisting the hip joint extension motion. FIG. 23A depicts corresponding representative hip angle measurements measured by the IMU.

These profiles may be generated by the soft exosuit for the hip control architecture as described regarding FIG. 20. The trajectory generation in the hip control architecture unit may be adapted to generate actuator trajectory that produces a desired force through pulling cable 320 throughout the period of assistance. The start time of the actuation (e.g., a rising edge of the trapezoidal profile) is set to the estimate maximum hip flexion angle from the IMU as previously described. In an embodiment, the magnitude of the trapezoidal profile may be modified to account for any difference in commanded magnitude and actual magnitude experienced during the previous stride, as previously described with reference to force-based position control. In particular, the hip control system 600 may monitor the maximum assistive peak force (or integral peak power) of the last stride, and adjust the magnitude of the trapezoidal profile for the current stride accordingly. The magnitude would increase if the assistive peak force (or integral peak power) of last stride did not reach the desired peak force range (or integral peak power range) and would decrease if it exceeds the peak force range (or integral peak power range). The release time of the actuation (e.g., falling edge of the trapezoidal profile) is about 40% of the gait cycle, which is calculated by the stride time unit using the last stride time detected from IMU. The trapezoidal profile may be automatically adjusted for one or more strides to adapt the environment changes and maintain the desired force performance.

Control system 600 may also generate an actuation profile using the "generateProfile" module by accounting for the stride time, measured force, and desired force. The actuator/controller unit may receive and store the measured force into memory (e.g., buffer) at pre-determined frequency (e.g., 100 Hz). Using the measured force from one more previous gait cycles, the actuator/controller unit may generate a position profile based on the duration of the previous stride time, the desired force and the previously measured force. The measured force may be based on calculating the maximum assistive peak force of the last stride.

The actuator/controller unit may implement the "generateProfile" module to correct the position amplitude of the assistive force using the measured force (e.g., position HipAmplitude=positionHipAmplitude*desired_force/measured force). In an embodiment, the "generateProfile" module may generate the position profile as a trapezoidal position profile with a specified amplitude and duration of the stride time. The falling edge of the trapezoidal position profile, or release of the actuation, may occur at about 40% of the gait cycle. As an example of a simple profile. the "generateTrapezoid" module may produce a trapezoid as the position profile with a rising edge that has a slope of "s1" at about 85% gait cycle and a falling edge with a slope "s2" at about 40% gait cycle. The falling edge of the trapezoidal position profile may be adjusted by setting the "percentageOff" variable.

TABLE 2

```
1.   global activationCurrent = FALSE;
2.   global double positionHipAmplitude =
     DEFAULT_HIP_MAGNITUDE
3.
4.   boolean isThisMaximum(angle[buffer],angle_derivative[buffer]) {
5.     if ( abs( angle_derivative [END]) < ANGLE_DER_THRESH &&
     angle_derivative[END−1] >0 )
6.       return TRUE
7.     else
8.       return FALSE
9.   }
10.
11.  double calculateMaximum(data[buffer]) {
12.    double temp_max = 0;
13.    for(i = 0; i<data.length; i++)
14.      temp_max = max(temp_max, data[i]);
15.  }
16.
17.  double[buffer] generateProfile(stride_time, measured_Force,
     desired_Force){
18.    positionHipAmplitude = positionHipAmplitude *
     desired_Force/measured_Force
19.    positionProfile[buffer] = generateTrapezoid(slope1, slope 2,
     positionHipAmplitude, stride_time, 0.4);
20.    return positionProfile;
21.  }
22.  trapezoidOutput[buffer] generateTrapezoid(slope1, slope2,
     posAmplitude, stride_time, percentageOff) {
23.    return trapezoidOutput[buffer];
24.  }
25.
26.  void loop( ) {
27.    [angle[buffer], angle_derivative[buffer]] = readHipAngle( );
28.    Force[buffer] = readHipForce( );
29.    if (activationCurrent == FALSE && isThisMaximum(angle,
     angle_derivative) ){
30.      stride_time = angle.length;
31.      measured_max_Force = calculateMaximum(force[buffer]);
```

TABLE 2-continued

```
32.        position_profile = generateProfile(stride_time,
measured_Force, desired_Force);
33.        activationCurrent = TRUE;
34.        counter = 0;
35.     }
36.     if (activationCurrent == TRUE && counter <
           position_profile.length)
{          commandHipMotor(position_profile(counter));
37.        counter = counter + 1;
38.     }
```

The acutation plot in FIG. 23C depicts the actuator activates at about 91% of the gait cycle or after reaching the maximum hip flexion, to apply a desired assistive force. Note that as stated previously since the actuation initiation is based on real-time detection of a maximum hip flexion angle, this percentage is not fixed but rather tailored to each individual or to each activity, this is a significant improvement compared to the state of the art methods that rely on a fixed actuation profile as a function of the gait cycle. The actuator continues to apply the desired assistive force until the release time of the actuation, which in FIG. 23C is about 30% of the gait cycle. Recall that the hip control system 600 may receive the thigh angle and thigh rotational velocity in real-time from sensors, such as the IMUs, and accurately apply one or more actuation profiles based on the thigh angles and thigh rotational velocities.

It should be recognized that by determining actuation timing and duration in such a manner, control system 600 may serve to avoid actuating the soft exosuit system in ways that may adversely affect the natural motion of the hip joint. Stated otherwise, embodiments of hip control system 600 may serve to ensure that assistance is only provided when the joint is actually undergoing the motion for which assistance is desired. This is a significant improvement over existing systems. For example, should the user suddenly stop prior to reaching the motion to be assisted, the initiation trigger will never be detected, and actuation will not occur. In this way, the user will not suffer from an unnecessary actuation of the suit while standing still after a sudden stop, for example. Since for soft exosuits, the system inertia and interference with joints is negligible when the system is inactive or in slack mode, i.e. when the control system pushes out cable to assure that no tension the cable, the user won't feel any perceivable forces unless the system initiates actuation. Other state of the art exoskeletons such as rigid systems, due to the significant added inertia to the biological leg would require control system to track joint movement without generating forces by using approaches such as force-control rather than staying inactive when no forces are desired to the joint to not restrict the normal motion. As another example, should the user suddenly slow down, any adverse actuation may be limited only to the duration of assistance provided—that is, the estimated assistance duration may be slightly longer than the actual joint motion duration, resulting in longer-than-actually-necessary assistance being provided for that cycle. Of course, hip control system 600 may understand that a significant change in stride time has occurred, and adjust duration for the following cycle, thereby limiting any adverse effects to the current cycle alone.

Still further, hip control system 600, in various embodiments, may be configured to detect in real-time events that may alter the timing at which assistance should be provided. One such situation may arise when the user is avoiding an obstacle in its path, such as by stepping over a rock or log. When this occurs, the user may flex its hip significantly further than it may during normal locomotion in order to clear the obstacle and step over it.

Figure 24:
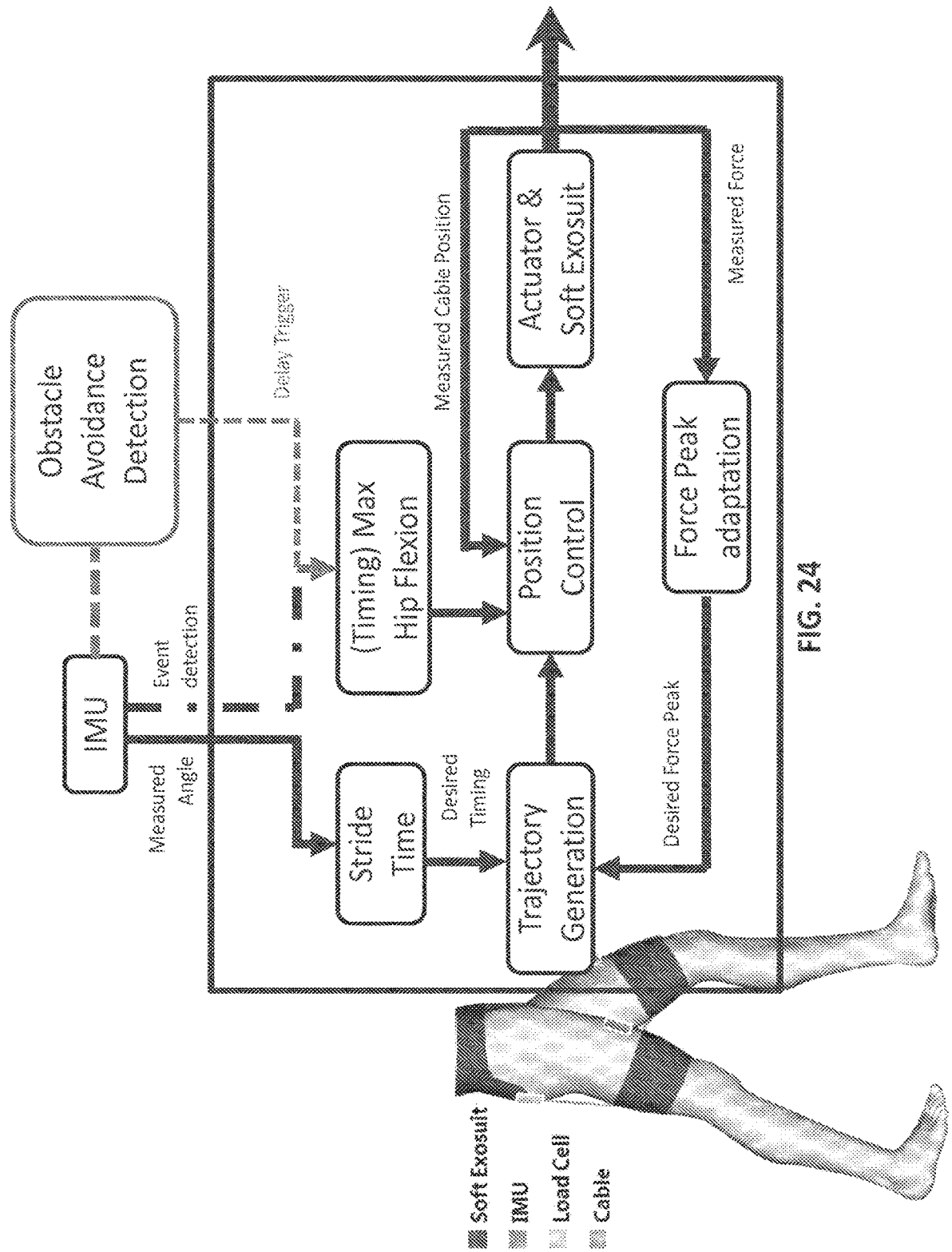
FIG. 24 is a schematic diagram of an embodiment of a hip control architecture that includes an obstacle avoidance detection unit.

FIG. 24 is a schematic diagram of an embodiment of a hip control architecture that includes an obstacle avoidance detection unit. As previously described, assistive torque may be provided to the hip as restorative force that serves to pull the thigh from a flexed (i.e., raised) state towards an extension (i.e., vertical) state. In an embodiment, the assistive torque to the hip may be applied starting from the moment of maximum hip flexion, as detected by the hip controller and/or IMU. However, it should be noted that in real-world use, the user may need to deviate from a normal walking pattern to avoid an obstacle in his/her path, such as a rock or a log. In stepping over or otherwise moving to avoid such an obstacle, the user's hip may hyperflex—that is, flex beyond the maximum flexion angle typically associated with the user's normal range of motion (ROM) while walking. In such a case, were the hip controller to initiate hip assistance at the normal time (i.e., when the typical maximum flexion angle is detected), the soft exosuit may provide this restorative force at an inopportune time—that is, while the user is hyperflexing to step over the obstacle. This may impede the motion of the user rather than assist the user's desired motion.

As such, the hip control architecture may be configured to detect such obstacle avoidance motions via measurements from the IMU, and in response, delay when hip assistance is provided in order to avoid such impedance. In particular, referring to FIG. 25A, FIG. 25B, and FIG. 25C, in various embodiments, obstacle avoidance detection may be accomplished via real-time monitoring of hip angle data collected by the IMUs versus historical hip angle data measured over a number of past steps. In particular, during normal walking, the hips will have a normal ROM in the sagittal plane, spanning between a typical maximum flexion angle of about 65 degrees and a maximum extension angle of about 140 degrees, as shown by the horizontal boundary lines surrounding the hip angle curve in FIG. 25A. The system may be configured to calculate, as a normal reference of the wearer's hip movements, a moving average of this ROM over a series of previous steps (e.g., over the previous five steps).

Hip angle data can then be monitored in real-time for motion associated with obstacle avoidance maneuvers. In particular, as the wearer pulls its knee upwards (i.e., hyperflexes its hip) to swing its leading leg over the obstacle, the measured hip angle may significantly exceed the maximum flexion angle associated with the user's normal ROM. This period of hyperflexion is depicted between about 1.5 seconds (s) and about 1.75s in FIG. 25A. Here, hip angle has exceed the flexion boundary of normal ROM by nearly 35 degrees, clearly indicating that the user is engaging in a motion that would be impeded by the application of restorative force at that time. Of course, any suitable threshold for detecting an obstacle avoidance motion and delaying the application of assistive force may be defined. In an embodiment, such a threshold may be set as a predetermined percentage by which real-time hip angle measurement must exceed the maximum flexion boundary of normal ROM. For example, obstacle avoidance adjustments may be triggered only when hip angle exceeds the normal flexion boundary by 25%. In an embodiment, such a threshold may be based on the standard deviation in maximum hip angle measurements over the past several gait cycles. For example, the obstacle avoidance algorithm may be triggered when real-time hip angle measurements exceed this standard deviation by a predetermined factor, such as two times or more. In an embodiment, the threshold may be a factor of known natural variability in a typical user's gait. For example, it is known in the biomechanics arts that a user's ROM may vary by about 3%-about 4% under normal walking conditions.

The obstacle avoidance algorithm could thus be triggered when real-time hip angle measurements exceed this variability by a predetermined factor, such as twice or more. One of ordinary skill in the art will recognize that it may be advantageous to define any such threshold as high enough to avoid false triggers, but low enough to ensure that a restorative force is not applied at a time when it may negatively affect the performance and comfort of the wearer in a significant manner. As described previously, other state of the art exoskeletons such as rigid systems would require control system to track joint movement without generating forces if an obstacle is detected by using approaches such as force-control rather than staying inactive when no forces are desired to the joint.

Figures 25A, 25B, 25C:
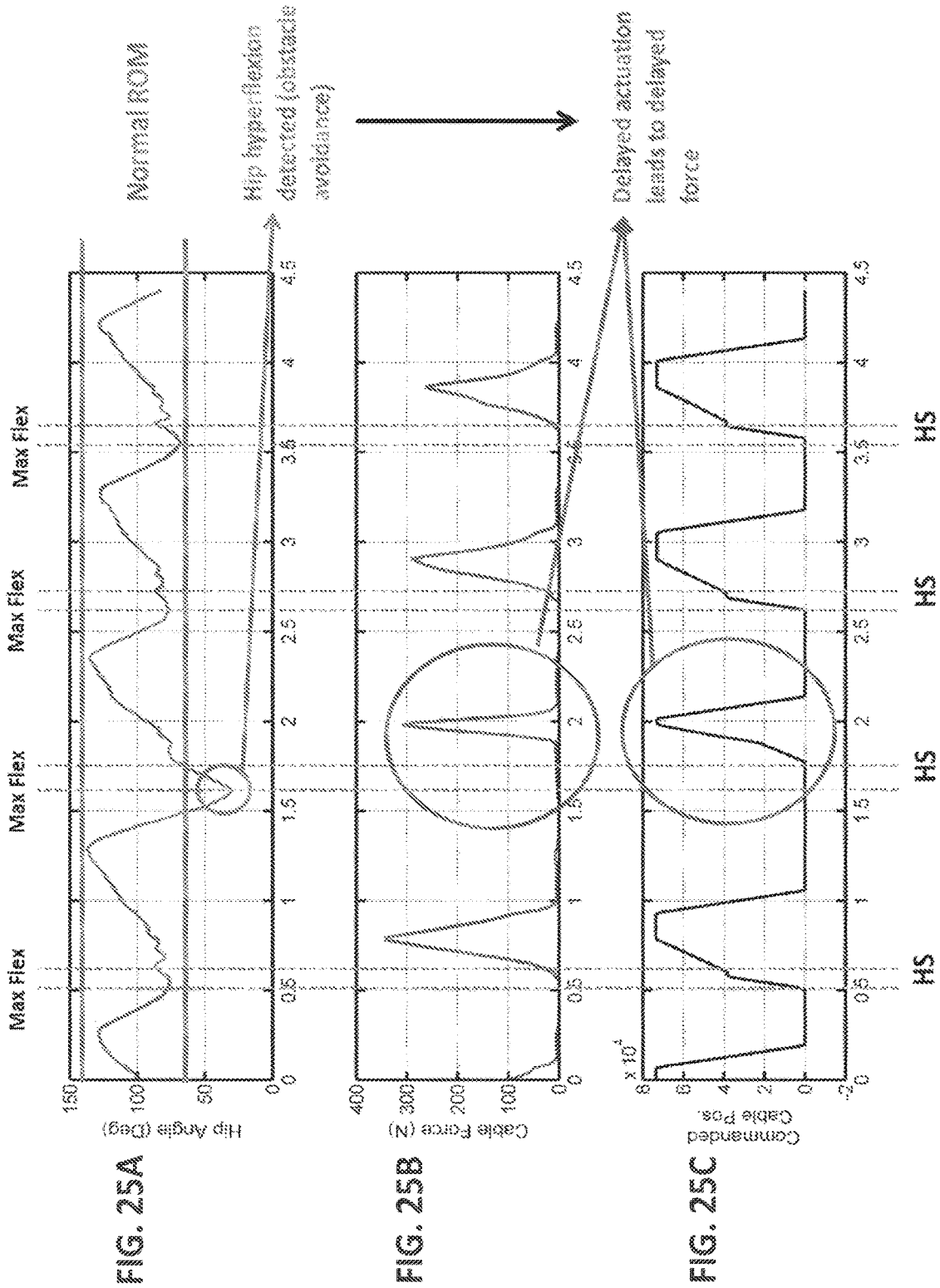
FIG. 25A is a schematic diagram of a hip angle data monitored in real-time for a hip motion associated with obstacle avoidance maneuvers.
FIG. 25B is a schematic diagram of a cable applying a force about a hip.
FIG. 25C is a schematic of a system command actuation of a corresponding hip assistance cable in a soft exosuit.

Hip assistance may be delayed for any suitable duration after the detection of an obstacle avoidance motion. In an embodiment, the system 600 may be configured to delay assistance until the hip returns within the bounds of normal ROM, as shown in FIG. 25B and FIG. 25C. In particular, referring to FIG. 25A, note that in this graph, hip angle exceeds normal ROM flexion boundary at about 1.5s. Hip angle then peaks (i.e., maximum hyperflextion) at about 1.6s, and returns within bounds of normal ROM at about 1.75s. It is at this time, when the hip angle returns within bounds of normal ROM, that the system commands actuation of a corresponding hip assistance cable (e.g., one connecting a waist belt and thigh wrap) in the soft exosuit, as shown in FIG. 25C. This, in turn, results in the cable applying a force about the hip, as shown in FIG. 25B. In an embodiment, the system may be configured to delay assistance until the corresponding leg has touched down on the far side of the obstacle being traversed. This could be determined via detection of a heel strike by the corresponding leg after hyperflexion. Such an approach, on the one hand, may provide further assurances that a restorative force is not applied at an inopportune time, but on the other hand, may delay assistance beyond a critical time when it may be desired—that is, as the wearer uses that leg to pull its body over the obstacle. Of course, the present disclosure is not intended to be limited to any particular duration for which hip assistance may be delayed upon detection of an obstacle avoidance motion.

Table 3 below is a hip control algorithm that triggers actuation at maximum thigh flexion, and stops it at the vertical thigh position. The low-level control is a position control trapezoidal profile. The magnitude, which may be the peak position, of the assistance is adjusted every step based on the peak force measured in the previous step. The timing at which the actuation starts is delayed in case of overflexion of the thigh. The magnitude of the assistive force is also adapted based on the walking speed, weight of the subject.

TABLE 3

```
1.  global activationCurrent = FALSE;
2.  global double positionHipAmplitude =
    DEFAULT_HIP_MAGNITUDE
3.
4.  boolean isThisMaximum(angle[buffer],angle derivative[buffer]) {
5.    If ( abs( angle_derivative [END]) < ANGLE_DER_THRESH &&
      angle_derivative[END-1] >0 )
```

TABLE 3-continued

```
6.      return TRUE
7.    else
8.      return FALSE
9.
10.     double calculateMaximum(data[buffer]) {
11.       double temp_max = 0;
12.       for(i = 0; i<data.length; i++)
13.         temp_max = max(temp_max, data[i]);
14.     }
15.     double[buffer] generateProfile(stride_time, measured_Force,
        desired_Force){
16.       positionHipAmplitude = positionHipAmplitude *
        desired_Force/measured_Force
17.       positionProfile[buffer] = generateTrapezoid(slope1, slope 2,
        positionHipAmplitude, stride_time, 0.4);
18.       return positionProfile;
19.     }
20.     trapezoidOutput[buffer] generateTrapezoid(slope1, slope2,
        posAmplitude, stride_time, percentageOff) {
21.
22.       return trapezoidOutput[buffer];
23.     }
24.
25.     desiredForce calculateDesiredForce(walkingSpeed, weight) {
26.       baselineForce = assistanceFactor * weight *
        physiologicalTorqueHipFlexion;
27.
28.       return baselineForce * walkingSpeed / 1.25;
29.     }
30.     walkingSpeed calculateWalkingSpeed(hipAngle, stride_time,
        leg_length) {
31.       max_theta = calculateMaximum(IMU_data.hip_angle);
32.       return 2 * leg_length * sin(max_theta) / stride_time;
33.     }
34.     void loop( ) {
35.       [angle[buffer], angle_derivative[buffer]] = readHipAngle( );
36.       force[buffer] = readHipForce( );
37.       if (activationCurrent == FALSE && IsThisMaximum(angle,
        angle_derivative) ){
38.         stride_time = angle.length;
39.         walkingSpeed = calculateWalkingSpeed(angle,
        stride_time, SUBJECT_LEG);
40.
41.         measured_max_Force =
            calculateMaximum(force[buffer]);
42.         desired_force =
        calculateDesiredForce(walkingSpeed, SUBJECT_WEIGHT)
43.
44.         if (angle > 1.3 * avgMaxHipFlxAngle ){
45.           overflxFLag = true;
46.         }
47.         else if
48.         {
49.         position_profile = generateProfile(stride_time,
        measured_Force, desired_Force);
50.         avgMaxHipFlxAngle =
            updateAverages(avgMaxHipFlxAngle, angle);
51.       }
52.
53.       activationCurrent = TRUE;
54.       counter = 0;
55.     }
56.     if ( activationCurrent ==
        FALSE && overFlxFlag == TRUE && readHipAngle( ) <=
        avgMaxHipFlxAngle) {
57.       position_profile = generateProfile(stride_time,
        measured_Force, desired_Force;
58.       activationCurrent = TRUE;
59.       counter = 0;
60. }
61.       if (activationCurrent == TRUE && counter <
        position_profile.length) {
62.         commandHipMotor(position_profile(counter));
63.         counter = counter + 1;
64.     }
```

While the preceding description is discussed in the context of providing assistive hip torque via forces associated with activation of the gluteus maximus and hamstring, it should be recognized that a similar control system may be provided for providing assistive hip toque via forces associated with activation of other leg muscles, such as the quadriceps, in like manner.

In various embodiments, the control system may be configured to utilize hip angle and rotational velocity measurements to provide assistive torque during periods when the quadriceps are active (albeit in an opposite direction, perhaps by actuating a Bowden cable directed along the front of the thigh rather than the rear as described in the context of FIG. 12B).

Example Control System for Assisting Cyclical Ankle Joint Motion

Figure 26:
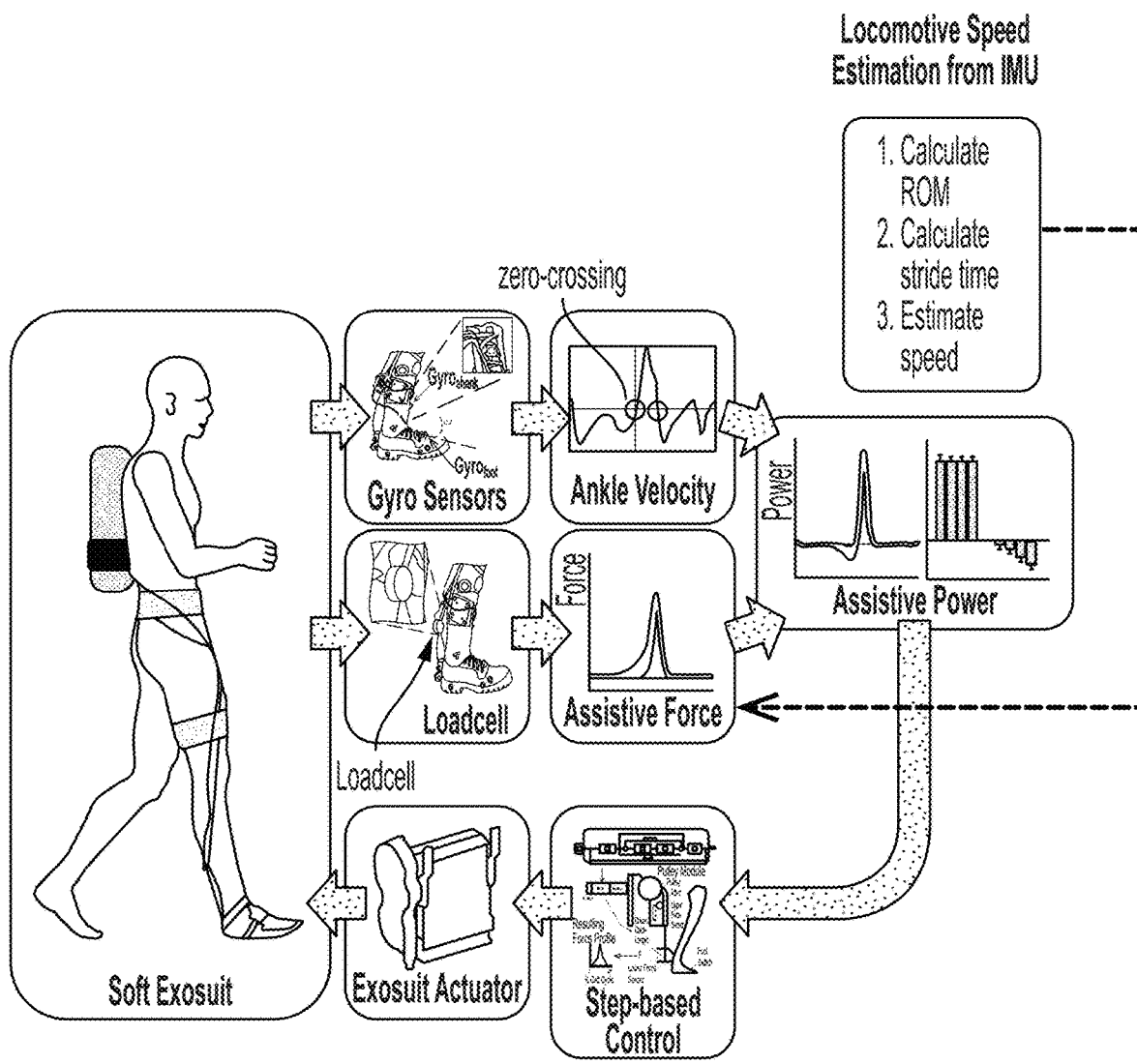
FIG. 26 is a schematic diagram of an embodiment of an ankle control system.

FIG. 26 is a schematic diagram of an embodiment of an ankle control system 700 that assists the ankle joint during locomotion while maintaining a robust performance. The ankle control system 700 may be configured to provide assistive torque to a user's ankle to assist with cyclical ankle plantarflexion motions during locomotive activities such as walking, running, and jumping. To that end, various embodiments of ankle control system 700 may be used in connection with exosuit systems of FIG. 12C, FIG. 12D, and FIG. 12E, as well as with any other configurations suitable for assisting a plantarflexion motion of a user's ankle.

Figure 27:
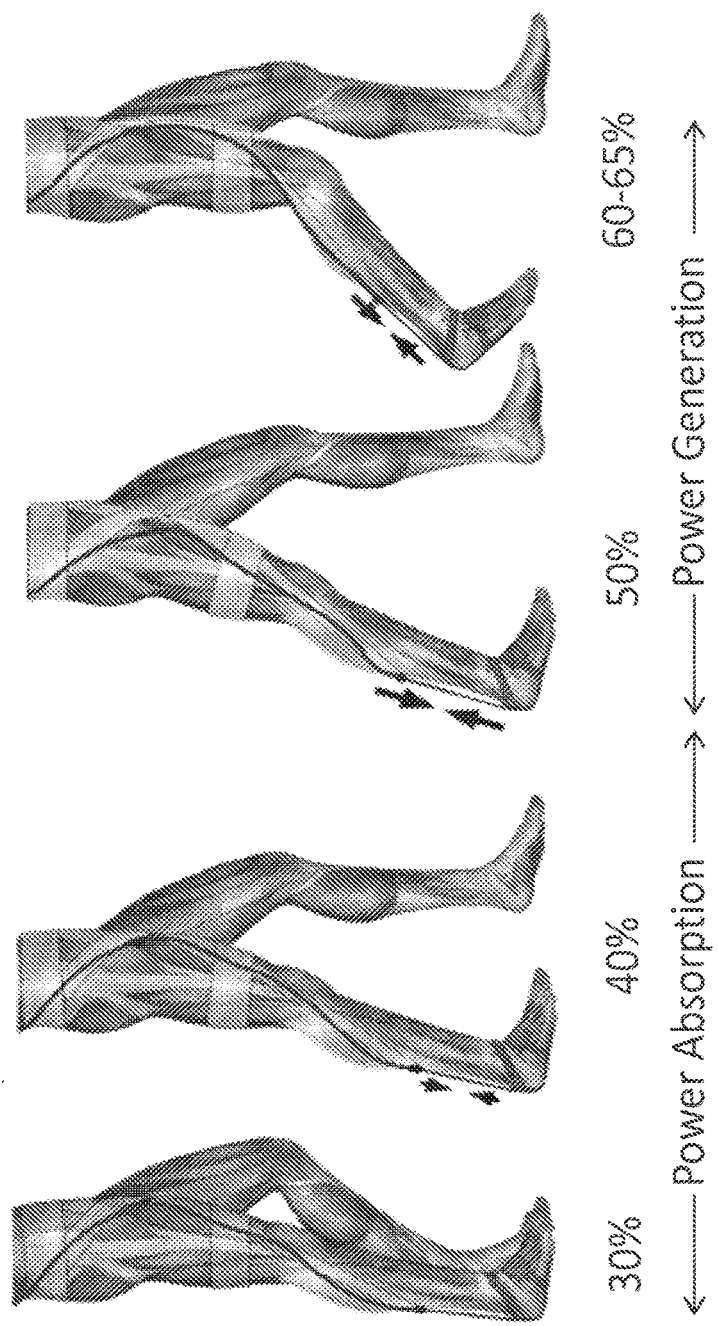
FIG. 27 demonstrates an exosuit producing moments at an ankle simultaneously with an underlying muscle during 30-60% in a gait cycle.

Referring to FIG. 27 the exosuit produces moments at the ankle simultaneously with the underlying muscles during 30-60% in the gait cycle, which extends from one heel strike to the next for a given leg. During this stage of the gait, the calf muscles and tendons push the body up and forward. Initially, the calf absorbed power by stretching as the body's center of mass falls downward and forward over the planted foot. After around 50% in the gait cycle, this absorbed power is returned to the body as the tendons and ligaments elastically recoil. The muscles in the calf and hip actively contract to supplement this returned power with additional energy.

Control method may behave in a similar way and may allow different strategies to absorb and transmit power in this manner as well by detecting gait events in real-time to estimate when to transition from power absorption to generation: with the actuators held at a fixed length initially (pretension force), the exosuit material itself stretches and the tissue under the suit compresses as the body falls forward. This induces a tension in the suit and absorbs power from the body. After the period of biological power absorption, the suit retracts elastically, returning the energy to the body. This is supplemented by the actuators providing an active force starting at the point in the gait cycle in which the biological ankle joint changes from the power absorption phase to power generation to propel the body upwards and forward.

Ankle control system 700 generates assistance based at least in part on the detection of heel strikes and speed-related events within the same step. As such, the ankle control system 700 may comprise one or more sensors configured to measure angular velocity of the ankle ("rotation sensor"), as previously explained in the context of FIG. 14B. In various embodiments, the sensors may comprise two or more gyros positioned and configured on the exosuit to both detect heel strike and measure ankle speed in real-time.

To that end, in various embodiments, ankle control system 700 may be configured to monitor real-time ankle joint motion measurements to detect the start of the stance plantarflexion motion—that is, when the ankle first changes direction from stance dorsiflexion motion to stance plantarflexion motion after heel strike. Ankle control system 700 may be configured to accomplish this utilizing any of the exemplary methods previously described, or any other suitable method. For example, ankle control system 700, in an embodiment, may first monitor real-time measurements from the gyros (or the IMUs or other suitable sensor) to detect a heel strike, thus ensuring that the foot is on the ground and undergoing "stance" motion. Ankle control system 700 may continue monitoring real-time measurements of ankle angular velocity to detect a zero-crossing in the measured angular velocity of the ankle, indicating that the ankle joint has ceased stance dorsiflexion motion and commenced stance plantarflexion motion.

Ankle control system 700 may be further configured to estimate a duration of the ankle stance plantarflexion motion, and thus a duration for which assistance should be provided. Ankle control system 700 may be configured to accomplish this utilizing any of the exemplary methods previously described, or any other suitable method. To that end, ankle control system 700, in an embodiment, may be configured to estimate the current stride time of the user to estimate how long it will take for the ankle joint to reach the end of the motion stance plantarflexion motion. Similar to the way hip control system 700 may use the hip angle buffer to determine stride time, ankle control system 700 may use the stance ankle velocity buffer to determine stride time. In particular, because the ankle angular velocity measurements are sampled at a known frequency (e.g., 100 Hz), the number of stance ankle angular velocity measurements taken between consecutive heel strike detections is directly related to the time passing during said period. That is, stride time can be calculated by dividing the number of stance ankle angular velocity measurements taken by the sampling frequency. At each detection of heel strike, stride time may be calculated and the stored stance ankle angular velocity data flushed from memory so that the process may be repeated during subsequent cycles. Stride time (either that of the previous cycle or an average of those of a plurality of previous cycles) may then be used to estimate joint motion duration as previously described.

Ankle control system 700, in various embodiments, may be configured to determine the desired peak force, and associated cable position for generating it, utilizing any of the exemplary methods previously described, or any other suitable method. For example, ankle control system 700 may be programmed to deliver a baseline peak force of about 300N in the exosuit to assist the stance ankle plantarflexion motion. This baseline force, of course, could be adjusted to account for any number of factors such as spatial-temporal factors (e.g., locomotive speed) as previously described in the context of FIG. 18A, FIG. 18B, and FIG. 18C, or user weight/loads, amongst others, as previously described. Ankle control system 700 may then utilize the force-based position algorithm previously described, or any other suitable method, to determine appropriate cable position(s) for delivering the desired peak force.

Additionally or alternatively, in various embodiments, ankle control system 700 may utilize a power-based position control algorithm to determine an appropriate cable position for delivering a desired integral power to the hip joint, as previously described. Desired power may be adjusted to account for any number of factors such as spatial-temporal factors (e.g., locomotive speed) as previously described in the context of FIG. 18A, FIG. 18B, and FIG. 18C, or user weight/loads, amongst others, as previously described.

Ankle control system 700, in an embodiment, may then determine an actual integral power delivered by exosuit system 700 to the ankle joint during the preceding cycle as a function of the forces generated and angular velocities of the ankle joint throughout the assistance provided during the preceding cycle. There are two distinct intervals where the biological ankle power is negative (30% to 50% of the gait cycle) and positive (50% to 70% of the gait cycle) during the stance phase. The integral positive power and integral negative powers may be calculated as per equation (5a) and equation (5b), and corresponding active and pretension cable positions may be calculated as per equation (6a) and equation (6b), respectively.

It should be recognized that by determining actuation timing and duration in such a manner, control system 700 may serve to avoid actuating the soft exosuit system 100 in ways that may adversely affect the natural motion of the ankle joint. Stated otherwise, embodiments of ankle control system 700 may serve to ensure that assistance is only provided when the joint is actually undergoing the motion for which assistance is desired. This is a significant improvement over existing systems. For example, should the user suddenly stop during stance dorsiflexion motion, the heel strike and perhaps a subsequent zero ankle velocity will be detected; however a zero-crossing may not occur if the ankle does not continue into stance plantarflexion motion. In such a case, the full initiation trigger will not occur, and actuation will not commence. Similarly, should the user suddenly stop during plantarflexion motion, the initiation trigger will be detected and actuation may commence; however, it will cease immediately upon the stance plantarflexion motion ceasing during the stop. In this way, the user will not suffer from an unnecessary actuation of the suit while standing still after a sudden stop, for example. As another example, should the user suddenly slow down, any adverse actuation may be limited only to the duration of the assistance provided—that is, the estimated assistance duration may be slightly longer than the actual joint motion duration, resulting in longer-than-actually-necessary assistance being provided for that cycle. Of course, ankle control system 700 may understand that a significant change in stride time has occurred, and adjust duration for the following cycle, thereby limiting any adverse effects to the current cycle alone.

Figure 28A:
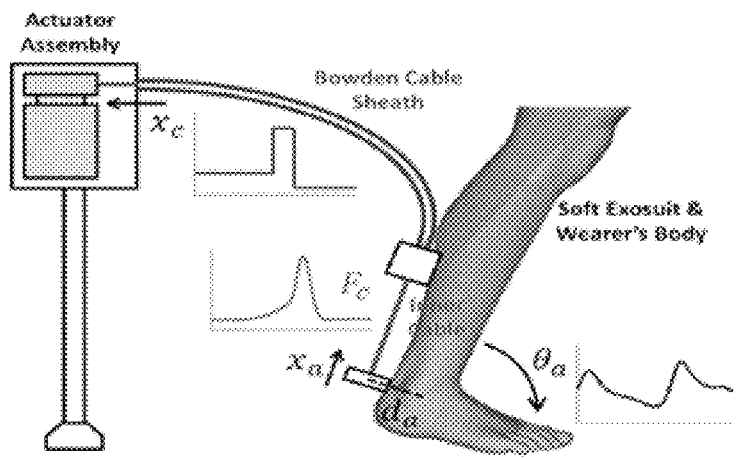
FIG. 28A illustrates a pretension and an active force region of an ankle joint.
Figure 28B:
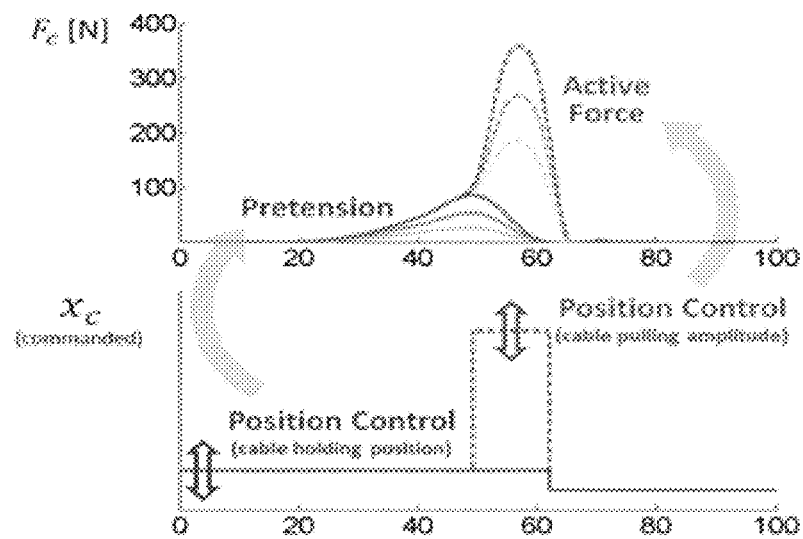
FIG. 28B illustrates a pretension and an active force region of an ankle joint.
Figure 28C:
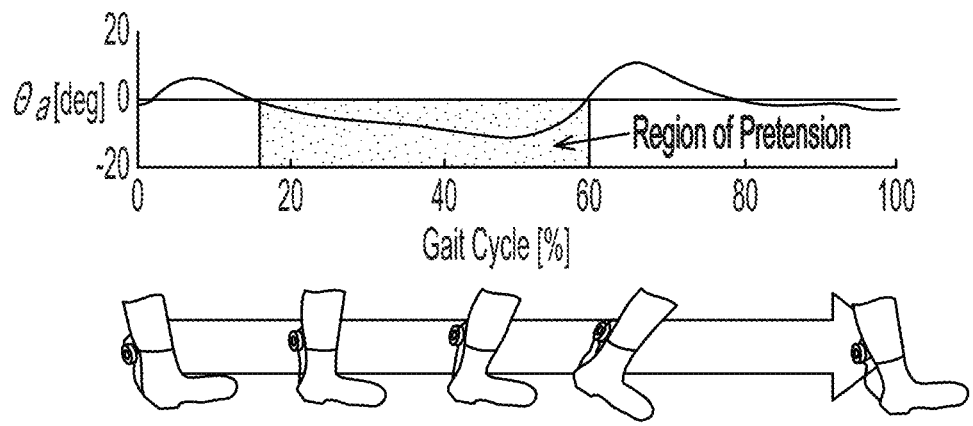
FIG. 28C illustrates a pretension and an active force region of an ankle joint.

The ankle control system 700, in various embodiments, may be further configured to provide negative power assistance to the ankle in addition to the aforementioned positive power assistance. Biomechanically, there is a distinct negative-power interval and a positive-power interval for the ankle joint during a gait cycle. FIG. 28A, FIG. 28B, and FIG. 28C illustrate the pretension and active force regions.

Figures 29A, 29B, 29C, 29D, 29E:
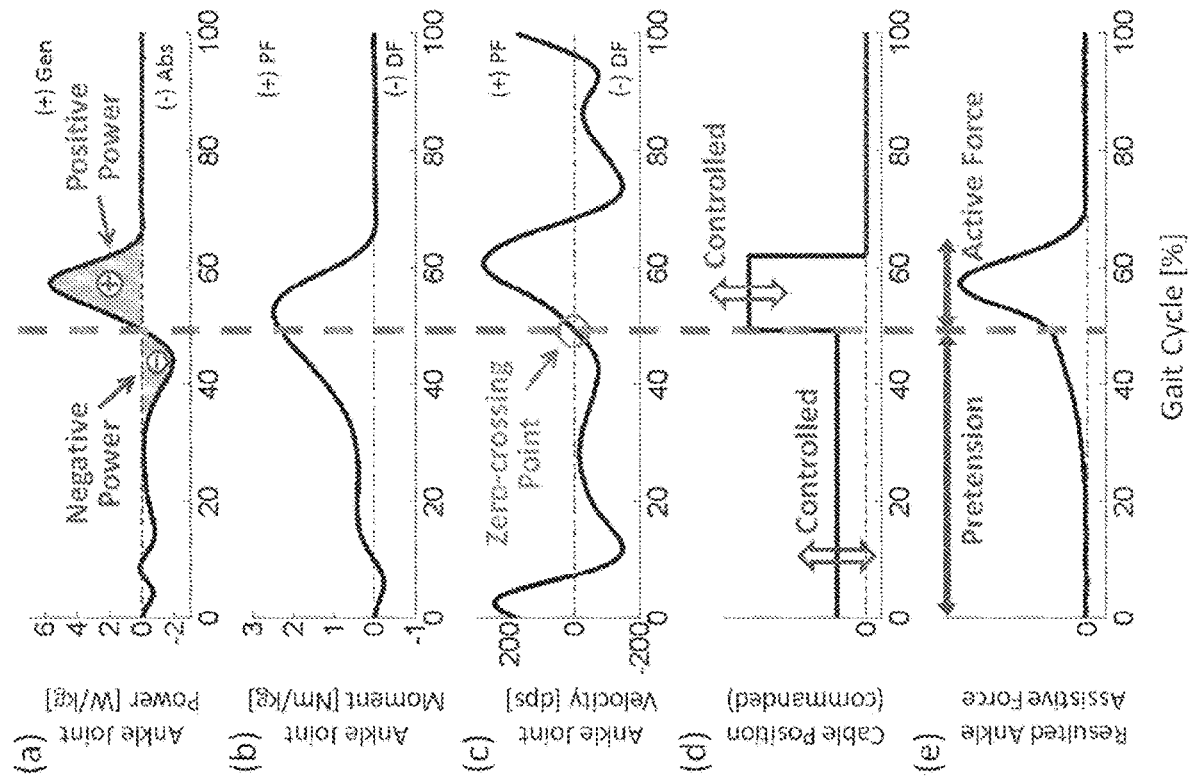
FIG. 29A illustrates relationships between an ankle joint motion and a resulting power.
FIG. 29B illustrates relationships between an ankle joint moment and a resulting power.
FIG. 29C illustrates relationships between an ankle joint velocity and a resulting power.
FIG. 29D illustrates relationships between a commanded cable position and a resulting force.
FIG. 29E illustrates relationships between a resulted ankle assistive force and an active force.

FIG. 29A, FIG. 29B, and FIG. 29C illustrate the relationships between joint motion, commanded cable position, and resulting forces/powers. Ankle control system 700, in various embodiments, may be configured to maintain cable at pretensioning position such that stance dorsiflexion motion of the ankle joint causes the soft exosuit to apply a torque in an opposing direction, thereby generating a negative power in the ankle joint during stance dorsiflexion motion. This negative power may serve to pretension the ankle joint as well as cable to enhance the effectiveness of assistance provided during the subsequent propulsive stance plantarflexion phase. As shown in FIG. 29A, the force delivered before the zero-crossing point will contribute to the negative power for the ankle joint; and the force applied after the zero-crossing point will contribute to the positive ankle power. As shown in FIG. 29D and FIG. 29E, the ankle control system 700 applies the pretension, which refers to the force passively generated by the gait kinematics while the ankle control system 700 is holding the motor position, before the zero-crossing, and generates the active force, which refers to the force actively generated by pulling the motor after the zero-crossing. By controlling the peaks of the pretension and the active force independently, the ankle control system may independently control the positive and the negative powers applied to the ankle.

The gait cycle starts off with the heel striking the ground. The heel strike contact may be detected by a foot switch and/or using the foot and/or shank gyros of the ankle control system. As the foot pivots and the heel lifts off the ground during the push off phase, the two gyros on the foot and the shank are used to measure ankle joint velocity in real time. As shown in FIG. 29A and FIG. 29E, at phase one in the ankle suit force chart, a relatively slow passive force increases to provide negative power resistance. After the zero crossing, and at phase two, a relatively fast force ramp-up provides positive power assistance, as shown in FIG. 29A and FIG. 29E. Subsequently, no force is provided during the swing phase. In an embodiment, the ankle control system may monitor ankle velocity for a second, subsequent zero-crossing after the heel strike as an indicator for when to cease positive power assistance. This second zero-crossing corresponds with a return of the ankle to a normal position during the swing phase after push off.

One of the benefits of using the ankle control system 700 is the delivery assistance is based on real-time measurements rather than using information about previous steps or defining assistance profiles based on gait %. The ankle control system adapts to changes in speed and different biomechanics activities in real-time without having to rely on past information. Additionally the control also applies forces at the appropriate times, rather than applying force that is overdue.

While it is certainly envisioned that the timing and magnitude of ankle assistance could be adjusted in response to detecting an obstacle avoidance motion, it should be recognized that, in various embodiments, such adjustments may not be necessary to avoid inopportune application of a restorative force. As previously described, ankle assistance, in accordance with an embodiment of the present disclosure, may be triggered by detection of a heel strike and continues through subsequent plantar flexion rotation motion. This typically will not occur during an obstacle avoidance motion until the corresponding leg has swung over the obstacle and has touched down on the ground on the far side. As such, the ankle control system, as configured, would not apply assistive force until after the obstacle has been cleared by the corresponding leg and assistive force is again desired to propel the user forward.

Table 4 below illustrates how a controller unit may receive and store into memory (e.g., buffer) ankle angular velocity data at a predetermined frequency (e.g., 100 Hz, or any frequency suitable to monitor joint motion with adequate fidelity for providing tailored assistance). The controller unit may detect a heel strike from this data using the "isHeelStrike" module shown and may detect the first zero-crossing using the "detectZeroCrossing" module shown. If the current ankle angular velocity is greater than zero (i.e., has a sign associated with plantarflexion motion), and the previous angular velocity is less than that threshold (i.e., has a sign associated with dorsiflexion motion), the "detectZeroCrossing" module returns a true logic value; otherwise, the module returns a false logic value. A corresponding true logic value, in an embodiment, may be interpreted as an initiation trigger indicating that stance plantarflexion assistance should commence.

Still referring to Table 4, ankle control system 700 may determine a suitable cable position, referred to in Table 4 as ANKLE_OFFSET, at which cable may be positioned to generate a desired pretensioning force (or a desired integral negative power, or "INP") on the ankle during stance dorsiflexion motion. As shown, a power-based position algorithm may be used to adjust this pretension cable position by a ratio of the desired INP over current INP in an effort to deliver a desired integral negative power to the ankle during dorsiflexion motion. Likewise, ankle control system 700 may determine a suitable cable position, referred to in Table 4 as a positionAnkleAmplitude, at which cable may be positioned to generate a desired force (or a desired integral positive power, or "IPP") on the ankle during stance plantarflexion motion. As shown, a power-based position algorithm may be used to adjust the cable position for assisting stance plantarflexion by a ratio of the desired IPP over the measured IPP in an effort to deliver a desired integral positive power to the ankle during stance plantarflexion motion.

TABLE 4

```
1.      // Global variable, TRUE when we are actuating the ankle
2.      global activationCurrent = FALSE;
3.      // Global variable representing the position magnitude of previous profile
4.      global double positionAnkleAmplitude = DEFAULT_ANKLE_MAGNITUDE
5.
6.      // Returns true if a Zero Crossing event for the ankle speed is detected
7.      // SPEED_THRESHOLD is a predefines ankle speed threshold, could be zero
8.      boolean detectZeroCrossing(angle_speed[buffer]) {
9.          if ( angle_speed(end)>SPEED_THRESHOLD && angle_speed(1:end)<SPEED_TRESHOLD )
10.             return TRUE
11.         else
12.             return FALSE
13.     }
14.
15.     // Returns true if a heel strike event is detected
16.     boolean isHeelStrike(angle_speed[buffer]) {
17.         // Detection of heel strike from foot speed. Not implemented
18.     }
19.
20.     // Returns the maximum value of a buffer
21.     double calculateMaximum(data[buffer]) {
22.         double temp_max = 0;
23.         for(i = 0; i<data.length; i++)
24.             temp_max = max(temp_max, data[i]);
25.     }
26.
27.     // update ankle offset = position pretension to achieve desired pret. Force
28.     void updatePretensionPosition(currentINP, desiredINP) {
29.         if ( abs(currentINP − desiredINP) < EPS) {
30.             ANKLE_OFFSET = ANKLE_OFFSET * desiredINP/currentINP;
31.         }
32.     }
33.
34.     // Generate a position profile to achieve a desired integralPositivePower
35.     double[buffer] generateProfile(stride_time, measured_IPP, desired_IPP){
36.         //correct position amplitude to get closer to desired_Force
37.         positionAnkleAmplitude = positionAnkleAmplitude * desired_IPP/measured_IPP;
38.
39.         // generate trapezoidal position profile of amplitude X and duration stride_time, plateaux high at posAmplitude
40.         positionProfile[buffer] = generateTrapezoid(slope1, slope 2, positionHipAmplitude, stride_time);
41.
42.         return positionProfile;
43.     }
44.
45.     // Generate trapezoid of amplitude posAmplitude, slope 1 and slope 2 slopes, total duration stride time,
46.                 _posAmplitude_
47.     s1   /               \s2
48.         /                 _____
49.     START%           END%       %
50.
51.     trapezoidOutput[buffer] generateTrapezoid(slope1, slope2, posAmplitude, stride_time) {
52.
53.         //not implemented as obvious for anyone of ordinary skill
54.         return trapezoidOutput[buffer];
55.     }
56.
57.     // Retrieve foot/shank angles and speeds from IMUs and calculate angle speed
58.     // Alternatively this function could use gyroscopes
59.     angle[buffer], angle_speed[buffer] calculateAnkleAngle( ) {
60.         return ( IMU_shank.angle − IMU_foot.angle; IMU_shank.speed − IMU_foot.speed)
61.     }
62.
63.     // This loop is executed at a fixed frequency, e.g. 100Hz
```

TABLE 4-continued

```
64.    void loop( ) {
65.
66.        // Add latest angle and force reading to buffer
67.        [angle[buffer], angle_derivative[buffer]] = calculateAnkleAngle( );
68.        force[buffer] = readAnkleForce( );
69.        // Update calculated ankle power
70.        ankle_PositivePower[buffer] = ( Force(1)*angle_derivative(1),
ankle_PositivePower[1:end−1] );
71.
72.        // if we reached heel strike, update stride_time based on buffer of
previous stride times. Start integrating negative power
73.        if (isHeelStrike(getFootSpeed( )) {
74.            stride_time = updateStrideTime( stride_time[buffer], time.now);
75.            integrate_INP = TRUE;
76.            current_INP = 0;
77.        }
78.        // if we detect zero Crossing, actuate ankle and generate assistance
79.        // also start integrating positive power, stop integrating negative
80.        if (isZeroCrossing(angle_derivative[buffer])) {
81.            activationCurrent = TRUE;
82.            integrate_INP = FALSE;
83.            counter = 0;
84.            previous_IPP = Current_IPP;
85.            current_IPP = 0;
86.        // update level of pretension force
87.            current_pretensionForce = Force(1);
88.            updatePositionPretension(current_INP,desired_INP);
89.
90.        //generate position profile with adapted amplitude to reach IPP
91.            position_profile = generateProfile(stride_time, previous_IPP,
desired_IPP);
92.        }
93.
94.        // integrate INP if between heel strike and zero crossing
95.        if ( integrate_INP == TRUE)
96.            current_INP = current_INP + ankle_power(1);
97.
98.        // keep integrating positive power until ankle speed is negative again
99.        // note the negative angle to reverse the detection
100.       if (activationCurrent == TRUE && isZeroCrossing(−angle_derivative[buffer]){
101.           current_IPP = current_IPP + ankle_power(1);
102.       }
103.
104.       // in this section, we just follow the precaculated position profile
105.       if (activationCurrent == TRUE && counter < position_profile.length) {
106.           commandAnkleMotor(position_profile(counter));
107.           counter = counter + 1;
108.       }
```

Recall that, as previously described, hip flexor muscles such as the quadriceps may also be most active during the ankle stance plantarflexion push-off motion. As such, ankle control system 700 may be modified for use in controlling various embodiments of the exosuit in providing hip flexion assistance to help propel the user forward. Ankle control system 700 may be also be used to simultaneously control the provision of flexion assistance to a corresponding hip joint in connection with embodiments of exosuits configured to transfer actuation loads between the ankle and the hip, such those shown in FIG. 12D and FIG. 12E.

In various embodiments, a separate controller may be used for each leg of the user. That is, controller L may be primarily responsible for monitoring and providing assistive motion to one or more joints of the left leg, and a separate controller R may be primarily responsible for that of the right leg. These controllers may act completely independent of one another, or may communicate with one another to any suitable extent. In an embodiment, controllers L and R may pass along loads information from their respective loads cells, for example, such that the system may compare the two and adjust, if desired, the assistive forces applied to each leg to balance one another. In an embodiment, substantially more information may be exchanged; in particular, if there is an asymmetry in functionality of the legs (or joints thereof) that may affect the assistance to be provided to the opposing leg. Of course, a single controller may process all controls as well.

Example Embodiments for Hip and Ankle Control Systems and Methods

In some embodiments of the present disclosure, there is provided a method of assisting motion of a hip joint, comprising determining a desired peak force to be generated by a wearable robotic system during a current gait cycle of a user, generating an actuation profile according to which the wearable robotic system is actuated to generate the desired peak force, monitoring real-time measurements of an angle of the hip joint to detect when the hip joint reaches a maximum flexion angle, and in response to detecting that the angle of the hip joint has reached the maximum flexion angle, actuating the wearable robotic system according to the actuation profile to assist with an extension motion of the hip joint of the user. In some embodiments, the desired peak force is a predetermined baseline force. In some embodiments, the actuation profile defines a position of an actuator of the wearable robotic system that is configured to generate a corresponding force in the wearable robotic system at a given point in the current gait cycle of the user. In some embodiments, the actuation profile is substantially trapezoidal in shape so as to provide a substantially triangular force profile having a peak defined by the desired peak force. In some embodiments, the actuation assists an extension motion of the body joint. In some embodiments wherein the actuation profile is substantially trapezoidal in shape so as to provide a substantially triangular force profile having a peak defined by the desired peak force.

In some embodiments, the determining the desired peak force further comprises estimating a speed at which the user is moving based at least in part on measurements of a range of motion of the hip joint and a length of a corresponding leg of the user, and adjusting the predetermined force by a predetermined correction factor associated with the estimated speed at which the user is moving. In some embodiments, estimating the speed at which the user is moving further comprises determining the range of motion of the hip joint of the user from measurements of at least one of the angle or rotational velocity of the hip joint, estimating a step length of the user based on the range of motion and the leg length of the user, monitoring measurements of the angle of the hip joint to determine a step time of the user, and calculating the estimated speed at which the user is moving by dividing the step length by the step time. In some embodiments, the predetermined correction factor is associated with varying physiological moments acting on the hip joint at various speeds.

In some embodiments, generating the actuation profile further comprises measuring a peak force generated by the wearable robotic system during at least one preceding gait cycle of the user, comparing the measured peak force generated during the at least one preceding gait cycle to a desired peak force to be generated during the at least one preceding gait cycle, and adjusting an amplitude of the actuation profile to account for the difference between the measured peak force and the desired peak force generated during the at least one preceding gait cycle. In some embodiments, the position of the actuator increases from a first position to a second position, the second position being configured to generate the desired peak force in the wearable robotic system. In some embodiments, the increase in actuator position occurs upon a detection of a trigger event based at least in part on real-time measurements of joint motion. In some embodiments, the second position is maintained for a majority of the actuation profile. In some embodiments, the position of the actuator subsequently decreases from the second position.

In some embodiments, the method further comprises terminating the actuation of the wearable robotic system when the measured angle of the body joint reaches a predetermined angle, wherein the predetermined angle is an angle of the joint corresponding with when a leg of the user is oriented substantially perpendicular to the ground during the current gait cycle. In some embodiments, the method further comprises estimating, based on a stride time of a preceding gait cycle, a period of time that will pass between a start of the actuation and a predetermined percentage of the gait cycle, and terminating the actuation at the end of the period of time, wherein the predetermined percentage is about 40% of the stride time.

In some embodiments, the method further comprises determining an average maximum flexion angle of the hip joint throughout a plurality of previous gait cycles, detecting that the angle of the hip joint during the current gait cycle has exceeded, by a predetermined threshold, the average maximum flexion angle throughout the plurality of previous gait cycles, and delaying the start of the actuating until after the angle of the hip joint during the current gait cycle returns below the average maximum flexion angle throughout the previous gait cycles.

In some embodiments of the present disclosure, there is provided a wearable robotic system for motion assistance to a hip joint of a user comprising at least one sensor adapted to monitor real-time measurements of an angle of the hip joint to detect when the hip joint reaches a maximum flexion angle, and at least one processor that is adapted to obtains computer executable instructions stored on a non-transitory medium that when executed by the at least one processor causes the wearable robotic system to determine a desired peak force to be generated by the wearable robotic system during a current gait cycle of the user, create an actuation profile according to which the wearable robotic system is actuated to generate the desired peak force, detect when the angle of the hip joint has reached the maximum flexion angle, and actuate the wearable robotic system according to the actuation profile to assist with an extension motion of the hip joint of the user in response to detecting the hip joint reached the maximum flexion angle. In some embodiments, the desired peak force is a predetermined baseline force. In some embodiments, the actuation assists an extension motion of the body joint. In some embodiments, the computer executable instructions, when executed by the at least one processor, causes the wearable robotic system to determine an average maximum flexion angle of the hip joint throughout a plurality of previous gait cycles, to detect that the angle of the hip joint during the current gait cycle has exceeded, by a predetermined threshold, the average maximum flexion angle throughout the plurality of previous gait cycles, and to delay the start of the actuating until after the angle of the hip joint during the current gait cycle returns below the average maximum flexion angle throughout the previous gait cycles.

In some embodiments the computer executable instructions, when executed by the at least one processor, causes the wearable robotic system to determine the desired peak force by performing at least the following: estimate a speed at which the user is moving based at least in part on measurements of a range of motion of the hip joint and a length of a corresponding leg of the user, and adjust the predetermined force by a predetermined correction factor associated with the estimated speed at which the user is moving. In some embodiments, the computer executable instructions, when executed by the at least one processor, causes the wearable robotic system to estimate the speed at which the user by performing at least the following: determine the range of motion of the hip joint of the user from measurements of at least one of the angle or rotational velocity of the hip joint, estimate a step length of the user based on the range of motion and the leg length of the user, monitor measurements of the angle of the hip joint to determine a step time of the user, and calculate the estimated speed at which the user is moving by dividing the step length by the step time. In some embodiments, the predetermined correction factor is associated with varying physiological moments acting on the hip joint at various speeds.

In some embodiments, the computer executable instructions, when executed by the at least one processor, causes the wearable robotic system to generate the actuation profile by performing at least the following: measuring a peak force generated by the wearable robotic system during at least one preceding gait cycle of the user with at least one second sensor, comparing the measured peak force generated during the at least one preceding gait cycle to a desired peak force to be generated during the at least one preceding gait cycle, and adjusting an amplitude of the actuation profile to account for the difference between the measured peak force and the desired peak force generated during the at least one preceding gait cycle. In some embodiments, the position of the actuator increases from a first position to a second position, and wherein the second position of the actuator generates the desired peak force in the wearable robotic system. In some embodiments, the increase in actuator position occurs upon a detection of a trigger event based at least in part on real-time measurements of joint motion. In some embodiments, the second position is maintained for a majority of the actuation profile. In some embodiments, the position of the actuator subsequently decreases from the second position.

In some embodiments, the computer executable instructions, when executed by the at least one processor, causes the wearable robotic system to terminate the actuation of the wearable robotic system when the measured angle of the body joint reaches a predetermined angle. In some embodiments, the predetermined angle is an angle of the joint corresponding with when a leg of the user is oriented substantially perpendicular to the ground during the current gait cycle.

In some embodiments, the computer executable instructions, when executed by the at least one processor, causes the wearable robotic system to: estimate, based on a stride time of a preceding gait cycle, a period of time that will pass between a start of the actuation and a predetermined percentage of the gait cycle, and terminate the actuation at the end of the period of time. In some embodiments, the predetermined percentage is about 40% of the stride time.

In some embodiments, the system further comprises an actuator which is configured to generate a corresponding force in the wearable robotic system at a given point in the current gait cycle of the user, wherein the actuation profile defines a position of the actuator. In some embodiments, the actuation profile is substantially trapezoidal in shape to provide a substantially triangular force profile having a peak defined by the desired peak force In some embodiments, there is disclosed a method of assisting motion of an ankle joint, comprising determining a desired peak force to be generated by a wearable robotic system during a current gait cycle of a user, generating an actuation profile according to which the wearable robotic system may be actuated to deliver the desired peak force to the body of the user, detecting a heel strike of the user, monitoring real-time measurements of a rotational velocity of the ankle of the user to detect a first change in direction of the measured rotational velocity of the ankle joint after the detection of the heel strike, and in response to detecting the first change in direction of the measured rotational velocity of the ankle joint, actuating the wearable robotic system according to the actuation profile to assist with an plantarflexion motion of the ankle joint of the user. In some embodiments, the desired peak force is a predetermined baseline force. In some embodiments, the actuation profile defines a position of an actuator of the wearable robotic system that is configured to generate a corresponding force in the wearable robotic system at a given point in the current gait cycle of the user. In some embodiments, a resulting torque generated about the ankle joint by the actuation of the wearable robotics system acts in concert with the motion of the ankle joint so as to apply a positive power to the ankle joint to assist with plantarflexion motion of the ankle joint. In some embodiments, the resulting torque helps to propel the user forward.

In some embodiments, determining the desired peak force further comprises estimating a speed at which the user is moving based at least in part on measurements of a range of motion of the hip joint and a length of a corresponding leg of the user, and adjusting the predetermined force by a predetermined correction factor associated with the estimated speed at which the user is moving. In some embodiments, the predetermined correction factor is associated with varying physiological moments acting on the ankle joint at various speeds. In some embodiments, estimating the speed at which the user is moving further comprises determining the range of motion of the hip joint of the user from measurements of at least one of the angle or rotational velocity of the hip joint, estimating a step length of the user based on the range of motion and the leg length of the user, monitoring measurements of the angle of the hip joint to determine a step time of the user, and calculating the estimated speed at which the user is moving by dividing the step length by the step time.

In some embodiments, generating the actuation profile further comprises measuring a peak force generated by the wearable robotic system during at least one preceding gait cycle of the user, comparing the measured peak force generated during the at least one preceding gait cycle to a desired peak force to be generated during the at least one preceding gait cycle, and adjusting an amplitude of the actuation profile to account for the difference between the measured peak force and the desired peak force generated during the at least one preceding gait cycle. In some embodiments, the first position of the actuator is configured such that the wearable robotic system exerts a proportionally increasing force on the ankle joint during at least portion of motion of the ankle joint occurring between the heel strike and the first change in direction of the measured rotational velocity of the ankle joint. In some embodiments, the exerted force results in a torque that opposes the motion of the ankle joint so as to apply a negative power to the ankle joint during the corresponding motion. In some embodiments, wherein the resulting torque serves to pretension the ankle joint during corresponding stance dorsiflexion motion.

In some embodiments, the position of the actuator increases from a first position to a second position, the second position being configured to generate the desired peak force in the wearable robotic system. In some embodiments, the increase in actuator position occurs upon a detection of a trigger event based at least in part on real-time measurements of joint motion. In some embodiments the second position is maintained for a majority of the actuation profile. In some embodiments the second position is maintained in the actuation profile for duration corresponding with an estimated duration of the joint motion to be assisted during the current gait cycle. In some embodiments, the position of the actuator subsequently decreases from the second position. In some embodiments, the estimated duration of the joint motion to be assisted during the current gait cycle is based at least in part on measurements of the rotational velocity of the joint during the preceding gait cycle.

In some embodiments, the method further comprises terminating the actuation of the wearable robotic system when the measured rotational velocity of the ankle joint subsequently reaches a predetermined velocity. In some embodiments the predetermined velocity is about zero.

In some embodiments, the method further comprises estimating, based on a stride time of a preceding gait cycle, a period of time that will pass between a start of the actuation and a predetermined percentage of the gait cycle, and terminating the actuation at the end of the period of time.

In some embodiments, determining the desired peak force further comprises measuring a force generated by the wearable robotic system during the at least one preceding gait cycle of the user, monitoring real-time measurements of a rotational velocity of the ankle of the user to detect a second change in direction of the measured rotational velocity of the ankle joint after the first change in direction of the measured rotational velocity of the ankle joint, computing an integral positive power generated by the wearable robotic system during the period of time from the detected first change in direction of the measured rotational velocity of the ankle joint to the detected second change in direction of the measured rotational velocity of the ankle joint, wherein the integral positive power is determined by multiplying the measured force with a corresponding measured rotational velocity of the ankle joint, comparing the measured integral positive power during the at least one preceding gait cycle to a desired integral positive power to be generated during the at least one preceding gait cycle, and adjusting the predetermined amplitude of the actuation profile to account for the difference between the measured integral positive power and the desired integral positive power generated during the at least one preceding gait cycle.

In some embodiments, determining the desired peak force further comprises measuring a pretension force generated by the wearable robotic system during the at least one preceding gait cycle of the user, computing an integral negative power generated by the wearable robotic system during the period of time from the detection of the heel strike to the detected first change in direction of the measured rotational velocity of the ankle joint by multiplying the measured pretension force with the measured rotational velocity of the ankle joint, comparing the measured integral negative power during the at least one preceding gait cycle to a desired integral negative power to be generated during the at least one preceding gait cycle, and adjusting the predetermined amplitude of the actuation profile to account for the difference between the measured integral negative power and the desired integral negative power generated during the at least one preceding gait cycle.

In some embodiments of the present disclosure, there is provided a wearable robotic system for motion assistance to an ankle joint of a user comprising at least one sensor adapted to monitor real-time measurements of a rotational velocity of the ankle of the user to detect a first change in direction of the measured rotational velocity of the ankle joint after the detection of a heel strike; and at least one processor that is adapted to obtains computer executable instructions stored on a non-transitory medium that when executed by the at least one processor causes the wearable robotic system to: determine a desired peak force to be generated by the wearable robotic system during a current gait cycle of the user; generate an actuation profile according to which the wearable robotic system may be actuated to deliver the desired peak force to the body of the user; detect the heel strike of the user; detect the first change in direction of the measured rotational velocity of the ankle joint; and actuate the wearable robotic system according to the actuation profile to assist with an plantarflexion motion of the ankle joint of the user in response to detecting the first change in direction of the measured rotational velocity of the ankle joint.

In some embodiments, the desired peak force is a predetermined baseline force.

In some embodiments, the computer executable instructions, when executed by the at least one processor, causes the wearable robotic system to determine the desired peak force by performing at least the following: estimate a speed at which the user is moving based at least in part on measurements of a range of motion of the hip joint and a length of a corresponding leg of the user; and adjust the predetermined force by a predetermined correction factor associated with the estimated speed at which the user is moving.

In some embodiments, the computer executable instructions, when executed by the at least one processor, causes the wearable robotic system to estimate the speed at which the user by performing at least the following: determine the range of motion of the hip joint of the user from measurements of at least one of the angle or rotational velocity of the hip joint; estimate a step length of the user based on the range of motion and the leg length of the user; monitor measurements of the angle of the hip joint to determine a step time of the user; and calculate the estimated speed at which the user is moving by dividing the step length by the step time.

In some embodiments, the predetermined correction factor is associated with varying physiological moments acting on the ankle joint at various speeds.

In some embodiments, the system further comprises an actuator is configured to generate a corresponding force in the wearable robotic system at a given point in the current gait cycle of the user, wherein the actuation profile defines a position of the actuator.

In some embodiments, wherein the computer executable instructions, when executed by the at least one processor, causes the wearable robotic system to generate the actuation profile by performing at least the following: measure a peak force generated by the wearable robotic system during at least one preceding gait cycle of the user; compare the measured peak force generated during the at least one preceding gait cycle to a desired peak force to be generated during the at least one preceding gait cycle; and adjust an amplitude of the actuation profile to account for the difference between the measured peak force and the desired peak force generated during the at least one preceding gait cycle.

In some embodiments, the position of the actuator increases from a first position to a second position, the second position being configured to generate the desired peak force in the wearable robotic system.

In some embodiments, the increase in actuator position occurs upon a detection of a trigger event based at least in part on real-time measurements of joint motion.

In some embodiments, the second position is maintained for a majority of the actuation profile. In some embodiments, the second position is maintained in the actuation profile for duration corresponding with an estimated duration of the joint motion to be assisted during the current gait cycle.

In some embodiments, the estimated duration of the joint motion to be assisted during the current gait cycle is based at least in part on measurements of the rotational velocity of the joint during the preceding gait cycle.

In some embodiments, the position of the actuator subsequently decreases from the second position.

In some embodiments, the actuation profile is substantially trapezoidal in shape so as to provide a substantially triangular force profile having a peak defined by the desired peak force.

In some embodiments, the computer executable instructions, when executed by the at least one processor, causes the wearable robotic system to terminate the actuation of the wearable robotic system when the measured rotational velocity of the ankle joint subsequently reaches a predetermined velocity. In some embodiments, the predetermined velocity is about zero.

In some embodiments, the computer executable instructions, when executed by the at least one processor, causes the wearable robotic system to: estimate, based on a stride time of a preceding gait cycle, a period of time that will pass between a start of the actuation and a predetermined percentage of the gait cycle; and terminate the actuation at the end of the period of time.

In some embodiments, a resulting torque generated about the ankle joint by the actuation of the wearable robotics system acts in concert with the motion of the ankle joint so as to apply a positive power to the ankle joint to assist with plantarflexion motion of the ankle joint. In some embodiments, the resulting torque helps to propel the user forward.

In some embodiments, the first position of the actuator is configured such that the wearable robotic system exerts a proportionally increasing force on the ankle joint during at least portion of motion of the ankle joint occurring between the heel strike and the first change in direction of the measured rotational velocity of the ankle joint. In some embodiments, the exerted force results in a torque that opposes the motion of the ankle joint so as to apply a negative power to the ankle joint during the corresponding motion. In some embodiments, the resulting torque serves to pretension the ankle joint during corresponding stance dorsiflexion motion.

In some embodiments, the computer executable instructions, when executed by the at least one processor, causes the wearable robotic system to generate the actuation profile by performing at least the following: measure a force generated by the wearable robotic system during the at least one preceding gait cycle of the user; compute an integral positive power generated by the wearable robotic system during the period of time from the detected first change in direction of the measured rotational velocity of the ankle joint to a detected second change in direction of the measured rotational velocity of the ankle joint by multiplying the measured force with the measured rotational velocity of the ankle joint; compare the measured integral positive power during the at least one preceding gait cycle to a desired integral positive power to be generated during the at least one preceding gait cycle; and adjust the predetermined amplitude of the actuation profile to account for the difference between the measured integral positive power and the desired integral positive power generated during the at least one preceding gait cycle.

System Hardware and Architecture

Embodiments of exosuit system 100, and control systems 500, 600 and 700, may be implemented using suitable hardware and architecture. With reference to FIG. 15, exosuit system 100 may include a controller unit that may correspond to or may be part of the drive module, actuator/control unit, one or a combination of embodiments of control systems 500, 600, 700 and/or any other control device used for an exosuit. The controller unit includes a processor, which may be also be referenced as a central processor unit (CPU), such as the Diamond Systems Aurora single board computer. The processor may communicate (e.g., via a system bus) and/or provide instructions to other components within the controller unit, such as the input interface, output interface, and/or memory. In an embodiment, the processor may include one or more multi-core processors and/or memory (e.g., cache memory) that function as buffers and/or storage for data. In other words, processor may be part of one or more other processing components, such as application specific integrated circuits (ASICs), field-programmable gate arrays (FPGAs), and/or digital signal processors (DSPs). Although FIG. 26 illustrates that processor may be a single processor, processor is not so limited and instead may represent a plurality of processors. The processor may be configured to implement any of the methods described herein.

Memory may be operatively coupled to processor. Memory may be a non-transitory computer readable medium configured to store various types of sensory data and/or the force-based position control algorithm. For example, memory may include one or more memory devices that comprise secondary storage, read-only memory (ROM), random-access memory (RAM), and/or other types of memory storage. The secondary storage is typically comprised of one or more disk drives, optical drives, solid-state drives (SSDs), and/or tape drives and is used for non-volatile storage of data. In certain instances, the secondary storage may be used to store overflow data if the allocated RAM is not large enough to hold all working data. The secondary storage may also be used to store programs that are loaded into the RAM when such programs are selected for execution. The ROM is used to store instructions and perhaps data that are read during program execution. The ROM is a non-volatile memory device that typically has a small memory capacity relative to the larger memory capacity of the secondary storage. The RAM is used to store volatile data and perhaps to store computer executable instructions, such as the force-based position control algorithm.

The memory may be used to house the instructions for carrying out various embodiments described herein. In an embodiment, the memory may comprise an actuator control module that may be accessed and implemented by processor. Alternatively, the actuator control module may be stored and accessed within memory embedded in processor (e.g., cache memory). Specifically, the actuator control module may regulate and control the force generated in the soft exosuit by controlling the length a cable and/or regulate and the control the power delivered to the ankle and/or other types of joints. In an embodiment, memory interfaces with a computer bus so as to communicate and/or transmit information stored in memory to processor during execution of software programs, such as software modules that comprise program code, and/or computer executable process steps, incorporating functionality described herein, e.g., the actuator control module. Processor first loads computer executable process steps from storage, e.g., memory, storage medium/media, removable media drive, and/or other storage device. Processor can then execute the stored process steps in order to execute the loaded computer executable process steps. Stored data, e.g., data stored by a storage device, can be accessed by processor during the execution of computer executable process steps to instruct one or more components within the controller unit and/or outside the controller unit, such as motors and mechanical components associated with an exosuit.

Programming and/or loading executable instructions onto memory and processor in order to transform the exosuit system into a non-generic, particular machine or apparatus that controls and drives one or more motors in an exosuit is well-known in the art. Implementing instructions, real-time monitoring, and other functions by loading executable software into a computer and/or processor can be converted to a hardware implementation by well-known design rules and/or transform a general-purpose processor to a processor programmed for a specific application. For example, decisions between implementing a concept in software versus hardware may depend on a number of design choices that include stability of the design and numbers of units to be produced and issues involved in translating from the software domain to the hardware domain. Often a design may be developed and tested in a software form and subsequently transformed, by well-known design rules, to an equivalent hardware implementation in an ASIC or application specific hardware that hardwires the instructions of the software. In the same manner as a machine controlled by a new ASIC is a particular machine or apparatus, likewise a computer that has been programmed and/or loaded with executable instructions may be viewed as a non-generic particular machine or apparatus.

The processor may be operatively coupled to an input interface configured to receive sensory data. The input interface may be configured to obtain biomechanics data, such as thigh angle, thigh rotational velocity, ankle rotation velocity and heel strikes, via electrical, optical, and/or wireless connections. The output interface may be an interface may communicate instructions used to drive a variety of electro-mechanical and/or mechanical device, such as motors for an exosuit.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" and "substantially" means±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

Of course, the above referenced control systems may be used independently or in concert with one another to deliver a combination of assistive torque to a user's hip and/or ankle using any suitable embodiment of the soft exosuit described above.

In various embodiments, a separate controller may be used for each leg of the user. That is, controller L may be primarily responsible for monitoring and providing assistive motion to one or more joints of the left leg, and a separate controller R may be primarily responsible for that of the right leg. These controllers may act completely independent of one another, or may communicate with one another to any suitable extent. In an embodiment, controllers L and R may pass along loads information from their respective loads cells, for example, such that the system may compare the two and adjust, if desired, the assistive forces applied to each leg to balance one another. In an embodiment, substantially more information may be exchanged; in particular, if there is an asymmetry in functionality of the legs (or joints thereof) that may affect the assistance to be provided to the opposing leg. Of course, a single controller may process all controls as well.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A method of assisting motion of a joint, comprising:
    determining a desired peak force and/or power to be generated by a wearable robotic system during a current motion cycle of a user;
    monitoring real-time measurements of the motion of the joint of the user to detect a change in direction of the motion of the joint;
    generating an actuation profile according to which the wearable robotic system is actuated to deliver the desired peak force and/or power to a body of the user, wherein the actuation profile is generated based at least in part on:
        the desired peak force and/or power; and
        an adjustment related to a difference between a measured peak force and/or power and the desired peak force and/or power during at least one preceding motion cycle of the user; and
    in response to detecting the change in direction of the motion of the joint, actuating the wearable robotic system according to the actuation profile to assist with the motion of the joint of the user.

2. The method of claim 1, wherein monitoring real-time measurements of the motion of the joint includes monitoring real-time measurements of at least one selected from the group of an angle of the joint and a rotational velocity of the joint.

3. The method of claim 1, wherein the joint is an ankle of the user.

4. The method of claim 3, wherein the motion to be assisted is ankle plantarflexion.

5. The method of claim 3, wherein the motion to be assisted is ankle dorsiflexion.

6. The method of claim 1, wherein the joint is a hip of the user.

7. The method of claim 6, wherein the change in direction of the joint is from maximum hip flexion to hip extension, and wherein the motion to be assisted is hip extension.

8. The method of claim 6, wherein the change in direction of the joint is from maximum hip extension to hip flexion, and wherein the motion to be assisted is hip flexion.

9. The method of claim 1, wherein determining the desired peak force and/or power includes estimating a speed at which the user is moving and adjusting the desired peak force and/or power based at least partly on the estimated speed at which the user is moving.

10. The method of claim 1, further comprising terminating the actuation of the wearable robotic system when the measured motion of the joint subsequently reaches a predetermined angle and/or rotational velocity.

11. A wearable robotic system for assisting motion of a joint of a user, the system comprising:
at least one sensor adapted to monitor real-time measurements of the motion of the joint;
at least one processor configured to:
determine a desired peak force and/or integral power to be generated by the wearable robotic system during a current motion cycle of the user;
generate an actuation profile according to which the wearable robotic system may be actuated to deliver the desired peak force and/or power to a body of the user, and wherein the processor is configured to generate the actuation profile base at least in part on:
the desired peak force and/or power; and
an adjustment related to a difference between a measured peak force and/or power and the desired peak force and/or power during at least one preceding motion cycle of the user;
detect a change in direction of the motion of the joint; and
actuate the wearable robotic system according to the actuation profile to assist with the motion of the joint of the user in response to detecting the change in direction of the motion of the joint.

12. The wearable robotic system of claim 11, wherein the sensor is configured to monitor real-time measurements of at least one selected from the group of an angle of the joint and a rotational velocity of the joint.

13. The wearable robotic system of claim 11, wherein the joint is an ankle of the user.

14. The wearable robotic system of claim 13, wherein the motion to be assisted is ankle plantarflexion.

15. The wearable robotic system of claim 13, wherein the motion to be assisted is ankle dorsiflexion.

16. The wearable robotic system of claim 11, wherein the joint is a hip of the user.

17. The wearable robotic system of claim 16, wherein the change in direction of the joint is from hip flexion to extension, and wherein the motion to be assisted is hip extension.

18. The wearable robotic system of claim 16, wherein the change in direction of the joint is from hip extension to flexion, and wherein the motion to be assisted is hip flexion.

19. The wearable robotic system of claim 11, wherein the processor is configured to estimate a speed at which the user is moving and adjust the desired peak force and/or power based at least partly on the estimated speed at which the user is moving.

20. The wearable robotic system of claim 11, wherein the processor is configured to terminate actuation of the wearable robotic system when a measured motion of the joint reaches a predetermined angle and/or rotational velocity.

21. The method of claim 1, wherein the joint is a leg joint of the user and the motion cycle is a gait cycle of the user.

22. A method of assisting motion of a joint, comprising:
determining a desired peak force and/or power to be generated by a wearable robotic system during a current motion cycle of a user;
monitoring real-time measurements of the motion of the joint of the user to detect a change in direction of the motion of the joint;
generating an actuation profile according to which the wearable robotic system is actuated to deliver the desired peak force and/or power to a body of the user, wherein the actuation profile is generated based at least in part on:
the desired peak force and/or power; and
an adjustment related to a difference between a measured peak force and/or power and the desired peak force and/or power during at least one preceding motion cycle of the user; and
in response to detecting the change in direction of the motion of the joint, adjusting the actuation profile to assist with the motion of the joint of the user.

23. The method of claim 22, wherein monitoring real-time measurements of the motion of the joint includes monitoring real-time measurements of at least one selected from the group of an angle of the joint and a rotational velocity of the joint.

24. The method of claim 22, wherein the joint is an ankle of the user.

25. The method of claim 24, wherein the motion to be assisted is ankle plantarflexion.

26. The method of claim 24, wherein the motion to be assisted is ankle dorsiflexion.

27. The method of claim 22, wherein the joint is a hip of the user.

28. The method of claim 27, wherein the change in direction of the joint is from maximum hip flexion to hip extension, and wherein the motion to be assisted is hip extension.

29. The method of claim 27, wherein the change in direction of the joint is from maximum hip extension to hip flexion, and wherein the motion to be assisted is hip flexion.

30. The method of claim 22, wherein determining the desired peak force and/or power includes estimating a speed at which the user is moving and adjusting the desired peak force and/or power based at least partly on the estimated speed at which the user is moving.

31. The method of claim 22, further comprising terminating the actuation of the wearable robotic system when the measured motion of the joint subsequently reaches a predetermined angle and/or rotational velocity.

32. The method of claim 22, wherein the joint is a leg joint of the user and the motion cycle is a gait cycle of the user.

* * * * *